US008343728B2

(12) United States Patent
Goix et al.

(10) Patent No.: US 8,343,728 B2
(45) Date of Patent: Jan. 1, 2013

(54) HIGHLY SENSITIVE SYSTEM AND METHOD FOR ANALYSIS OF TROPONIN

(75) Inventors: Philippe J. Goix, Oakland, CA (US); Robert Puskas, Manchester, MO (US); John Todd, Lafayette, CA (US); Richard A. Livingston, Webster Groves, MO (US); Douglas Held, Ballwin, MO (US); Alan Wu, Palo Alto, CA (US)

(73) Assignees: Singulex, Inc., Alameda, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 12/902,182

(22) Filed: Oct. 12, 2010

(65) Prior Publication Data

US 2011/0111524 A1 May 12, 2011

Related U.S. Application Data

(63) Continuation of application No. 12/062,412, filed on Apr. 3, 2008, now Pat. No. 7,838,250, which is a continuation-in-part of application No. 11/784,213, filed on Apr. 4, 2007.

(60) Provisional application No. 60/914,995, filed on Apr. 30, 2007, provisional application No. 60/925,402, filed on Apr. 19, 2007, provisional application No. 60/789,304, filed on Apr. 4, 2006, provisional application No. 60/793,664, filed on Apr. 19, 2006, provisional application No. 60/808,622, filed on May 26, 2006, provisional application No. 60/861,498, filed on Nov. 28, 2006, provisional application No. 60/872,986, filed on Dec. 4, 2006.

(51) Int. Cl.
*G01N 33/53* (2006.01)
(52) U.S. Cl. .................................... 435/7.1; 436/518
(58) Field of Classification Search .................. None
See application file for complete search history.

(56) References Cited

U.S. PATENT DOCUMENTS

| | | | |
|---|---|---|---|
| 4,071,298 A | 1/1978 | Falconer | |
| 4,172,227 A | 10/1979 | Tyrer et al. | |
| 4,243,318 A | 1/1981 | Stohr | |
| 4,251,733 A | 2/1981 | Hirleman | |
| 4,521,733 A | 6/1985 | Bottomley | |
| 4,768,879 A | 9/1988 | McLachlan et al. | |
| 4,793,705 A | 12/1988 | Shera | |
| 4,927,265 A | 5/1990 | Brownlee | |
| 4,979,824 A | 12/1990 | Mathies et al. | |

(Continued)

FOREIGN PATENT DOCUMENTS

WO WO 90/10876 A1 9/1990

(Continued)

OTHER PUBLICATIONS

Missov et al. (Circulation 1997 vol. 96, pshr 2953-2958).*

(Continued)

*Primary Examiner* — Jacob Cheu
(74) *Attorney, Agent, or Firm* — McDonnell Boehnen Hulbert & Berghoff LLP

(57) ABSTRACT

The invention provides methods, compositions, kits, and systems for the sensitive detection of cardiac troponin. Such methods, compositions, kits, and systems are useful in diagnosis, prognosis, and determination of methods of treatment in conditions that involve release of cardiac troponin.

21 Claims, 18 Drawing Sheets

Distribution of cTNI in chest pain specimens

U.S. PATENT DOCUMENTS

| | | |
|---|---|---|
| 5,002,389 A | 3/1991 | Benser |
| 5,041,733 A | 8/1991 | Noguchi et al. |
| 5,094,594 A | 3/1992 | Brennan |
| 5,108,179 A | 4/1992 | Myers |
| 5,138,170 A | 8/1992 | Noguchi et al. |
| 5,209,834 A | 5/1993 | Shera |
| 5,230,997 A | 7/1993 | Frenkel |
| 5,269,937 A | 12/1993 | Dollinger et al. |
| 5,480,614 A | 1/1996 | Kamahori |
| 5,540,494 A | 7/1996 | Purvis, Jr. et al. |
| 5,543,838 A | 8/1996 | Hosier et al. |
| 5,547,849 A | 8/1996 | Baer et al. |
| 5,571,410 A | 11/1996 | Swedberg et al. |
| 5,603,351 A | 2/1997 | Cherukuri et al. |
| 5,605,351 A | 2/1997 | Higashino |
| 5,605,662 A | 2/1997 | Heller et al. |
| 5,633,503 A | 5/1997 | Kosaka |
| 5,645,702 A | 7/1997 | Witt et al. |
| 5,653,859 A | 8/1997 | Parton et al. |
| 5,653,939 A | 8/1997 | Hollis et al. |
| 5,658,413 A | 8/1997 | Kaltenbach et al. |
| 5,681,751 A | 10/1997 | Begg et al. |
| 5,682,038 A | 10/1997 | Hoffman |
| 5,716,825 A | 2/1998 | Hancock et al. |
| 5,730,187 A | 3/1998 | Howitz et al. |
| 5,746,901 A | 5/1998 | Balch et al. |
| 5,755,942 A | 5/1998 | Zanzucchi et al. |
| 5,770,029 A | 6/1998 | Nelson et al. |
| 5,793,485 A | 8/1998 | Gourley |
| 5,798,222 A | 8/1998 | Goix |
| 5,807,677 A | 9/1998 | Eigen et al. |
| 5,858,195 A | 1/1999 | Ramsey |
| 5,863,801 A | 1/1999 | Southgate et al. |
| 5,925,533 A | 7/1999 | Doth et al. |
| 5,949,532 A | 9/1999 | Schrof et al. |
| 5,955,028 A | 9/1999 | Chow |
| 5,989,402 A | 11/1999 | Chow et al. |
| 5,999,250 A | 12/1999 | Hairston et al. |
| 6,033,628 A | 3/2000 | Kaltenbach et al. |
| 6,041,515 A | 3/2000 | Ally et al. |
| 6,049,380 A | 4/2000 | Goodwin et al. |
| 6,071,478 A | 6/2000 | Chow |
| 6,114,180 A | 9/2000 | Doth et al. |
| 6,130,101 A | 10/2000 | Mao et al. |
| 6,140,048 A | 10/2000 | Muller et al. |
| 6,177,277 B1 | 1/2001 | Soini |
| 6,208,815 B1 | 3/2001 | Seidel et al. |
| 6,211,955 B1 | 4/2001 | Basiji et al. |
| 6,242,266 B1 | 6/2001 | Schleifer et al. |
| 6,249,341 B1 | 6/2001 | Basiji et al. |
| 6,280,960 B1 | 8/2001 | Carr |
| 6,309,886 B1 | 10/2001 | Ambrose et al. |
| 6,338,746 B1 | 1/2002 | Detrick et al. |
| 6,355,420 B1 | 3/2002 | Chan |
| 6,386,219 B1 | 5/2002 | Barth et al. |
| 6,388,746 B1 | 5/2002 | Eriksson et al. |
| 6,394,305 B1 | 5/2002 | Sydlosky et al. |
| 6,403,338 B1 | 6/2002 | Knapp et al. |
| 6,403,947 B1 | 6/2002 | Hoyt et al. |
| 6,473,176 B2 | 10/2002 | Basiji et al. |
| 6,482,648 B2 | 11/2002 | Doth et al. |
| 6,495,104 B1 | 12/2002 | Unno et al. |
| 6,506,609 B1 | 1/2003 | Wada et al. |
| 6,532,067 B1 | 3/2003 | Chang et al. |
| 6,533,553 B2 | 3/2003 | Caren |
| 6,537,437 B1 | 3/2003 | Galambos et al. |
| 6,582,903 B1 | 6/2003 | Rigler et al. |
| 6,599,436 B1 | 7/2003 | Matzke et al. |
| 6,608,680 B2 | 8/2003 | Basiji et al. |
| 6,689,323 B2 | 2/2004 | Fisher et al. |
| 6,710,871 B1 | 3/2004 | Goix |
| 6,783,992 B2 | 8/2004 | Robotti et al. |
| 6,802,342 B2 | 10/2004 | Fernandes et al. |
| 6,811,668 B1 | 11/2004 | Berndt et al. |
| 6,816,257 B2 | 11/2004 | Goix |
| 6,918,404 B2 | 7/2005 | da Silva |
| 6,977,305 B2 | 12/2005 | Leung et al. |
| 6,991,907 B1 | 1/2006 | Buechler et al. |
| 7,066,586 B2 | 6/2006 | da Silva |
| 7,074,194 B2 | 7/2006 | Crosby |
| 2002/0030812 A1 | 3/2002 | Ortyn et al. |
| 2002/0123059 A1* | 9/2002 | Ho .................................. 435/6 |
| 2002/0167665 A1 | 11/2002 | Yeung et al. |
| 2003/0029995 A1 | 2/2003 | Mullins et al. |
| 2003/0078737 A1 | 4/2003 | Keys et al. |
| 2003/0109420 A1 | 6/2003 | Valkirs et al. |
| 2003/0124592 A1 | 7/2003 | Puskas et al. |
| 2003/2220077 | 12/2003 | Gu Ming et al. |
| 2004/0166514 A1 | 8/2004 | Puskas et al. |
| 2004/0214211 A1 | 10/2004 | Gilmanshin et al. |
| 2004/0219604 A1 | 11/2004 | Eriksson et al. |
| 2005/0164205 A1 | 7/2005 | Puskas |
| 2005/0221408 A1 | 10/2005 | Nalefski et al. |
| 2006/0003333 A1 | 1/2006 | Puskas |
| 2006/0004188 A1 | 1/2006 | Leung et al. |
| 2006/0078915 A1 | 4/2006 | Fuchs et al. |
| 2006/0078998 A1 | 4/2006 | Puskas et al. |
| 2006/0099638 A1 | 5/2006 | Leung et al. |
| 2006/0160209 A1 | 7/2006 | Larson et al. |
| 2006/0228747 A1 | 10/2006 | Fuchs et al. |
| 2008/0064113 A1 | 3/2008 | Goix et al. |
| 2008/0171352 A1 | 7/2008 | Goix et al. |
| 2008/0261242 A1 | 10/2008 | Goix et al. |
| 2010/0173321 A1 | 7/2010 | Hamm et al. |
| 2010/0255518 A1 | 10/2010 | Goix et al. |
| 2011/0111524 A1 | 5/2011 | Goix et al. |

FOREIGN PATENT DOCUMENTS

| | | |
|---|---|---|
| WO | WO 99/54497 A1 | 10/1999 |
| WO | WO 99/55461 A1 | 11/1999 |
| WO | WO 2004/059293 A2 | 7/2004 |
| WO | WO 2004/059293 A3 | 7/2004 |
| WO | WO 2005/089524 A2 | 9/2005 |
| WO | WO 2005/089524 A3 | 9/2005 |

OTHER PUBLICATIONS

Schulz et al. (American Heart Journal 2002 vol. 144, p. 351-358).*

Haab, et al., Single molecule florescence burst detection of DNA fragments separated by capillary electrophoresis., Anal Chem., 67:3523-3260 (1995).

Haab, et al., Single-molecule detection of DNA separations in microfabricated capillary electrophoresis chips employing focused molecular stream, Anal Chem., 71:5137-5145 (1999).

Haugland, Molelcular probes handbook of fluorescent probes and research product, Ninth Edition, Molecular Probes, Inc. (Table of Contents only) 2002.

Hubl, et al., Evaluation of the Architect Stat Troponin-I assay, Clinical Laboratory Publications, 51:251-255 (2005).

Huse, et al., Application of a filamentous phage pVII fusion protein system suitable for efficient production, screening and mutagenesis of f(ab) antibody fragments. J. Immunol. Dec. 15, 1992; 149 (12):39-14-20.

Katrukha, et al., Degradation of cardiac troponin I: implication for reliable immunodetection, Clinical Chemistry, 44:2433-2440 (1998).

Keller, et al., Analytical applications of single-molecule detection, Analytical Chemistry, 74:317A-324A (2002).

Kemp, et al., Biochemical markers of myocardial injury, British Journal of Anaesthesia, 93:63-73 (2004).

Klee, Human anti-mouse antibodies, Arch Pathol Lab Med. 124:921-3 (2000).

Koerbin, et al., The Comparative analytical performance of four troponin I assays at low concentration, Ann Clin. Biochem., 42:19-23 (2005).

Larue, et al., cardiac-Specific Immunoenzymaometric Assay of Troponin I in the Early phase of Acute Myocardial Infarction; Clinical Chemistry, 39:972-979 (1993).

LeCaptain, et al., Two-beam fluorescence cross-correlation spectroscopy in an electrophoretic mobility shift assay, Anal. Chem., 74:1171-1176 (2002).

Lexington Medical Center. Mycardial infarction redefined. NewsPath, May, 2001.

Li, et al. Ultrasensitive coincidence fluorescence detection of single DNA molecules, Anal. Chem., 75:1664-1670 (2003).

Loscher, et al., Counting of single protein molecules at interfaces and application of this technique in early-stage diagnosis, Anal. Chem, 70:3202-5 (1998).

Lucey, et al., Type 1 and type 2 cytokine dysregulation in human infectious, neoplastic and inflammatory diseases, Clinical Biology Reviews 9:532-562 (1996).

Ma, et al., single-molecule immunoassay and DNA diagnosis, Electrophoresis 22:421-426 (2001).

Mair Johannes: "Cardiac troponin I and Troponin T: Are enzymes still relevant as cardiac markers?" 1997 CLINICA CHIMICA ACTA, vol. 257, NR. 1, p. 99-115.

Nalefski, et al., Single-molecule counting of macromolecular complexes in real time: a novel approach to quantify transcription factor—DNA and antibody-antigen interactions. Faseb Journal 2004; 18(8):c176.

Nguyen, et al., Detection of single molecules of phycoerythrin in hydrodynamically focused flows by laser-induced fluorescence, Anal. Chem., 59:2158-2161 (1987).

Oh, et al. Use of a dual monoclonal solid phase and a polyclonal detector to create an immunoassay for the detection of human cardiac troponin I, Clin. Biochem., 33:255-262 (2000.).

Ohman, et al., Cardiac troponin T levels for risk stratification in acute mycardial ischemia, The New England Journal of Medicine, 335:1333-1341 (1997).

Panchuk-Voloshina, et al., Alexa dyes a series of new fluorescent dyes that yield exceptionally bright, photostable conjugates. J. Histochem Cytochem, Sep. 1999; 47(9) 1179-88.

Panteghini, et al., Evaluation of imprecision for cardiac troponin assays at low range concentrations, Clinical Chemistry, 50:327-332 (2004).

Panteghini, Role and importance of biochemical markers in clinical cardiology, European Heart Journal, 25:1187-1196 (2004).

Panteghini, The interfering component in cardiac troponin I immunoassays: need for further experimental evidence., Clin chem, 2004; 50:676-677 (2004).

Park, Addressing Unmet Needs in Assay Development. Medical Device Link Mar. 1-4, 2007.

Peck, et al., Single-molecule fluorescence detection: autocorrelation criterion and experimental realization with phycoerythrim, Proc. Natl. Acad. Sci. USA, 86:4087-4091 (1989).

Phillips, et al., Application of single molecule technology to rapidly map long DNA and study the conformation of stretched DNA., Nucleic Acids Res. 33:5829-37 (2005).

Poster presented at Oak Ridge Conference. Development and preliminary clinical validation of a high sensitivity assay for cardiac tropoin using a capillary flow (single molecule) fluorescence detector, Apr. 21-22, 2006, San Jose, CA.

Sato, et al., biochemical markers of myocyte injury in heart failure, Heart (British Cardiac Society), 90:1110-1113 (2004).

Sauer, et al., Detection and identification of individual antigen molecules in human serum with pulsed semiconductor lasers, Appl. Phys. B., 65:427-431 (1997).

Shera, et al., Detection of single fluorescent molecules, Chemical Physics Letters, 174:553-557 (1990).

Shortreed, et al., High-throughput single—molecule DNA screening based on electrophoresis, Anal. Chem., 72:2879-2885 (2000).

Sidransky, Emerging molecular markers of cancer, Nature Reviews: Cancer. 2:210-219 (2002).

Soper, et al., Photon burst detection of single near-infrared fluorescent molecules, Anal. Chem., 65:740-747 (1993).

Soper, et al., Single-molecule detection in the near-IR using continuous wave diode laser excitation with an avalanche photon detector, Applied Spectroscopy 52:1-6 (1998).

Stiegler, et al., Lower cardiac tropoinin T and I results in heparin-plasma than in serum, Clinical Chemistry, 46:1338-1344 (2000).

Tanaka, et al., Protein and polymer analyses up to m/z 100 000 by laser ionization time-of-flight mass spectrometry, Rapid Commun. Mass. Spect. 2:151-153 (1988).

Thomas Ma et al.: "A review of troponin assay performance in Wales: can the same (Method-dependent decision limits be used in different sites?" Annals of Clinical biochemistry, British Medical Association, London, GB, vol. 42, No. 5, Sep. 1, 2005, pp. 351-356.

Todd et al. Ultrasensitive flow-based mmunoassyas using single-molecule counting. Clin. Chem. Nov. 2007; 53 (11): 1990-1095.

Upatnieks, et al., A kilohertz frame rate cinemagraphic PIV system for laboratory-scale turbulent and unsteady flows, Experiments in Fluids 32:87-98 (2002).

Van Orden, et al., Single-molecule identification in flowing sample streams by fluorescence burst size in intraburst fluorescence decay rate, Anal. Chem., 70:1444-1451 (1998).

Wabuyele, et al., Single molecule detection of double-stranded DNA in poly(methylmethacrylate) and polycarbonate microfluidic devices, Electrophoresis, 22:3939-3948 (2001).

Wallace, et al., Serum Troponins as Biomarkers of Drug-Induced Cardiac Toxicity, Toxicologic Pathology, 32:106-121 (2004).

Willneff, a spatio-temporal matching algorithm for 3D particle tracking velocimetry: a dissertation submitted to the Swwiss Federal Institute of Technology Zurich for the degree of Doctroal of Technical sciences (abstract), Sep. 2003, Diss. Eth No. 15276. Available at http://e-collection.ethbib.ethz.ch/ecol-pool/diss/abstracts/p15276.pdf.

Wu, et al., Development and Preliminary clinical validation of a high Sensitivity Assay for Cardiac Tropoin using a Capillary Flow (Single Molecule) Fluorescence detector, Clinical Chemistry 52:2157-2159 (2006).

Wu, et al., National academy of clinical biochemistry standards of laboratory practice: recommendations for the use of cardiac markers in coronary artery diseases, Clinical Chemistry, 45:1104-1121 (1999).

Young, Singles Developing Troponin Test for earlier detection of AMI, Medical Device Daily, Dec. 13, 2006.

Zethelius, et al. Troponin I as a predictor of coronary heart disease and morality in 70-year-old mend: a community-based cohort study. Circulation Feb. 28, 2006; 113 (8): 1071-1078.

Achar, et al. Diagnosis of acute coronary syndrome. American Family Physician, 72:119-126 (2005).

Adams, et al. Cardiac troponin I.A. marker with high specificity for cardiac injury, Circulation, 88:101-106 (1993).

Adams, et al., Comparable detection of acute myocardial infarction by creatine kinase MB isoenzyme and cardiac troponin I., Clinical Chemistry, 40:1291-1295 (1994).

Alexa Flour Dyes, Succinimidyl Esters. Revised Jan. 4, 2006; 1-5.

Alexa Fluor Dyes Handbook. Simply the Best and Brightest: Fluorescent Dyes and Conjugates. Invitrogen. Copyright 2005. Molecular Probes. 1-33.

Ambrose, et al. Single molecule fluorescence spectroscopy at ambient temperature. Chemical Reviews, 99:2929-56 (1999).

Anazawa, et al. Electrophoretic quantitation of nucleic acids without amplification by single molecule imaging, Anal. Chem, 74:5033-38 (2002).

Antman, et al., Cardiac-specific troponin I levels to predict the risk of mortality in patients with acute coronary syndromes, The New England Journal of Medicine, 335:1342-1349 (1996).

Apple, et al. Validation of the 99th Percentile Cutoff Independent of Assay lmprecsion (CV) for Cardiac Troponin Monitoring for Ruling Out Myocardial Infarction, Clinical Chemistry, 51, No. 11, Nov. 2005, pp. 2198-2200.

Apple, et al., The diagnostic utility of cardiac biomarkers in detecting myocardial infarction, Clinical Cornerstone, 7: S25-30 (2005).

Babuin, et al., Troponin:the biomarker of choice for the detection of cardiac injury, Canadian medical Association Journal, 173:1191-1202 (2005).

Becker, et al., Three-dimensional photogrammetric particle-tracking velocimetry, Preparing for the Future, 5(3)(1995); available at http://esapub.esrin.esa.it/pffv5n3/beckv5nc.htm(7 pages).

Bieschke, et al., Ultrasensitive detection of pathological prion protein aggregates by dual-color scanning for intensely fluorescent targets, Pro. Natl. Acad. Sci., 97:5468-5473 (2000).

Borrebaeck, C., Editor. Antibody Engineering. Second Edition. 1995 Oxford University Press, Oxford.

Bouchon, et al. Cutting edge: inflammatory responses can be triggered by TREM-1, a novel receptor expressed on neutrophils and monocytes, The Journal of Immunology, 164:4991-4995 (2000).

Braunwald, et al, ACC/AHA 2002 guideline update for the management of patients with unstable angina and non-ST-segment elevation mycardial infarction—A report of the American College of Cardiology/American Heart Association task force on practice guidelines (Committee on the Management of Patients with Unstable Angina), American College of Cariology and the American Heart Association (2002).

Brinkmeier, et al., Two-beam cross-correlation: a method to characterize transport phenomena in micrometer-sized structures, Anal. Chem., 71:609-616 (1999).

Buisson, et al., Biochemical markers of mycardial injury, Available at http://ww.ampath.co.za/Documents/ biochemicalMarkers.pdf. Accessed Sep. 20, 2007.

Castro, et al. Fluorescence detection and size measurement of single DNA molecules, Anal. Chem., 65:849-852 (1993).

Castro, et al. Single-molecule detection of specific nucleic acid sequences in unamplified genomic DNA, Anal. Chem., 69:3915-3920 (1997).

Castro, et al., single molecule detection: applications to ultrasensitive biochemical analysis, Applied Optics, 34:3218-3222 (1995).

Castro, et al., Single-molecule electrophoresis, Anal. Chem., 67:3181-3186 (1995).

Castro, et al., Ultrasensitive, direct detection of a specific DNA sequence of *Bacillus antracis* in solution, The Analyst 125:9-11 (2000).

Cayley, Diagnosing the cause of chest pain, American Family Physician, 72:2012-2021 (2005).

Chan, et al,. DNA mapping using microfluidic stretching and single-molecule detection of fluorescent site-specific tags, Genome Res. 14:1137-46 (2004).

Chen, et al., Single-molecule detection in capillary electrophoresis: molecular shot noise as a fundamental limit to chemical analysis, Anal. Chem., 68:690-696 (1996).

Cohen, et al., Rapid separation and purification of oligonucleotides by high performance capillary gel electrophoresis, Proc. Natl. Acad. Sci., 85:9660-9663 (1988).

Colonna, TREMSs in the immune system and beyond, Nature Reviews: Immunology 3:445-453 (2003).

Csiro Australia, Image motion, tracking and registration. Available at http://www.cmis.csiro.au/IAP/Motion. Accessed Jan. 24, 2005.

D'Antoni, et al., Rapid quantitative analysis using a single molecule counting, Anal. Chem., 352:97-109 (2006).

Diderholm, et al, The prognostic and therapeutic implications of increased troponin T levels and ST depression in unstable coronary artery disease: the FRISC II invasive tropoinin T electrocardiogram substudy, Am. Heart J., 143:760-767 (2002).

Dovichi, et al., Laser-induced fluorescence of flowing samples as an approach to single-molecule detection in liquids. Anal. Chem., 56:348-354 (1984).

Dunbar, et al., Quantitative multiplexed detection of bacterial pathogens: DNA and protein applications of Luminex LabMap system, J. Microbiol Methods. 2003; 53(2): 245-252.

Effenhauser, et al, Integrated capillary electrophoresis on flexible silicone microdevices: analysis of DNA restriction fragments and detection of single DNA molecules on microchips, Anal. Chem., 69:3451-3457 (1997).

Eryol, et al., Should Troponin-T Be Assessed During Exercise Stress Testing in Patients with Stable Angina Pectoris? Anadolu Kardiyol Der., 2:132-137 (2002).

Etzioni, et al., the case for early detection, Nature Reviews: Cancer 3:243-252 (2003).

Ferrieres, et al., Human cardiac troponin I: precise identification of antigenic epitopes and prediction of secondary structure, Clinical Chemistry 44:487-493 (1998).

Fister, et al. Counting single chromphore molecules for ultrasensitive analysis and separations on microchip devices, Anal. Chem., 70:431-437 (1998).

Gaze, et al., Cardiac Troponins as Biomarkers of Drug and Toxin Induced Cardiac Toxicity and Cardioprotection, Expert Opin. Drug Metabl. toxicol. 1:715-725 (2005).

Giannitsis, et al., Admission tropoinin T level predicts clinical outcomes, TIMI flow, and mycardial tissue perfusion after primary percutaneous intervention for acute ST-segment elevation mycoardial infarction, Circulation, 104:630-635 (2001).

Gibot, et al., Plasma level of a triggering receptor expressed on myeloid cells-1: its diagnostic accuracy in patients with suspected sepsis, Annals of Internal Medicine, 141:9-15 (2004).

Gibot, et al., soluble triggering receptor expressed on muyeloid cells and the diagnosis of pneumonia, The New england Journal of Medicine, 350:451-458 (2004).

Glenn Research Center, NASA, particle Imaging Velocimetry. Available at http://www.grc.nasa.gov/www/Optlinstr/piv/ background. htm and associated web pages. Accessed Jan. 26, 2005.

Goix, Fulfilling the promise of biomarkers in drug discovery and development, Drug Discovery + International, 6-7, Apr./May 2007.

Goix, Single Molecule "Flow immunoassay" detection: Repurposing existing marker for clinical validation. Slides from presentation at clinical biomarkers summit, Coronado, CA, Mar. 29-31, 2006.

Golde, Alzheimer disease therapy: can the amyloid cascade be halted?, The Journal of Clinical Investigation, 11:11-18 (2003).

Guenard, et al., Two-channel sequential single-molecule measurement, Anal. Chem., 69:2426-2433 (1997).

Guide to Alexa Flour Succinimidyl Esters. Revised Jan. 4, 2006.

Guide to Amine-Reactive Probes., Reviese Oct. 13, 2005.

Guide to Labeling Antibodies with Alexa Fluor Dyes, 24-28 (2004).

Zhu, et al., Fluorescence multiplexing with time-resolved and spectral discrimination using a near-IR detector, Anal. Chem, 75:2280-2291 (2003).

Office Action for U.S. Appl. No. 11/784,213 mailed Jan. 20, 2011.

Zhu, et al., Fluorescence multiplexing with time-resolved and spectral discrimination using a near-IR detector., Anal. Chem., 2003, 75:2280-2291.

Office Action mailed Oct. 4, 2011 for U.S. Appl. No. 11/784,213, filed Apr. 4, 2007.

Office Action for U.S. Appl. No. 11/784,213 mailed Feb. 27, 2012.

Office Action for U.S. Appl. No. 11/784,213 mailed on Feb. 27, 2012.

Office Action for U.S. Appl. No. 11/784,213 mailed on Aug. 29, 2012.

LaRue, et al., New Monoclonal Antibodies as Probes for Human Cardiac Troponin I: Epitopic Analysis with Synthetic Peptides, Molecular Immunology, 29:271-278 (1992).

Bertinchant, et al., Evaluation of cardiac troponin I and T levels as markers of mycardial damage in doxorubicin-induced cardiomyopathy rats, and their relationship with echocardiographic and histological findings, clinica Chimica Acta 239:39-51 (2003).

Strongin, Wendy, Sensitivity, Specificity, and Predictive Value of Diagnostic Tests: Definitions and Clinical Applications, Lennette, ed. Marcel Dekker, Inc., New York, pp. 212-219 (1992).

Dittrich, et al., Single-molecule fluorescence detection in microfluidic channels-the Holy Grain in μTAS, Analytical and Bioanalytical Chemistry, 382:1771-1782 (2005).

O'Regan, et al., Development of Biosensor Array for Rapid Detection of Cardiac Markers: Immunosensor for Detection of Free Cardiac Troponin I, Analytical Letters, 36:1903-1920 (2003).

Ishii, et al., Communication between troponin-C and -I revealed by single molecular fluorescence spectroscopy and FRET, Biophysical Journal, 72:A283 (1997).

Mingels, High-sensitivity cardiac troponin assays, PhD thesis, University Maastricht, 1-192 (2012).

* cited by examiner

Species cross-reactivity and sensitivity achieved

| Species standard from HyTest diluted into species serum | Background | Slope | LOD pg/ml |
|---|---|---|---|
| Human standard | 143 | 138 | 0.19 |
| Monkey standard | 147 | 28 | 0.72 |
| Dog standard | 138 | 68 | 0.58 |
| Rat standard | 138 | 84 | 0.14 |

LoD = 2 X std Dev background signal/slope

LoD 10% = LoD but assumes 10% CV on background signal

FIG. 9

Endogenous serum levels in different species

| Species | cTnI pg/ml |
|---|---|
| Rat | 9.5 |
| Dog | 4.6 |
| Monkey male | 5.3 |
| Monkey female | 4.4 |
| Human | 0.5-9 |

FIG. 10

HIGHLY SENSITIVE SYSTEM AND METHOD FOR ANALYSIS OF TROPONIN

CROSS REFERENCE

This application claims priority under 35 U.S.C. §119 to U.S. Provisional Application 60/914,995, filed Apr. 30, 2007, and U.S. Provisional Application 60/925,402, filed Apr. 19, 2007. This application is a continuation of U.S. patent application Ser. No. 12/062,412, filed Apr. 3, 2008, now U.S. Pat. No. 7,838,250, which is a continuation-in-part of U.S. patent application Ser. No. 11/784,213, filed Apr. 4, 2007, which claims the benefit of U.S. Provisional Application No. 60/789,304, filed Apr. 4, 2006, U.S. Provisional Application No. 60/793,664, filed Apr. 19, 2006, and U.S. provisional Application No. 60/808,622, filed May 26, 2006, U.S. Provisional Application No. 60/861,498, filed Nov. 28, 2006, and U.S. Provisional Application No. 60/872,986, filed Dec. 4, 2006. U.S. Provisional Application 60/914,995, U.S. Provisional Application 60/925,402, U.S. Provisional Application No. 60/789,304, U.S. Provisional Application No. 60/861,498, and U.S. Provisional Application No. 60/872,986, are incorporated herein by reference in their entirety.

BACKGROUND OF THE INVENTION

Each year in the United States, some six million people present to emergency departments with chest pain. Although only 15% to 20% of these patients are ultimately diagnosed with an acute coronary syndrome (ACS), about half are admitted for evaluation. Conversely, 2% of patients with ACS are mistakenly discharged. As patients with ACS have a relatively high risk of major adverse cardiovascular events in the short term, there is a clear need for accurate objective tools by which to identify them.

Currently used markers for cardiac damage suffer disadvantages that limit their clinical usefulness. Cardiac enzyme assays have formed the basis for determining whether or not there is damage to the cardiac muscle. Unfortunately, the standard creatine kinase-MB (CK-MB) assay is not reliable in excluding infarction until 10 to 12 hours after the onset of chest pain. Earlier diagnosis would have very specific advantages with regard to fibrinolytic therapy and triage. In additional, more sensitive markers of cardiac toxicity would allow earlier detection of adverse effects of, e.g., drug therapy.

SUMMARY OF THE INVENTION

In one aspect the invention provides methods.

In some embodiments, the invention provides a method for determining the presence or absence of a single molecule of troponin or a fragment or complex thereof in a sample, including i) labeling the molecule, fragment, or complex, if present, with a label; and ii) detecting the presence or absence of the label, where the detection of the presence of the label indicates the presence of the single molecule, fragment, or complex of troponin in the sample. In some embodiments of the methods of the invention, the troponin is a cardiac isoform of troponin. In some embodiments of the methods of the invention, the troponin can be cardiac troponin I (cTnI) or cardiac troponin C (cTnC). In some embodiments of the methods of the invention, the troponin is cTnI. In some embodiments of the methods of the invention, a single molecule of troponin can be detected at a limit of detection of less than about 100 pg/ml. In some embodiments of the methods of the invention, a single molecule or troponin can be detected at a level of detection of less than about 20 pg/ml. In some embodiments of the methods of the invention, the label includes a fluorescent moiety. In some embodiments, the fluorescent moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules. In some embodiments of the methods of the invention, the fluorescent moiety includes a molecule that contains at least one substituted indolium ring system in which the substituent on the 3-carbon of the indolium ring contains a chemically reactive group or a conjugated substance group. In some embodiments of the methods of the invention, the fluorescent moiety includes a dye. Examples of dyes include, but are not limited to, AlexaFluor 488, AlexaFluor 532, AlexaFluor 647, AlexaFluor 680 and AlexaFluor 700. In some embodiments of the methods of the invention, the fluorescent moiety includes AlexaFluor 647. In some embodiments, the fluorescent moiety includes a molecule that contains at least one substituted indolium ring system in which the substituent on the 3-carbon of the indolium ring contains a chemically reactive group or a conjugated substance group. In some embodiments of the methods of the invention, the label further includes a binding partner for the troponin molecule, fragment, or complex. In some embodiments of the methods of the invention, the binding partner includes an antibody specific to the troponin molecule, fragment, or complex. In some embodiments of the methods of the invention, the antibody is specific to a specific region of the troponin molecule. In some embodiments of the methods of the invention, the antibody is specific to a region comprising amino acids 27-41 of cardiac troponin I. In some embodiments of the methods of the invention, the antibody can be a polyclonal antibody. In some embodiments of the methods of the invention, the antibody is a monoclonal antibody. In some embodiments of the methods of the invention, the methods further include capturing troponin or troponin complex on a solid support. In some embodiments of the methods of the invention, the solid support can be a microtiter plate or paramagnetic beads. In some embodiments of the methods of the invention, the solid support includes a capture partner specific for the troponin or troponin complex that is attached to the solid support. In some embodiments of the methods of the invention, the attachment of the capture partner to the solid support is noncovalent. In some embodiments of the methods of the invention, the attachment of the capture partner to the solid support is covalent. In some embodiments of the methods of the invention, the covalent attachment of the capture partner is such that the capture partner is attached to the solid support in a specific orientation. In some embodiments of the methods of the invention, the specific orientation serves to maximize specific binding of the troponin or troponin complex to the capture partner. In some embodiments of the methods of the invention, the capture partner comprises an antibody. In some embodiments of the methods of the invention, the antibody is a monoclonal antibody. In some embodiments of the methods of the invention, antibody is specific to amino acids 87-91 of cardiac troponin I. In some embodiments of the methods of the invention, the antibody is specific to amino acids 41-49 of cardiac troponin I. In some embodiments of the methods of the invention, the sample is a blood, serum, or plasma sample. In some embodiments of the methods of the invention, the sample is a serum sample. In some embodiments of the methods of the invention, the label include a fluorescent moiety, and step ii) includes passing the label through a single molecule detector. In some embodiments of the methods of the invention, the single molecule detector include: a) an electromagnetic radiation source for stimulating the fluorescent moiety; b) a capillary flow cell for passing the fluorescent moiety; c) a source of motive force for moving the fluorescent moiety in the capillary flow cell; d) an interrogation space defined within the capillary flow cell for receiving electromagnetic radiation emitted from the electromagnetic source; e) an electromagnetic radiation detector operably connected to the interrogation space for measuring an electromagnetic characteristic of the stimulated fluorescent moiety; and f) a microscope objective lens situated between the interrogation space and the detector, where the lens is a high numerical aperture lens.

In some embodiments, the invention provides a method for determining a diagnosis, prognosis, or method of treatment in an individual that includes: i) determining a concentration of cardiac troponin in a sample or determining the concentrations of cardiac troponin in a series of samples from the individual, where the concentration is determined by a cardiac troponin assay with a limit of detection for the cardiac troponin in the sample of less than about 50 pg/ml; and ii) determining a diagnosis, prognosis, or method of treatment in the individual, based on the concentration in the sample, or on the concentrations in the series of samples. In some embodiments of the methods of the invention, step ii) includes an analysis such as comparing the concentration or series of concentrations to a normal value for the concentration, comparing the concentration or series of concentrations to a predetermined threshold level, comparing the concentration or series of concentrations to a baseline value, and determining a rate of change of concentration for the series of concentrations. In some embodiments of the methods of the invention, step ii) includes comparing the concentration of troponin in the sample with a predetermined threshold concentration, and determining a diagnosis, prognosis, or method of treatment if the sample concentration is greater than the threshold level. In some embodiments of the methods of the invention, the threshold concentration is determined by determining a the 99th percentile concentration of troponin in a group of normal individuals, and setting the threshold concentration at the 99th percentile concentration. In some embodiments of the methods of the invention, at least one sample is taken during or after a cardiac stress test. In some embodiments of the methods of the invention, the cardiac troponin is selected from the group consisting of cardiac troponin I and cardiac troponin T. In some embodiments of the methods of the invention, the cardiac troponin is cardiac troponin I. In some embodiments of the methods of the invention, the concentration of cardiac troponin is a concentration of total cardiac troponin. In some embodiments of the methods of the invention, the concentration of cardiac troponin is a concentration of a cardiac troponin complex, cardiac troponin fragment, phosphorylated cardiac troponin, oxidized cardiac troponin, or a combination thereof. In some embodiments of the methods of the invention, the concentration of cardiac troponin is compared to total cardiac troponin. In some embodiments of the methods of the invention, the diagnosis, prognosis, or method of treatment is a diagnosis, prognosis, or method of treatment of myocardial infarct. In some embodiments of the methods of the invention, the diagnosis, prognosis, or method of treatment comprises risk stratification for level of risk of myocardial infarct. In some embodiments of the methods of the invention, the concentration or series of concentrations is determined at or near the time the individual presents to a health professional with one or more symptoms indicative of myocardial ischemia or infarct or the possibility thereof. In some embodiments, the one or more symptoms can be chest pain, chest pressure, arm pain, abnormal EKG, abnormal enzyme levels, or shortness of breath. In some embodiments, the concentration is determined by a method that includes detecting single molecules of troponin, or complexes or fragments thereof. In some embodiments, the methods of the invention involve labeling troponin or a troponin complex with a label that comprises a fluorescent moiety. In some embodiments of the methods of the invention, the fluorescent moiety is capable of emitting at least about 200 photons when simulated by a laser emitting light at the excitation wavelength of the moiety, where the laser is focused on a spot 5 microns in diameter that contains the moiety, and where the total energy directed at the spot by the laser is no more than about 3 microJoules. In some embodiments of the methods of the invention, the fluorescent moiety includes a molecule that contains at least one substituted indolium ring system in which the substituent on the 3-carbon of the indolium ring contains a chemically reactive group or a conjugated substance group. In some embodiments of the methods of the invention, the fluorescent moiety includes a dye selected from the group consisting of AlexaFluor 488, AlexaFluor 532, AlexaFluor 647, AlexaFluor 680 or AlexaFluor 700. In some embodiments of the methods of the invention, the fluorescent moiety comprises AlexaFluor 647. In some embodiments of the methods of the invention, the label further comprises a binding partner for the troponin. In some embodiments, the binding partner comprises an antibody specific to the troponin. In some embodiments, the antibody is a polyclonal antibody. In some embodiments of the methods of the invention, the methods further include capturing troponin or troponin complex on a solid support. In some embodiments of the methods of the invention, the solid support can be a microtiter plate or paramagnetic beads. In some embodiments of the methods of the invention, the solid support includes a capture partner specific for the troponin or troponin complex that is attached to the solid support. In some embodiments of the methods of the invention, the attachment of the capture partner to the solid support is noncovalent. In some embodiments of the methods of the invention, the attachment of the capture partner to the solid support is covalent. In some embodiments of the methods of the invention, the covalent attachment of the capture partner is such that the capture partner is attached to the solid support in a specific orientation. In some embodiments of the methods of the invention, the specific orientation serves to maximize specific binding of the troponin or troponin complex to the capture partner. In some embodiments of the methods of the invention, step i) further involves assessing another indicator for the individual, and step ii) involves determining a diagnosis, prognosis, or method of treatment in the individual, based on the concentration of troponin and the assessment of the other indicator of the non-troponin marker in the sample, or on the concentrations in the series of samples. In some embodiments, the other indicator is a clinical indicator of myocardial ischemia or infarct. In some embodiments, the other indicator is the concentration of one or more non-troponin markers in the sample or the series of samples. In some embodiments of the methods of the invention, the one or more markers are markers of cardiac ischemia, or markers of inflammation and of plaque instability. In some embodiments, the one or more markers of cardiac ischemia can be creatine kinase (CK) and its myocardial fraction CK myocardial band (MB), aspartate aminotransferase, lactate dehydrogenase (LDH), α-hydroxybutyrate dehaydrogenase, myoglobin, glutamate oxaloacetate transaminase, glycogen phosphorylase BB, unbound free fatty acids, heart fatty acid binding protein (H-FABP), ischemia-modified albumin, myosin light chain 1, or myosin light chain 2. In some embodiments of the methods of the invention, the one or more markers include one or more specific markers of myocardial injury. In some embodiments of the methods of the invention, the diagnosis, prognosis, or method of treatment is a diagnosis, prognosis, or method of treatment of a condition that is not myocardial infarct. In some embodiments, the condition is cardiac toxicity. In some embodiments, the cardiac toxicity is associated with the administration of a drug to the individual. In some embodiments of the methods of the invention, the condition is selected from the group consisting of acute rheumatic fever, amyloidosis, cardiac trauma (including contusion, ablation, pacing, firing, cardioversion, catheterization and cardiac surgery), reperfusion injury, congestive heart failure, end-stage renal failure, glycogen storage disease type II (Pompe's disease), heart transplantation, haeomoglobinopathy with transfusion haemosiderosis, hypertension, including gestational hypertension, hypotension, often with arrhythmias, hypothyroidism, myocarditis, pericarditis, post-operative non-cardiac surgery, pulmonary embolism, and sepsis.

In some embodiments, provided is a method of classifying an individual having one or more symptoms of cardiac infarct comprising: i) obtaining a sample from said individual, ii) detecting the level of troponin in the sample and iii) if the level of troponin is above 10-fold of the 99th percentile, taking a first action with respect to the individual and if the level of troponin is below 10-fold of the 99th percentile taking a second action. In some embodiments, the first action is taken if patient has about a 3-fold to about a 10-fold increase relative to the 99th percentile cutoff. In some embodiments, the first action is taken if patient has about a 4-fold to about a 5-fold increase relative to the 99th percentile cutoff. In some embodiments, the first action is taken if patient has about a 6-fold to about a 7-fold increase relative to the 99th percentile cutoff. In some embodiments, the first action is taken if patient has about an 8-fold to about a 10-fold increase relative to the 99th percentile cutoff. In some embodiments, the first action is taken if patient has about a 1.5-fold to about a 2-fold increase. In some embodiments, the first action is taken if patient has about a 2-fold to about a 2.5-fold increase. In some embodiments, the first action is taken if patient has about a 2.5-fold to about a 3-fold increase. In some embodiments, the first action is taken if patient has about a 3-fold to about a 3.5-fold increase. In some embodiments, the first action is taken if patient has about a 3.5-fold to about a 4-fold increase. In some embodiments, the first action is taken if patient has about a 4-fold to about a 4.5-fold increase. In some embodiments, the first action is taken if patient has about a 4.5-fold to about a 5-fold increase. In some embodiments, the first action is taken if patient has about a 5-fold to about a 5.5-fold increase. In some embodiments, the first action is taken if patient has about a 5.5-fold to about a 6-fold increase. In some embodiments, the first action is taken if patient has about a 6-fold to about a 6.5-fold increase. In some embodiments, the first action is taken if patient has about a 6.5-fold to about a 7-fold increase. In some embodiments, the first action is taken if patient has about a 7-fold to about a 7.5-fold increase. In some embodiments, the first action is taken if patient has about a 7.5-fold to about an 8-fold increase. In some embodiments, the first action is taken if patient has about a 8-fold to about a 8.5-fold increase. In some embodiments, the first action is taken if patient has about an 8.5-fold to about a 9-fold increase. In some embodiments, the first action is taken if patient has about a 9-fold to about a 9.5-fold increase. In some embodiments, the first action is taken if patient has about a 9.5-fold to about a 10-fold increase. In some embodiments the first action is taken if the increase is more than about 2-fold. In some embodiments the first action is taken if the increase is more than about 3-fold. In some embodiments the first action is taken if the increase is more than about 4-fold. In some embodiments the first action is taken if the increase is more than about 5-fold. In some embodiments the first action is taken if the increase is more than about 6-fold. In some embodiments the first action is taken if the increase is more than about 7-fold. In some embodiments the first action is taken if the increase is more than about 8-fold. In some embodiments the first action is taken if the increase is more than about 9-fold. In some embodiments the first action is taken if the increase is more than about 10-fold.

In some embodiments, the individual is a patient being evaluated for a possible cardiac event. In such a case, the first action can be admission of the individual to a hospital, or other appropriate clinical action for treatment of the cardiac event. The second action can be to hold the individual for a period of time for further observation. During the time the individual is held a series of samples are taken from said patient and the level of troponin in each sample detected. In some embodiments, the interval between samples is less than about 4, 3, 2, 1, 0.5 hours apart. In some embodiments, the sample interval is less than about 4 hours apart. In some embodiments, the sample interval is about 1 hour. In some embodiments, the sample interval is about 2 hours. It will be recognized that circumstances in the clinic dictate sample intervals and some degree of variation is acceptable and is encompassed within the invention, as long as results may be reliably interpreted. In some embodiments, in addition to the level of troponin detected in each sample, the rate of change in the level of troponin over two or more samples in the series of samples is detected. In some embodiments, the change in the level of troponin is a decrease. In some embodiments, the change in the level of troponin is an increase. A decision can be made regarding a course of action for said individual based on said rate of change, e.g., if the rate of change in troponin values exceeds a predetermined upper reference rate of change value, the decision is to admit the individual. It will be recognized that other clinical factors well-known to those of skill in the art can be used to modify the decision based on troponin levels, e.g., if other clinical manifestations of acute myocardial infarct are present, such as abnormal EKG, abnormal enzyme levels, physical symptoms, and the like, then the threshold for troponin that leads to an admission is suitably decreased. The decision to take a first action, e.g., to admit a patient, can also be made if one or more spikes in the level of troponin are seen from sample to sample. The spike can be any increase in the level of troponin detected compared to one or more samples wherein the increase is compared to a threshold level. For example, if the threshold level is determined to be 10 pg/ml and if in one of the sample of the series of samples the troponin level detected is 15 pg/ml, the patient is admitted. In some embodiments, the threshold level is determined from a reference population. In some embodiments, the threshold level is set at a level for an individual, e.g., the initial level of troponin detected from the first sample taken from the patient. In these embodiments, a relative increase indicates a spike, no matter what the absolute values are. In some embodiments, a spike is determined when the troponin level increases 2, 3, 4, 5, 6, 7, 8, 9 10, or more than 10-fold above a reference value for the individual, e.g., a value set at the troponin level in the first sample taken from the individual. Alternatively, a spike in the level of troponin can be seen when comparing troponin levels between samples from the individual. In such a case, no matter what the value of the level of troponin detected, the patient is admitted if the value increases by more than a certain amount, e.g., a patient is admitted when the level of troponin increases by 1, 2, 3, 4, 5, 6, 7, 8, 9, 10, or more than 10 pg/ml as compared to one or more neighboring samples. In some embodiments, the change in the level of troponin indicates an acute cardiovascular disease. In some embodiments, the change in the level of troponin indicates a chronic cardiovascular disease. In some embodiments, the change in the level of troponin indicates cardiotoxicity.

In another aspect the invention includes compositions.

In some embodiments the invention includes a composition for the detection of a troponin isoform including a binding partner to the troponin isoform attached to a fluorescent moiety, where the fluorescent moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules. In some embodiments of the compositions of the invention, the binding partner comprises an antibody to the troponin isoform. In some embodiments, the antibody is a polyclonal antibody. In some embodiments, the antibody is a monoclonal antibody. In some embodiments, the troponin isoform is a cardiac isoform. In some embodiments, the cardiac isoform is selected from the group consisting of cTnI and cTnT. In some embodiments, the cardiac isoform is cTnI. In some embodiments, the antibody is specific to a specific region of the troponin molecule. In some embodiments, the antibody is specific to a region comprising amino acids 27-41 of cardiac troponin I. In some embodiments of the compositions of the invention, the fluorescent moiety comprises a molecule that comprises at least one substituted indolium ring system in which the substituent on the 3-carbon of the indolium ring contains a chemically reactive group or a conjugated substance group. In some embodiments, the fluorescent moiety includes a dye that can be AlexaFluor 488, AlexaFluor 532, AlexaFluor 647, AlexaFluor 680 or AlexaFluor 700. In some embodiments, the fluorescent moiety comprises AlexaFluor 647.

In some embodiments the invention involves a composition comprising a set of standards for the determination of a concentration of a cardiac troponin, where at least one of the standards is at a concentration of cardiac troponin less than about 10 pg/ml.

In another embodiment, provided herein is a composition comprising a label for cardiac troponin comprising a detection binding partner for cardiac troponin I, wherein the detection binding partner is capable of cross-reacting with cardiac troponin I from at least two species, and a fluorescent moiety, wherein said moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the detection binding partner is capable of reacting with cardiac troponin I from at least two species selected from the group consisting of human, monkey, dog, and rat. In some embodiments, the detection binding partner is capable of reacting with cardiac troponin I from human, monkey, dog, and rat. The detection binding partner can be an antibody. In some embodiments, the composition further comprises a capture binding partner for cardiac troponin I, wherein the capture binding partner is capable of cross-reacting with cardiac troponin I from at least two species. The capture binding partner can be capable of reacting with cardiac troponin I from at least two species selected from the group consisting of human, monkey, dog, and rat. In some embodiments, the capture binding partner is capable of reacting with cardiac troponin I from human, monkey, dog, and rat. In some embodiments the capture binding partner is an antibody.

In some embodiments the invention involves a kit containing a composition including an antibody to cardiac troponin attached to a fluorescent dye moiety, where the moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules, where the composition is packaged in suitable packaging. In some embodiments of the kits of the invention, the cardiac troponin is cardiac troponin I or cardiac troponin T. In some embodiments, the cardiac troponin is cardiac troponin I. In some embodiments of the kits of the invention, the kits further include instructions. In some embodiments of the kits of the invention, the kits further include a composition containing a capture antibody for the cardiac troponin I attached to a solid support. In some embodiments, the solid support comprises a microtiter plate or paramagnetic microparticles. In some embodiments of the kits of the invention, the kits further include a component selected from the group consisting of wash buffer, assay buffer, elution buffer, and calibrator diluent. In some embodiments of the kits of the invention, further include a standard for the cardiac troponin.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows an analyzer that includes one electromagnetic source and one electromagnetic detector; FIG. 1B shows an analyzer that includes two electromagnetic sources and one electromagnetic detectors.

FIG. 2A shows the flow cell of an analyzer that includes one electromagnetic source; and FIG. 2B shows the flow cell of an analyzer that includes two electromagnetic sources.

FIG. 3A shows the arrangement for an analyzer that has one electromagnetic source and one electromagnetic detector; FIG. 3B shows the arrangement for an analyzer that has two electromagnetic sources and two electromagnetic detectors.

FIG. 9. Table showing cross-reactivity of capture/detection antibody pair across human, monkey, dog, and rat.

FIG. 10. Table showing endogenous serum levels of cTnI in human, monkey, dog, and rat.

FIG. 14A shows the short-term biological variation for cardiac troponin; FIG. 14B shows the long-term biological variation for cardiac troponin.

DETAILED DESCRIPTION OF THE INVENTION

Summary

Figure 1A:
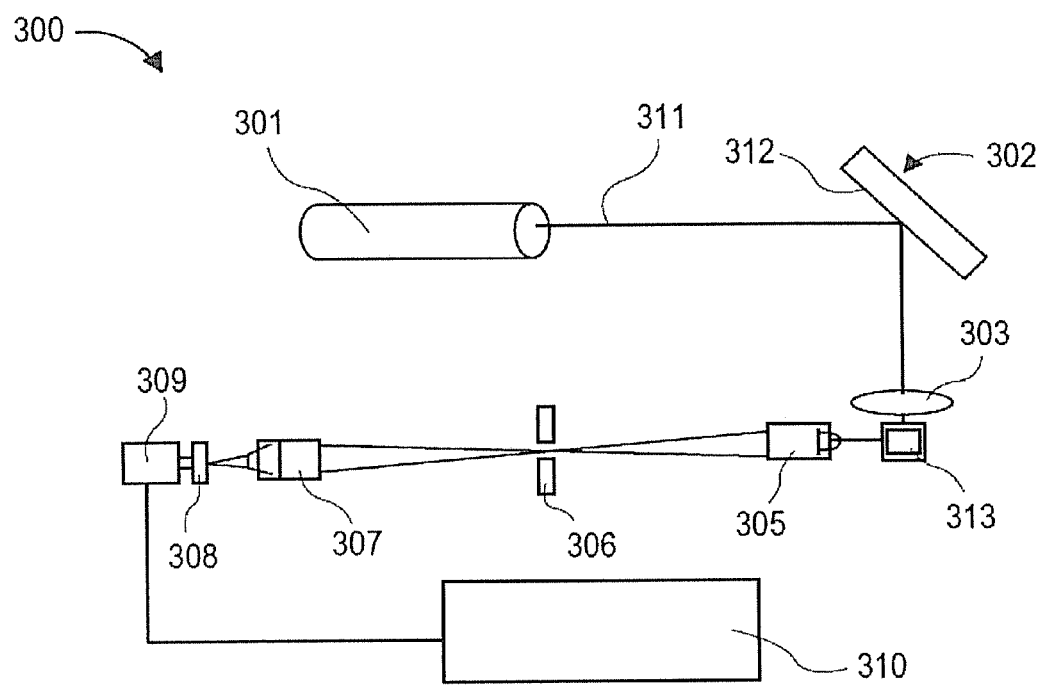
FIGS. 1A and 1B. Schematic diagram of the arrangement of the components of a single particle analyzer.

I. Introduction
II. Cardiac Troponin
III. Labels for Cardiac Troponin
   A. Binding partners for troponin
     1. Antibodies
     2. Cross-reacting antibodies
   B. Fluorescent Moieties To Be Used With Binding Partners
     1. Dyes
     2. Quantum dots
   C. Binding Partner-Fluorescent Moiety Compositions
IV. Highly Sensitive Analysis of Cardiac Troponin
   A. Sample
   B. Sample preparation
   C. Detection of troponin and determination of concentration
V. Instruments and Systems Suitable for Highly Sensitive Analysis of Troponin
   A. Apparatus/System
   B. Single Particle Analyzer
     1. Electromagnetic Radiation Source
     2. Capillary Flow Cell
     3. Motive Force
     4. Detectors
   C. Sampling System
   D. Sample preparation system
   E. Sample recovery VI. Methods Using Highly Sensitive Analysis of Cardiac Troponin
   A. Samples
   B. Determination of diagnosis, prognosis, or method of treatment
     1. Acute myocardial infarct
     2. Conditions other than AMI
       a. Cardiac toxicity
   C. Business Methods
VII. Compositions
VIII. Kits

I. Introduction

The invention provides compositions and methods for the highly sensitive detection of troponin, e.g., cardiac troponin. The release into the blood of the cardiac isoforms of troponin, which are unique to cardiac muscle (cardiac troponin I and/or T) is indicative of damage to cardiac muscle, and provides the basis for their use as diagnostic or prognostic markers, or to aid in determination of treatment.

The troponin complex in muscle consists of troponin I, C and T. Troponin C exists as two isoforms, one from cardiac and slow-twitch muscle and one from fast-twitch muscle; because it is found in virtually all striated muscle, its use as a specific marker is limited. In contrast, troponin I and T are expressed as different isoforms in slow-twitch, fast-twitch and cardiac muscle. The unique cardiac isoforms of troponin I and T allow them to be distinguished immunologically from the other troponins of skeletal muscle. Therefore, the release into the blood of cardiac troponin I and T is indicative of damage to cardiac muscle, and provides the basis for their use as diagnostic or prognostic markers, or to aid in determination of treatment.

Currently used markers for cardiac damage suffer disadvantages that limit their clinical usefulness. Cardiac enzyme assays have formed the basis for determining whether or not there is damage to the cardiac muscle. Unfortunately, the standard creatine kinase-MB (CK-MB) assay is not reliable in excluding infarction until 10 to 12 hours after the onset of chest pain. Earlier diagnosis would have very specific advantages with regard to fibrinolytic therapy and triage.

Because the level of troponin found in the circulation of healthy individuals is very low, and cardiac specific troponins do not arise from extra-cardiac sources, the troponins are very sensitive and specific markers of cardiac injury. In addition to cardiac infarct, a number of other conditions can cause damage to the heart muscle, and early detection of such damage would prove useful to clinicians. However, present methods of detection and quantitation of cardiac troponin do not possess sufficient sensitivity to detect the release of cardiac troponin into the blood until levels have reached abnormally high concentrations, e.g., 0.1 ng/ml or greater.

The methods and compositions of the invention thus include methods and compositions for the highly sensitive detection and quantitation of cardiac troponin, and compositions and methods for diagnosis, prognosis, and/or determination of treatment based on such highly sensitive detection and quantitation.

II. Cardiac Troponin

When the two unique forms of cardiac troponin, cardiac troponin I (cTnI) and cardiac troponin (cTnT) are released into the blood from cardiac muscle, several species of each may exist in the blood. These include various complexes of the two forms, with each other and/or with cardiac troponin C (cTnC). In addition, the two forms are subject to virtually immediate proteolytic degradation, resulting in a variety of fragments. Also, various phosphorylated and oxidized forms of the troponins may exist in the blood. See, e.g., U.S. Pat. No.

6,991,907, incorporated by reference herein in its entirety. Unless otherwise specified, "cardiac troponin," as used herein, encompasses all forms of cardiac troponin, including In some embodiments, the invention provides methods and compositions for the detection and/or determination of concentration of total cardiac troponin, i.e., the sum of all or a substantial portion of the cardiac troponin in a sample, e.g., blood, serum or plasma sample, whether it is free, complexed, a proteotlytic fragment, phosphorylated, oxidized, or otherwise modified. In some embodiments, the cardiac troponin is cTnI, in others, it is cTnT, and in still other embodiments, the cardiac troponin is cTnI and cTnT. It will be appreciated that an absolute total measurement need not be achieved, as long as a consistent proportion of the total is determined, which can be compared to standard values. It will also be appreciated that if a form of troponin is a minor constituent of the total, absence or low levels of detection of that form will not appreciably affect measures of total troponin. Thus, as used herein, "total cardiac troponin" refers to a measurement that is intended to measure all or substantially all forms of a particular cardiac troponin, e.g., all cTnI, or all cTnT, in a sample, where the sample-to-sample consistency is such that clinically relevant conclusions may be drawn from comparisons of samples to standards, or comparison of one sample to another.

In some embodiments, the invention provides methods and compositions for the detection and/or determination of concentration of one or more of the various forms of troponin in the sample as a separate entity, e.g., complexed cTnI, free cTnI, muddied cTnI (e.g., oxidized or phosphorylated), or complexed cTnT, free cTnT, muddied cTnT (e.g., oxidized or phosphorylated), and, typically, can provide a concentration for that form in the sample. In the latter embodiments, ratios or absolute values may be determined for the different entities. Thus, in some embodiments, the invention provides methods of detecting and, typically, determining the concentration of, one or more forms of complexed troponin, or one or more fragments of troponin, or one or more oxidized or phosphorylated forms of troponin. In some embodiments, more than one form is detected, and the concentrations of the various forms may be determined e.g., by performing multiplexed assays on a single sample for the different entities, or by performing separate assays on aliquots from the same or similar samples. Ratios of concentrations of the various forms may be obtained. For example, a ratio of the concentration of a particular form, e.g., a fragment, complex, or modified form, of the cardiac troponin to the concentration of total cardiac troponin, may be determined. These ratios and/or absolute values can provide meaningful clinical information. For example the relative proportion of fragments of cardiac troponin can indicate the length of time since release into the blood and thus, indirectly, length of time since, e.g., myocardial infarct. See, e.g., U.S. Pat. No. 6,991,907, incorporated by reference herein in its entirety.

III. Labels for Cardiac Troponin

In some embodiments, the invention provides methods and compositions that include labels for the highly sensitive detection and quantitation of cardiac troponin.

One skilled in the art will recognize that many strategies can be used for labeling target molecules to enable their detection or discrimination in a mixture of particles. The labels may be attached by any known means, including methods that utilize non-specific or specific interactions of label and target. Labels may provide a detectable signal or affect the mobility of the particle in an electric field. In addition, labeling can be accomplished directly or through binding partners.

In some embodiments, the label comprises a binding partner to troponin attached to a fluorescent moiety.

A. Binding Partners for Troponin

Any suitable binding partner with the requisite specificity for the form of cardiac troponin to be detected may be used. For example, a binding partner specific to all or substantially all forms of cTnI may be used or a binding partner specific to all or substantially all forms of cTnT may be used; typically such binding partners bind to a region of the cardiac troponin that is common to all or most of the different forms likely to be found in a sample. In some embodiments, a binding partner specific to one or more particular forms of cardiac troponin may be used, e.g., a binding partner to complexed cTnI, free cTnI, muddied cTnI (e.g., oxidized or phosphorylated), or complexed cTnT, free cTnT, muddied cTnT (e.g., oxidized or phosphorylated). Binding partners are known in the art and include, e.g., aptamers, lectins, and receptors. A useful and versatile type of binding partner is an antibody.

1. Antibodies

In some embodiments, the binding partner is an antibody specific for a cardiac troponin. The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. In some embodiments, the antibody is specific for cTnI. In some embodiments, the antibody is specific for cTnT. In some embodiments, the label includes antibodies to both cTnI and cTnT. The antibody may be specific to all or substantially all forms the cardiac troponin; e.g., all or substantially all forms of cTnI, or all or substantially all forms of cTnT. In some embodiments, an antibody specific to one or more particular forms of cardiac troponin may be used, e.g., a binding partner to complexed cTnI, free cTnI, muddied cTnI (e.g., oxidized or phosphorylated), or complexed cTnT, free cTnT, muddied cTnT (e.g., oxidized or phosphorylated). Mixtures of antibodies are also encompassed by the invention, e.g., mixtures of antibodies to cTnI and cTnT, or mixtures of antibodies to the various forms of the troponin (free, complexed, etc.), or mixtures of mixtures.

It will be appreciated that the choice of epitope or region of troponin to which the antibody is raised will determine its specificity, e.g., for total troponin, for certain fragments, for complexed troponin, for modified troponin, and the like. In some embodiments, the antibody is specific to a specific amino acid region of a cardiac troponin. In some embodiments, the antibody is specific to amino acids 27-41 of human cardiac troponin I. Both monoclonal and polyclonal antibodies are useful as binding partners. In some embodiments, the antibody is a polyclonal antibody. In some embodiments, the antibody is a monoclonal antibody. In some embodiments, the antibody is a polyclonal antibody specific to amino acids 27-41 of human cardiac troponin I. In some embodiments, this antibody is not affected by heparin, phosphorylation, oxidation and troponin complex formation, and does not cross-react with skeletal muscle troponin I.

Methods for producing antibodies are well-established. The cardiac specific sequences to troponin I and troponin T are described in FEBS Lett. 270, 57-61 (1990) and Genomics 21, 311-316 (1994). One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)). Methods for raising antibodies to the various complexed, fragment, phosphorylated, and oxidized forms of the troponins are disclosed in U.S. Pat. Nos. 5,579,687; 6,991,907; and in US Patent Application No. 20050164317, which are herein incorporated by reference in their entirety. A synthetic peptide comprised of 14 amino acids which mimics a cardiac specific sequence of troponin I and methods used to prepare antibodies to the peptide are described in international Patent Application number PCT/US94/05468. Monoclonal and polyclonal antibodies to free and complexed cardiac troponins are also commercially available (HyTest, HyTest Ltd., Turku Finland; Abcam Inc., Cambridge, Mass., USA, Life Diagnostics, Inc., West Chester, Pa., USA; Fitzgerald Industries International, Inc., Concord, Mass. 01742-3049 USA; BiosPacific, Emeryville, Calif.).

In some embodiments, the antibody is a mammalian, e.g., goat polyclonal anti-cTnI antibody. The antibody may be specific to specific regions of the cTnI, e.g., amino acids 27-41 of human cardiac troponin I. Capture binding partners and detection binding partner pairs, e.g., capture and detection antibody pairs, may be used in embodiments of the invention. Thus, in some embodiments, a heterogeneous assay protocol is used in which, typically, two binding partners, e.g., two antibodies, are used. One binding partner is a capture partner, usually immobilized on a solid support, and the other binding partner is a detection binding partner, typically with a detectable label attached. In some embodiments, the capture binding partner member of a pair is an antibody that is specific to all or substantially all forms of cardiac troponin. An example is an antibody, e.g., a monoclonal antibody, specific to free cardiac troponin I (cTnI) a.a. 41-49 and cTnI forming complexes with other troponin components. Preferably, this antibody is not affected by heparin, phosphorylation, oxidation and troponin complex formation, and does not cross-react with skeletal muscle troponin I. Thus, it is thought that the antibody binds to total cTnI. Another example is a monoclonal antibody, specific to cardiac troponin I (cTnI) a.a. 87-91 and does not cross-react with skeletal muscle troponin I. Such antibodies are available from BiosPacific, Emeryville, Calif. Other antibody pairs are known or can be designed.

Cross-reacting antibodies In some embodiments it is useful to use an antibody that cross-reacts with a variety of species, either as a capture antibody, a detection antibody, or both. Such embodiments include the measurement of drug toxicity by determining, e.g., release of cardiac troponin into the blood as a marker of cardiac damage. A cross-reacting antibody allows studies of toxicity to be done in one species, e.g. a non-human species, and direct transfer of the results to studies or clinical observations of another species, e.g., humans, using the same antibody or antibody pair in the reagents of the assays, thus decreasing variability between assays. Thus, in some embodiments, one or more of the antibodies for use as a binding partner to the marker, e.g., cardiac troponin, such as cardiac troponin I, may be a cross-reacting antibody. In some embodiments, the antibody cross-reacts with the marker, e.g. cardiac troponin, from at least two species selected from the group consisting of human, monkey, dog, rat, and mouse. In some embodiments the antibody cross-reacts with the marker e.g. cardiac troponin, from all of the group consisting of human, monkey, dog, rat, and mouse. In some embodiments, the antibody cross-reacts with cardiac troponin, e.g., cardiac troponin I, from human, monkey, dog, and rat. Such a cross-reacting antibody may be used in any suitable embodiment as described herein. For example, a cross-reacting antibody pair may be used wherein each member of the pair (i.e., capture and detection antibody) cross reacts across species with cardiac troponin I. The capture antibody may be immobilized on a solid support. In some embodiments, the capture antibody is immobilized on a paramagnetic microparticle, such as described in Example 5. An example of results obtained from a cross-reacting antibody pair for human, monkey, dog, and rat is given in Example 6.

B. Fluorescent Moieties to be Used with Binding Partners

In some embodiments, the binding partner, e.g., antibody, is attached to a fluorescent moiety. The fluorescence of the moiety, will be sufficient to allow detection in a single molecule detector, such as the single molecule detectors described herein. A "fluorescent moiety," as that term is used herein, includes one or more fluorescent entities whose total fluorescence is such that the moiety may be detected in the single molecule detectors described herein. Thus, a fluorescent moiety may comprise a single entity (e.g., a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity may be attached to the binding partner separately or the entities may be attached together, as long as the entities as a group provide sufficient fluorescence to be detected.

Typically, the fluorescence of the moiety involves a combination of quantum efficiency and lack of photobleaching sufficient that the moiety is detectable above background levels in a single molecule detector, with the consistency necessary for the desired level of detection, accuracy, and precision of the assay. For example, in some embodiments, the fluorescence of the fluorescent moiety is such that it allows detection and/or quantitation of troponin at a level of detection of less than about 10, 5, 4, 3, 2, or 1 pg/ml and with a coefficient of variation of less than about 20, 15, 14, 13, 12, 11, 10, 9, 8, 7, 6, 5, 4, 3, 2, 1% or less, e.g., about 10% or less, in the instruments described herein. In some embodiments, the fluorescence of the fluorescent moiety is such that it allows detection and/or quantitation of troponin at a limit of detection of less than about 5 pg/ml and with a coefficient of variation of less than about 10%, in the instruments described herein. "Limit of detection," as that term is used herein, includes the lowest concentration at which one can identify a sample as containing a molecule of the substance of interest, e.g., the first non-zero value. It can be defined by the variability of zeros and the slope of the standard curve. For example, the limit of detection of an assay may be determined by running a standard curve, determining the standard curve zero value, and adding 2 standard deviations to that value. A concentration of the substance of interest that produces a signal equal to this value is the "lower limit of detection" concentration.

Furthermore, the moiety has properties that are consistent with its use in the assay of choice. In some embodiments, the assay is an immunoassay, where the fluorescent moiety is attached to an antibody; the moiety must have properties such that it does not aggregate with other antibodies or proteins, or experiences no more aggregation than is consistent with the required accuracy and precision of the assay. In some embodiments, fluorescent moieties that are preferred are fluorescent moieties, e.g., dye molecules that have a combination of 1) high absorption coefficient; 2) high quantum yield; 3) high photostability (low photobleaching); and 4) compatibility with labeling the biomolecule of interest (e.g., protein) so that it may be analyzed using the analyzers and systems of the invention (e.g., does not cause precipitation of the protein of interest, or precipitation of a protein to which the moiety has been attached).

Fluorescent moieties, e.g. a single fluorescent dye molecule or a plurality of fluorescent dye molecules, that are useful in some embodiments of the invention may be defined in terms of their photon emission characteristics when stimulated by EM radiation. For example, in some embodiments, the invention utilizes a fluorescent dye moiety, e.g., a single fluorescent dye molecule or a plurality of fluorescent dye molecules, that is capable of emitting an average of at least about 10, 20, 30, 40, 50, 75, 100, 125, 150, 175, 200, 225, 250, 275, 300, 350, 400, 500, 600, 700, 800, 900, or 1000, photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. It will be appreciated that the total energy may be achieved by many different combinations of power output of the laser and length of time of exposure of the dye moiety. E.g., a laser of a power output of 1 mW may be used for 3 ms, 3 mW for 1 ms, 6 mW for 0.5 ms, 12 mW for 0.25 ms, and so on.

In some embodiments, the invention utilizes a fluorescent dye moiety, e.g., a single fluorescent dye molecule or a plurality of fluorescent dye molecules, that is capable of emitting an average of at least about 50 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 100 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 150 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 300 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety e.g., a single fluorescent dye molecule or a plurality of fluorescent dye molecules, that is capable of emitting an average of at least about 500 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules.

In some embodiments, the fluorescent moiety comprises an average of at least about 1, 2, 3, 4, 5, 6, 7, 8, 9, or fluorescent entities, e.g., fluorescent molecules. In some embodiments, the fluorescent moiety comprises an average of no more than about 2, 3, 4, 5, 6, 7, 8, 9, 10, or 11 fluorescent entities, e.g., fluorescent molecules. In some embodiments, the fluorescent moiety comprises an average of about 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 fluorescent entities. In some embodiments, the fluorescent moiety comprises an average of about 2 to 8 fluorescent moieties are attached. In some embodiments, an average of about 2 to 6 fluorescent entities. In some embodiments, the fluorescent moiety comprises an average of about 2 to 4 fluorescent entities. In some embodiments, the fluorescent moiety comprises an average of about 3 to 10 fluorescent entities. In some embodiments, the fluorescent moiety comprises an average of about 3 to 8 fluorescent entities. In some embodiments, the fluorescent moiety comprises an average of about 3 to 6 fluorescent entities. By "average" is meant that, in a given sample that is a representative sample of a group of labels of the invention, where the sample contains a plurality of the binding partner-fluorescent moiety units, the molar ratio of the particular fluorescent entity of which the fluorescent moiety is comprise, to the binding partner, as determined by standard analytical methods, corresponds to the number or range of numbers specified For example, in embodiments in which the label comprises a binding partner that is an antibody and a fluorescent moiety that comprises a plurality of fluorescent dye molecules of a specific absorbance, a spectrophometric assay may be used in which a solution of the label is diluted to an appropriate level and the absorbance at 280 nm is taken to determine the molarity of the protein (antibody) and an absorbance at, e.g., 650 nm (for AlexaFluor 647) is taken to determine the molarity of the fluorescent dye molecule. The ratio of the latter molarity to the former represents the average number of fluorescent entities (dye molecules) in the fluorescent moiety attached to each antibody.

1. Dyes

In some embodiments, the invention utilizes fluorescent moieties that comprise fluorescent dye molecules. In some embodiments, the invention utilizes a fluorescent dye molecule that is capable of emitting an average of at least about 50 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 75 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 100 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 150 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 200 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules A non-inclusive list of useful fluorescent entities for use in the fluorescent moieties of the invention is given in Table 1, below. In some embodiments, the fluorescent entity is selected from the group consisting of Alexa Flour 488, 532, 647, 700, 750, Fluorescein, B-phycoerythrin, allophycocyanin, PBXL-3, and Qdot 605.

TABLE 1

FLUORESCENT ENTITIES

| Dye | Ex (nm) | E (M)−1 | Em (nm) | Mw |
|---|---|---|---|---|
| Bimane | 380 | 5,700 | 458 | 282.31 |
| Dapoxyl | 373 | 22,000 | 551 | 362.83 |
| Dimethylamino coumarin-4-acetic acid | 375 | 22,000 | 470 | 344.32 |
| Marina blue | 365 | 19,000 | 460 | 367.26 |
| 8-Anilino naphthalene-1-sulfonic acid | 372 | | 480 | |
| Cascade blue | 376 | 23,000 | 420 | 607.42 |
| Alexa Fluor 405 | 402 | 35,000 | 421 | 1028.26 |
| Cascade blue | 400 | 29,000 | 420 | 607.42 |
| Cascade yellow | 402 | 24,000 | 545 | 563.54 |
| Pacific blue | 410 | 46,000 | 455 | 339.21 |
| PyMPO | 415 | 26,000 | 570 | 582.41 |
| Alexa 430 | 433 | 15,000 | 539 | 701.75 |
| Atto-425 | 438 | | 486 | |
| NBD | 465 | 22,000 | 535 | 391.34 |
| Alexa 488 | 495 | 73,000 | 519 | 643.41 |
| Fluorescein | 494 | 79,000 | 518 | 376.32 |
| Oregon Green 488 | 496 | 76,000 | 524 | 509.38 |
| Atto 495 | 495 | | 522 | |
| Cy2 | 489 | 150,000 | 506 | 713.78 |
| DY-480-XL | 500 | 40,000 | 630 | 514.60 |
| DY-485-XL | 485 | 20,000 | 560 | 502.59 |
| DY-490-XL | 486 | 27,000 | 532 | 536.58 |
| DY-500-XL | 505 | 90,000 | 555 | 596.68 |
| DY-520-XL | 520 | 40,000 | 664 | 514.60 |
| Alexa Fluor 532 | 531 | 81,000 | 554 | 723.77 |
| BODIPY 530/550 | 534 | 77,000 | 554 | 513.31 |
| 6-HEX | 535 | 98,000 | 556 | 680.07 |
| 6-JOE | 522 | 75,000 | 550 | 602.34 |
| Rhodamine 6G | 525 | 108,000 | 555 | 555.59 |
| Atto-520 | 520 | | 542 | |
| Cy3B | 558 | 130,000 | 572 | 658.00 |
| Alexa Fluor 610 | 612 | 138,000 | 628 | |
| Alexa Fluor 633 | 632 | 159,000 | 647 | ca. 1200 |
| Alexa Fluor 647 | 650 | 250,000 | 668 | ca. 1250 |
| BODIPY 630/650 | 625 | 101,000 | 640 | 660.50 |
| Cy5 | 649 | 250,000 | 670 | 791.99 |
| Alexa Fluor 660 | 663 | 110,000 | 690 | |
| Alexa Fluor 680 | 679 | 184,000 | 702 | |

TABLE 1-continued

FLUORESCENT ENTITIES

| Alexa Fluor 700 | 702 | 192,000 | 723 | |
| Alexa Fluor 750 | 749 | 240,000 | 782 | |
| B-phycoerythrin | 546, 565 | 2,410,000 | 575 | 240,000 |
| R-phycoerythrin | 480, 546, 565 | 1,960,000 | 578 | 240,000 |
| Allophycocyanin | 650 | 700,000 | 660 | 700,000 |
| PBXL-1 | 545 | | 666 | |
| PBXL-3 | 614 | | 662 | |

Atto-tec dyes

| Name | Ex (nm) | Em (nm) | QY | □ (ns) |
|---|---|---|---|---|
| Atto 425 | 436 | 486 | 0.9 | 3.5 |
| Atto 495 | 495 | 522 | 0.45 | 2.4 |
| Atto 520 | 520 | 542 | 0.9 | 3.6 |
| Atto 560 | 561 | 585 | 0.92 | 3.4 |
| Atto 590 | 598 | 634 | 0.8 | 3.7 |
| Atto 610 | 605 | 630 | 0.7 | 3.3 |
| Atto 655 | 665 | 690 | 0.3 | 1.9 |
| Atto 680 | 680 | 702 | 0.3 | 1.8 |

Dyomics Fluors

| label | Ex (nm) | Molar absorbance* [l · mol−1 · cm−1] | Em (nm) | molecular weight# [g · mol−1] |
|---|---|---|---|---|
| DY-495/5 | 495 | 70,000 | 520 | 489.47 |
| DY-495/6 | 495 | 70,000 | 520 | 489.47 |
| DY-495X/5 | 495 | 70,000 | 520 | 525.95 |
| DY-495X/6 | 495 | 70,000 | 520 | 525.95 |
| DY-505/5 | 505 | 85,000 | 530 | 485.49 |
| DY-505/6 | 505 | 85,000 | 530 | 485.49 |
| DY-505X/5 | 505 | 85,000 | 530 | 523.97 |
| DY-505X/6 | 505 | 85,000 | 530 | 523.97 |
| DY-550 | 553 | 122,000 | 578 | 667.76 |
| DY-555 | 555 | 100.000 | 580 | 636.18 |
| DY-610 | 609 | 81.000 | 629 | 667.75 |
| DY-615 | 621 | 200.000 | 641 | 578.73 |
| DY-630 | 636 | 200.000 | 657 | 634.84 |
| DY-631 | 637 | 185.000 | 658 | 736.88 |
| DY-633 | 637 | 180.000 | 657 | 751.92 |
| DY-635 | 647 | 175.000 | 671 | 658.86 |
| DY-636 | 645 | 190.000 | 671 | 760.91 |
| DY-650 | 653 | 170.000 | 674 | 686.92 |
| DY-651 | 653 | 160.000 | 678 | 888.96 |
| DYQ-660 | 660 | 117,000 | — | 668.86 |
| DYQ-661 | 661 | 116,000 | — | 770.90 |
| DY-675 | 674 | 110.000 | 699 | 706.91 |
| DY-676 | 674 | 145.000 | 699 | 807.95 |
| DY-680 | 690 | 125.000 | 709 | 634.84 |
| DY-681 | 691 | 125.000 | 708 | 736.88 |
| DY-700 | 702 | 96.000 | 723 | 668.86 |
| DY-701 | 706 | 115.000 | 731 | 770.90 |
| DY-730 | 734 | 185.000 | 750 | 660.88 |
| DY-731 | 736 | 225.000 | 759 | 762.92 |
| DY-750 | 747 | 240.000 | 776 | 712.96 |
| DY-751 | 751 | 220.000 | 779 | 814.99 |
| DY-776 | 771 | 147.000 | 801 | 834.98 |
| DY-780-OH | 770 | 70.000 | 810 | 757.34 |
| DY-780-P | 770 | 70.000 | 810 | 957.55 |
| DY-781 | 783 | 98.000 | 800 | 762.92 |
| DY-782 | 782 | 102.000 | 800 | 660.88 |
| EVOblue-10 | 651 | 101.440 | 664 | 389.88 |
| EVOblue-30 | 652 | 102.000 | 672 | 447.51 |

Quantum Dots: Qdot 525, 565, 585, 605, 655, 705, 800

Suitable dyes for use in the invention include modified carbocyanine dyes. The modification of carbocyanine dyes includes the modification of an indolium ring of the carbocyanine dye to permit a reactive group or conjugated substance at the number 3 position. The modification of the indolium ring provides dye conjugates that are uniformly and substantially more fluorescent on proteins, nucleic acids and other biopolymers, than conjugates labeled with structurally similar carbocyanine dyes bound through the nitrogen atom at the number one position. In addition to having more intense fluorescence emission than structurally similar dyes at virtually identical wavelengths, and decreased artifacts in their absorption spectra upon conjugation to biopolymers, the modified carbocyanine dyes have greater photostability and higher absorbance (extinction coefficients) at the wavelengths of peak absorbance than the structurally similar dyes. Thus, the modified carbocyanine dyes result in greater sensitivity in assays that use the modified dyes and their conjugates. Preferred modified dyes include compounds that have at least one substituted indolium ring system in which the substituent on the 3-carbon of the indolium ring contains a chemically reactive group or a conjugated substance. Other dye compounds include compounds that incorporate an azabenzazolium ring moiety and at least one sulfonate moiety. The modified carbocyanine dyes that can be used to detect individual particles in various embodiments of the invention are described in U.S. Pat. No. 6,977,305, which is herein incorporated by reference in its entirety. Thus, in some embodiments the labels of the invention utilize a fluorescent dye that includes a substituted indolium ring system in which the substituent on the 3-carbon of the indolium ring contains a chemically reactive group or a conjugated substance group.

In some embodiments, the label comprises a fluorescent moiety that includes one or more Alexa dyes (Molecular Probes, Eugene, Oreg.). The Alexa dyes are disclosed in U.S. Pat. Nos. 6,977,305; 6,974,874; 6,130,101; and 6,974,305, which are herein incorporated by reference in their entirety. Some embodiments of the invention utilize a dye chosen from the group consisting of AlexaFluor 647, AlexaFluor 488, AlexaFluor 532, AlexaFluor 555, AlexaFluor 610, AlexaFluor 680, AlexaFluor 700, and AlexaFluor 750. Some embodiments of the invention utilize a dye chosen from the group consisting of AlexaFluor 488, AlexaFluor 532, AlexaFluor 647, AlexaFluor 700 and AlexaFluor 750. Some embodiments of the invention utilize the AlexaFluor 647 molecule, which has an absorption maximum between about 650 and 660 nm and an emission maximum between about 660 and 670 nm. The AlexaFluor 647 dye is used alone or in combination with other AlexaFluor dyes.

In addition, currently available organic fluors can be improved by rendering them less hydrophobic by adding hydrophilic groups such as polyethylene. Alternatively, currently sulfonated organic fluors such as the AlexaFluor 647 dye can be rendered less acidic by making them zwitterionic. Particles such as antibodies that are labeled with the modified fluors are less likely to bind non-specifically to surfaces and proteins in immunoassays, and thus enable assays that have greater sensitivity and lower backgrounds. Methods for modifying and improving the properties of fluorescent dyes for the purpose of increasing the sensitivity of a system that detects single particles are known in the art. Preferably, the modification improves the Stokes shift while maintaining a high quantum yield.

2 Quantum Dots

In some embodiments, the fluorescent label moiety that is used to detect a molecule in a sample using the analyzer systems of the invention is a quantum dot. Quantum dots (QDs), also known as semiconductor nanocrystals or artificial atoms, are semiconductor crystals that contain anywhere between 100 to 1,000 electrons and range from 2-10 nm. Some QDs can be between 10-20 nm in diameter. QDs have high quantum yields, which makes them particularly useful for optical applications. QDs are fluorophores that fluoresce by forming excitons, which can be thought of the excited state of traditional fluorophores, but have much longer lifetimes of up to 200 nanoseconds. This property provides QDs with low photobleaching. The energy level of QDs can be controlled by changing the size and shape of the QD, and the depth of the QDs' potential. One of the optical features of small excitonic QDs is coloration, which is determined by the size of the dot. The larger the dot, the redder, or more towards the red end of the spectrum the fluorescence. The smaller the dot, the bluer or more towards the blue end it is. The bandgap energy that determines the energy and hence the color of the fluoresced light is inversely proportional to the square of the size of the QD. Larger QDs have more energy levels which are more closely spaced, thus allowing the QD to absorb photons containing less energy, i.e. those closer to the red end of the spectrum. Because the emission frequency of a dots dependent on the bandgap, it is therefore possible to control the output wavelength of a dot with extreme precision. In some embodiments the protein that is detected with the single particle analyzer system is labeled with a QD. In some embodiments, the single particle analyzer is used to detect a protein labeled with one QD and using a filter to allow for the detection of different proteins at different wavelengths.

QDs have broad excitation and narrow emission properties which when used with color filtering require only a single electromagnetic source for multiplex analysis of multiple targets in a single sample to resolve individual signals. Thus, in some embodiments, the analyzer system comprises one continuous wave laser and particles that are each labeled with one QD. Colloidally prepared QDs are free floating and can be attached to a variety of molecules via metal coordinating functional groups. These groups include but are not limited to thio, amine, nitrile, phosphine, phosphine oxide, phosphonic acid, carboxylic acids or other ligands. By bonding appropriate molecules to the surface, the quantum dots can be dispersed or dissolved in nearly any solvent or incorporated into a variety of inorganic and organic films. Quantum dots (QDs) can be coupled to streptavidin directly through a maleimide ester coupling reaction or to antibodies through a meleimide-thiol coupling reaction. This yields a material with a biomolecule covalently attached on the surface, which produces conjugates with high specific activity. In some embodiments, the protein that is detected with the single particle analyzer is labeled with one quantum dot. In some embodiments the quantum dot is between 10 and 20 nm in diameter. In other embodiments, the quantum dot is between 2 and 10 nm in diameter. Useful Quantum Dots include QD 605, QD 610, QD 655, and QD 705. A particularly preferred Quantum Dot is QD 605.

C. Binding Partner-Fluorescent Moiety Compositions (Labels)

The labels of the invention generally contain a binding partner, e.g., antibody, bound to a fluorescent moiety to provide the requisite fluorescence for detection and quantitation in the instruments described herein. Any suitable combination of binding partner and fluorescent moiety for detection in the single molecule detectors described herein may be used as a label in the invention. In some embodiments, the invention provides a label for a cardiac troponin molecule, or fragment, complex, phosphorylated, or oxidized form thereof, where the label includes an antibody to a cardiac troponin and a fluorescent moiety. The antibody may be any antibody as described above, e.g., an antibody to cTnT or cTnI. In some embodiments, the antibody is an antibody to cTnI. In some embodiments, the antibody is specific to a specific region of the cardiac troponin, e.g., specific to amino acids 27-41 of human cTnI. In some embodiments, the invention provides compositions comprising a fluorescent moiety attached to an anti-cTnI antibody, e.g., a polyclonal antibody such as a goat polyclonal antibody from those designated G129C available from BiosPacific, Emeryville. A fluorescent moiety may be attached such that the label is capable of emitting an average of at least about 50, 75, 100, 125, 150, 175, 200, 225, 250, 275, 300, 350, 400, 500, 600, 700, 800, 900, or 1000, photons when stimulated by a laser emitting light at the excitation wavelength of the moiety, where the laser is focused on a spot of not less than about 5 microns in diameter that contains the label, and wherein the total energy directed at the spot by the laser is no more than about 3 microJoules. In some embodiments, the fluorescent moiety may be a fluorescent moiety that is capable of emitting an average of at least about 50, 100, 150, or 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. The fluorescent moiety may be a fluorescent moiety that includes one or more dye molecules with a structure that includes a substituted indolium ring system in which the substituent on the 3-carbon of the indolium ring contains a chemically reactive group or a conjugated substance group. The label composition may include a fluorescent moiety that includes one or more dye molecules selected from the group consisting of AlexaFluor 488, 532, 647, 700, or 750. The label composition may include a fluorescent moiety that includes one or more dye molecules selected from the group consisting of AlexaFluor 488, 532, 700, or 750. The label composition may include a fluorescent moiety that includes one or more dye molecules that are AlexaFluor 488. The label composition may include a fluorescent moiety that includes one or more dye molecules that are AlexaFluor 555. The label composition may include a fluorescent moiety that includes one or more dye molecules that are AlexaFluor 610. The label composition may include a fluorescent moiety that includes one or more dye molecules that are AlexaFluor 647. The label composition may include a fluorescent moiety that includes one or more dye molecules that are AlexaFluor 680. The label composition may include a fluorescent moiety that includes one or more dye molecules that are AlexaFluor 700. The label composition may include a fluorescent moiety that includes one or more dye molecules that are AlexaFluor 750.

In some embodiments the invention provides a composition for the detection of cardiac troponin I that includes an AlexFluor molecule, e.g. an AlexaFluor molecule selected from the described groups, such as an AlexaFluor 647 molecule attached to a to an antibody, e.g., a goat polyclonal anti-cTnI antibody, specific for amino acids 27-41 of human cTnI. In some embodiments the invention provides a composition for the detection of cardiac troponin I that includes an average of 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 AlexaFluor 647 molecules molecule attached an antibody, e.g., a goat polyclonal anti-cTnI antibody, specific for amino acids 27-41 of human cTnI. In some embodiments the invention provides a composition for the detection of cardiac troponin I that includes an average of 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 AlexaFluor 647 molecules molecule attached to an antibody, e.g., a goat polyclonal anti-cTnI antibody, specific for amino acids 27-41 of human cTnI. In some embodiments the invention provides a composition for the detection of cardiac troponin I that includes an average of about 2 to 10 AlexaFluor 647 molecules molecule attached to an antibody, e.g., a goat polyclonal anti-cTnI antibody, specific for amino acids 27-41 of human cTnI. In some embodiments the invention provides a composition for the detection of cardiac troponin I that includes an average of about 2 to 8 AlexaFluor 647 molecules molecule attached to an antibody, e.g., a goat polyclonal anti-cTnI antibody, specific for amino acids 27-41 of human cTnI. In some embodiments the invention provides a composition for the detection of cardiac troponin I that includes an average of about 2 to 6 AlexaFluor 647 molecules molecule attached to an antibody, e.g., a goat polyclonal anti-cTnI antibody, specific for amino acids 27-41 of human cTnI. In some embodiments the invention provides a composition for the detection of cardiac troponin I that includes an average of about 2 to 4 AlexaFluor 647 molecules molecule attached to an antibody, e.g., a goat polyclonal anti-cTnI antibody, specific for amino acids 27-41 of human cTnI. In some embodiments the invention provides a composition for the detection of cardiac troponin I that includes an average of about 3 to 8 AlexaFluor 647 molecules molecule attached to an antibody, e.g., a goat polyclonal anti-cTnI antibody, specific for amino acids 27-41 of human cTnI. In some embodiments the invention provides a composition for the detection of cardiac troponin I that includes an average of about 3 to 6 AlexaFluor 647 molecules molecule attached to an antibody, e.g., a goat polyclonal anti-cTnI antibody, specific for amino acids 27-41 of human cTnI. In some embodiments the invention provides a composition for the detection of cardiac troponin I that includes an average of about 4 to 8 AlexaFluor 647 molecules molecule attached to an antibody, e.g., a goat polyclonal anti-cTnI antibody, specific for amino acids 27-41 of human cTnI.

Attachment of the fluorescent moiety, or fluorescent entities that make up the fluorescent moiety, to the binding partner, e.g., antibody, may be by any suitable means; such methods are well-known in the art and exemplary methods are given in the Examples. In some embodiments, after attachment of the fluorescent moiety to the binding partner to form a label for use in the methods of the invention, and prior to the use of the label for labeling the protein of interest, it is useful to perform a filtration step. E.g., an antibody-dye label may be filtered prior to use, e.g., through a 0.2 micron filter, or any suitable filter for removing aggregates. Other reagents for use in the assays of the invention may also be filtered, e.g., e.g., through a 0.2 micron filter, or any suitable filter. Without being bound by theory, it is thought that such filtration removes a portion of the aggregates of the, e.g., antibody-dye labels. As such aggregates will bind as a unit to the protein of interest, but upon release in elution buffer are likely to disaggregate, false positives may result; i.e., several labels will be detected from an aggregate that has bound to only a single protein molecule of interest. Regardless of theory, filtration has been found to reduce false positives in the subsequent assay and to improve accuracy and precision.

IV. Highly Sensitive Analysis of Cardiac Troponin

In one aspect, the invention provides a method for determining the presence or absence of a single molecule of cardiac troponin or a fragment or complex thereof in a sample, by i) labeling the molecule, fragment, or complex, if present, with a label; and ii) detecting the presence or absence of the label, where the detection of the presence of the label indicates the presence of the single molecule, fragment, or complex of cardiac troponin in the sample. As used herein, "molecule of cardiac troponin" includes a molecule that contains substantially the entire naturally-occurring amino acid sequence of the particular type of cardiac troponin, including post-translationally modified forms, e.g., phosphorylated forms, as well as oxidized or otherwise chemically altered forms. As used herein, a "fragment" of a molecule includes a molecule of cardiac troponin that contains less than the entire naturally-occurring amino acid sequence, including modifications as for the entire molecule. As used herein, a "complex" of a molecule of cardiac troponin includes a molecule of cardiac troponin or a fragment that is associated with one or more other molecules or substances, e.g., that is associated with one or more other molecules of cardiac troponin. In some embodiments, the method is capable of detecting the troponin at a limit of detection of less than about 100, 80, 60, 50, 40, 30, 20, 15, 12, 10, 9, 8, 7, 6, 5, 4, 3, 2, 1, 0.9, 0.8, 0.7, 0.6, 0.5, 0.4, 0.3, 0.2. or 0.1 pg/ml. In some embodiments, the method is capable of detecting the troponin at a limit of detection of less than about 100 pg/ml. In some embodiments, the method is capable of detecting the troponin at a limit of detection of less than about 50 pg/ml. In some embodiments, the method is capable of detecting the troponin at a limit of detection of less than about 20 pg/ml. In some embodiments, the method is capable of detecting the troponin at a limit of detection of less than about 10 pg/ml. In some embodiments, the method is capable of detecting the troponin at a limit of detection of less than about 5 pg/ml. In some embodiments, the method is capable of detecting the troponin at a limit of detection of less than about 3 pg/ml. In some embodiments, the method is capable of detecting the troponin at a limit of detection of less than about 1 pg/ml. Detection limits may be determined by use of the appropriate National Institute of Standards and Technology reference standard material, e.g., standard cTnI.

The methods also provide methods of determining a concentration of cardiac troponin in a sample by detecting single molecules of troponin in the sample. The "detecting" of a single molecule of troponin includes detecting the molecule directly or indirectly. In the case of indirect detection, labels that corresponds to single molecules of cardiac troponin, e.g., a labels that have been attached to the single molecules of cardiac troponin, may be detected.

Types of cardiac troponin for detection are as described herein, e.g., cTnT, cTnI, total cardiac troponin (e.g., total cTnI or total cTnT) or free, complexed, or fragments of cardiac troponin. In some embodiments, total cardiac troponin is detected and/or quantitated. In some embodiments, total cTnT is detected. In some embodiments, total cTnI is detected and/or quantitated.

The methods also provide for the measurement of low levels of biomarkers other than troponin. For example, the detection of cytokines in plasma in the absence of inflammation, at, for example, the level of cytokines known to exist in the circulating plasma proteome of a healthy individual (ref. 2). Another non-limiting example is the detection and measurement of p24, a viral protein present in HIV infected individuals, which is present in the early stages of HIV infection well before HIV antibodies are produced and can be detected (ref. 12).

A. Sample

The sample may be any suitable sample. Typically, the sample is a biological sample, e.g., a biological fluid. Such fluids include, without limitation, exhaled breath condensate (EBC), bronchoalveolar lavage fluid (BAL), blood, serum, plasma, urine, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which may contain the target particle of interest. Other similar specimens such as cell or tissue culture or culture broth are also of interest.

In some embodiments, the sample is a blood sample. In some embodiments the sample is a plasma sample. In some embodiments the sample is a serum sample.

B. Sample Preparation

In general, any method of sample preparation may be used that produces a label corresponding to a molecule of cardiac troponin that is wished to be measured, where the label is detectable in the instruments described herein. As is known in the art, sample preparation in which a label is added to one or more particles may be performed in a homogeneous or heterogeneous format. In some embodiments, the sample preparation is formed in a homogenous format. In analyzer system employing a homogenous format, unbound label is not removed from the sample. See, e.g., U.S. patent application Ser. No. 11/048,660, incorporated by reference herein in its entirety. In some embodiments, the particle or particles of interest are labeled by addition of labeled antibody or antibodies that bind to the particle or particles of interest.

In some embodiments, a heterogeneous assay format is used, where, typically, a step is employed for removing unbound label. Such assay formats are well-known in the art. One particularly useful assay format is a sandwich assay, e.g., a sandwich immunoassay. In this format, the molecule of interest, e.g., marker of a biological state, is captured, e.g., on a solid support, using a capture binding partner. Unwanted molecules and other substances may then optionally be washed away, followed by binding of a label comprising a detection binding partner and a detectable label, e.g., fluorescent moiety. Further washes remove unbound label, then the detectable label is released, usually though not necessarily still attached to the detection binding partner. In alternative embodiments, sample and label are added to the capture binding partner without a wash in between, e.g., at the same time. Other variations will be apparent to one of skill in the art.

In some embodiments, the method for detecting troponin particles uses a sandwich assay with antibodies, e.g., monoclonal antibodies as capture binding partners. The method comprises binding troponin molecules in a sample to a capture antibody that is immobilized on a binding surface, and binding the detection antibody to the troponin molecule to form a "sandwich" complex. The detection antibody comprises a detectable fluorescent label, as described herein, which is detected, e.g., using the single molecule analyzers of the invention. Both the capture and detection antibodies specifically bind troponin. Many example of sandwich immunoassays are known, and some are described in U.S. Pat. No. 4,168,146 to Grubb et al. and U.S. Pat. No. 4,366,241 to Tom et al., both of which are incorporated herein by reference. Further examples specific to cardiac troponin are described in the Examples.

The capture binding partner may be attached to a solid support, e.g., a microtiter plate or paramagnetic beads. In some embodiments, the invention provides a binding partner for a cardiac troponin attached to a paramagnetic bead. Any suitable binding partner that is specific for the type of cardiac troponin that it is wished to capture may be used. The binding partner may be an antibody, e.g., a monoclonal antibody. The antibody may be specific for free cardiac troponin (cTnI or cTnT) or for complexed cardiac troponin, modified cardiac troponin, or fragments of cardiac troponin, as described herein, or specific to all or substantially all forms of cardiac troponin, e.g., cTnI or cTnT, likely to be found in the sample of interest. Production and sources of antibodies to cardiac troponin are described elsewhere herein. Preferred antibodies for measuring total troponin are those that not substantially affected by heparin, phosphorylation, oxidation and troponin complex formation, and that do not cross-react with skeletal muscle troponin, e.g., troponin I. In some embodiments, the antibody is specific for a specific region of a cardiac troponin. In some embodiments, the region includes amino acids 41-49 of human cardiac troponin I. In some embodiments, the region includes amino acids 87-91 of human cardiac troponin I. Such antibodies are well-known in the art and are available from, e.g. BiosPacific, Emeryville, Calif. An example of a capture antibody useful in embodiments of the invention is an antibody, e.g., a monoclonal antibody, that reacts with free cardiac troponin I (cTnI) a.a. 41-49 and cTnI forming complexes with other troponin components. Preferably, this antibody is not affected by heparin, phosphorylation, oxidation and troponin complex formation, and does not cross-react with skeletal muscle troponin I. An exemplary antibody of this type is Monoclonal Antibody Clone Number A34650228P, available from BiosPacific, Emeryville, Calif. Another example of a capture antibody useful in embodiments of the invention is an antibody, e.g., a monoclonal antibody, that reacts with free cardiac troponin I (cTnI) a.a. 87-91 and cTnI forming complexes with other troponin components. Preferably, this antibody is not affected by heparin, phosphorylation, oxidation and troponin complex formation, and does not cross-react with skeletal muscle troponin I. An exemplary antibody of this type is Monoclonal Antibody Clone Number A34440228P, available from BiosPacific, Everyville, Calif. It will be appreciated that antibodies identified herein as useful as a capture antibody may also be useful as detection antibodies, and vice versa.

The attachment of the binding partner, e.g., antibody, to the solid support may be covalent or noncovalent. In some embodiments, the attachment is noncovalent. An example of a noncovalent attachment well-known in the art is biotin-avidin/streptavidin interactions. Thus, in some embodiments, a solid support, e.g., a microtiter plate or a paramagnetic bead, is attached to the capture binding partner, e.g., antibody, through noncovalent attachment, e.g., biotin-avidin/streptavidin interactions. In some embodiments, the attachment is covalent. Thus, in some embodiments, a solid support, e.g., a microtiter plate or a paramagnetic bead, is attached to the capture binding partner, e.g., antibody, through covalent attachment. Covalent attachment in which the orientation of the capture antibody is such that capture of the molecule of interest is optimized is especially useful. For example, in some embodiments a solid support, e.g., a microtiter plate or a paramagnetic microparticle, may be used in which the attachment of the binding partner, e.g., antibody, is an oriented attachment, e.g., a covalent oriented attachment.

An exemplary protocol for oriented attachment of an antibody to a solid support is as follows: IgG is dissolved in 0.1M sodium acetate buffer, pH 5.5 to a final concentration of 1 mg/ml. An equal volume of ice-cold 20 mM sodium periodate in 0.1 M sodium acetate, pH 5.5 is added. The IgG is allowed to oxidize for ½ hour on ice. Excess periodate reagent is quenched by the addition of 0.15 volume of 1 M glycerol. Low molecular weight byproducts of the oxidation reaction are removed by ultrafiltration. The oxidized IgG fraction is diluted to a suitable concentration (typically 0.5 micrograms IgG per ml) and reacted with hydrazide-activated multiwell plates for at least two hours at room temperature. Unbound IgG is removed by washing the multiwell plate with borate buffered saline or another suitable buffer. The plate may be dried for storage, if desired. A similar protocol may be followed for microbeads if the material of the microbead is suitable for such attachment.

In some embodiments, the solid support is a microtiter plate. In some embodiments, the solid support is a paramagnetic bead. An exemplary paramagnetic bead is Streptavidin C1 (Dynal, 650.01-03). Other suitable beads will be apparent to those of skill in the art. Methods for attachment of antibodies to paramagnetic beads are well-known in the art. One example is given in the Examples.

The cardiac troponin of interest is contacted with the capture binding partner, e.g., capture antibody immobilized on a solid support. Some sample preparation may be used; e.g., preparation of serum from blood samples or concentration procedures before the sample is contacted with the capture antibody. Protocols for binding of proteins in immunoassays are well-known in the art and are included in the Examples.

The time allowed for binding will vary depending on the conditions; it will be apparent that shorter binding times are desirable in some settings, especially in a clinical setting. The use of, e.g., paramagnetic beads can reduce the time required for binding. In some embodiments, the time allowed for binding of the protein of interest to the capture binding partner, e.g., antibody, is less that about 12, 10, 8, 6, 4, 3, 2, or 1 hours, or less than about 60, 50, 40, 30, 25, 20, 15, 10, or 5 minutes. In some embodiments, the time allowed for binding of the protein of interest to the capture binding partner, e.g., antibody, is less than about 60 minutes. In some embodiments, the time allowed for binding of the protein of interest to the capture binding partner, e.g., antibody, is less that about 40 minutes. In some embodiments, the time allowed for binding of the protein of interest to the capture binding partner, e.g., antibody, is less that about 30 minutes. In some embodiments, the time allowed for binding of the protein of interest to the capture binding partner, e.g., antibody, is less that about 20 minutes. In some embodiments, the time allowed for binding of the protein of interest to the capture binding partner, e.g., antibody, is less that about 15 minutes. In some embodiments, the time allowed for binding of the protein of interest to the capture binding partner, e.g., antibody, is less that about 10 minutes. In some embodiments, the time allowed for binding of the protein of interest to the capture binding partner, e.g., antibody, is less that about 5 minutes.

In some embodiments, following the binding of the troponin particles to the capture binding partner, e.g., capture antibody, particles that may have bound nonspecifically, as well as other unwanted substances in the sample, are washed away leaving substantially only specifically bound troponin particles. In other embodiments, no wash is used between additions of sample and label; it will be appreciated that this reduces sample preparation time even further. Thus, in some embodiments, the time allowed for both binding of the protein of interest to the capture binding partner, e.g., antibody, and binding of the label to the protein of interest, is less that about 12, 10, 8, 6, 4, 3, 2, or 1 hours, or less than about 60, 50, 40, 30, 25, 20, 15, 10, or 5 minutes. In some embodiments, the time allowed for both binding of the protein of interest to the capture binding partner, e.g., antibody, and binding of the label to the protein of interest, is less that about 60 minutes. In some embodiments, the time allowed for both binding of the protein of interest to the capture binding partner, e.g., antibody, and binding of the label to the protein of interest, is less than about 40 minutes. In some embodiments, the time allowed for both binding of the protein of interest to the capture binding partner, e.g., antibody, and binding of the label to the protein of interest, is less about 30 minutes. In some embodiments, the time allowed for both binding of the protein of interest to the capture binding partner, e.g., antibody, and binding of the label to the protein of interest, is less than about 20 minutes. In some embodiments, the time allowed for both binding of the protein of interest to the capture binding partner, e.g., antibody, and binding of the label to the protein of interest, is less than about 15 minutes. In some embodiments, the time allowed for both binding of the protein of interest to the capture binding partner, e.g., antibody, and binding of the label to the protein of interest, is less than about 10 minutes. In some embodiments, the time allowed for both binding of the protein of interest to the capture binding partner, e.g., antibody, and binding of the label to the protein of interest, is less than about 5 minutes.

Some immunoassay diagnostic reagents including the capture and signal antibodies used to measure the target analytes may be derived from the sera of animals. Endogenous human heterophilic antibodies, or human anti-animal antibodies, which have the ability to bind to immunoglobulins of other species, are present in the serum or plasma of more than 10% of patients. These circulating heterophile antibodies may interfere with immunoassay measurements. In sandwich immunoassays, these heterophilic antibodies can either bridge the capture and detection (diagnostic) antibodies, thereby producing a false-positive signal, or they may block the binding of the diagnostic antibodies, thereby producing a false-negative signal. In competitive immunoassays, the heterophile antibodies may bind to the analytic antibody and inhibit its binding to the troponin. They also may either block or augment the separation of the antibody-troponin complex from free troponin, especially when antispecies antibodies are used in the separation systems. Therefore, the impact of these heterophile antibody interferences are difficult to predict. Thus, it would be advantageous to block the binding of any heterophilic antibodies. In some embodiments of the invention, the immunoassay includes the step of depleting the sample of heterophile antibodies using one or more heterophile antibody blockers. Methods for removing heterophile antibodies from samples that are to be tested in immunoassays are known and include: heating the specimen in a sodium acetate buffer, pH 5.0, for 15 minutes at 90° C. and centrifuging at 1200 g for 10 minutes, or the heterophile antibodies can be precipitated using polyethylene glycol (PEG); immunoextracting the interfering heterophile immunoglobulins from the specimen using protein A or protein G; or adding nonimmune mouse IgG. Embodiments of the methods of the invention contemplate preparing the sample prior to analysis with the single molecule detector. The appropriateness of the method of pretreatment may be determined. Biochemicals to minimize immunoassay interference caused by heterophile antibodies are commercially available. For example, a product called MAK33, which is an IgG1 monoclonal antibody to h-CK-MM, may be obtained from Boehringer Mannheim. The MAK33 plus product contains a combination of IgG1 and IgG1-Fab. The polyMAK33 contains IgG1-Fab polymerized with IgG1, and the polyMAC 2b/2a contains IgG2a-Fab polymerized with IgG2b. A second commercial source of biochemicals to neutralize heterophile antibodies is Immunoglobulin Inhibiting Reagent marketed by Bioreclamation Inc, East Meadow, N.Y. This product is a preparation of immunoglobulins (IgG and IgM) from multiple species, mainly murine IgG2a, IgG2b, and IgG3 from Balb/c mice. In some embodiments the heterophile antibody may be immunoextracted from the sample using methods known in the art e.g. depleting the sample of the heterophile antibody by binding the interfering antibody to protein A or G. In some embodiments, the heterophile antibody is neutralized using one or more heterophile antibody blockers. Heterophile blockers may be selected from the group consisting of anti-isotype heterophile antibody blockers, anti-idiotype heterophile antibody blockers, and anti-anti-idiotype heterophile antibody blockers. In some embodiments a combination of heterophile antibody blockers may be used.

Label is added either with or following the addition of sample and washing. Protocols for binding of antibody and other immunolabels to proteins and other molecules are well-known in the art. If the label binding step is separate from capture binding, the time allowed for label binding can be important, e.g., in the clinical setting. In some embodiments, the time allowed for binding of the protein of interest to the label, e.g., antibody-dye, is less than about 12, 10, 8, 6, 4, 3, 2, or 1 hours, or less than about 60, 50, 40, 30, 25, 20, 15, 10, or 5 minutes. In some embodiments, the time allowed for binding of the protein of interest to the label, e.g., antibody-dye, is less than about 60 minutes. In some embodiments, the time allowed for binding of the protein of interest to the label, e.g., antibody-dye, is less than about 40 minutes. In some embodiments, the time allowed for binding of the protein of interest to the label, e.g., antibody-dye, is less than about 30 minutes. In some embodiments, the time allowed for binding of the protein of interest to the label, e.g., antibody-dye, is less than about 20 minutes. In some embodiments, the time allowed for binding of the protein of interest to the label, e.g., antibody-dye, is less than about 15 minutes. In some embodiments, the time allowed for binding of the protein of interest to the label, e.g., antibody-dye, is less than about 10 minutes. In some embodiments, the time allowed for binding of the protein of interest to the label, e.g., antibody-dye, is less than about 5 minutes. Excess label is removed by washing.

Label is then eluted from the protein of interest. Preferred elution buffers are effective in releasing the label without generating significant background. It is also useful if the elution buffer is bacteriostatic. Elution buffers of use in the invention include a chaotrope, e.g., urea or a guanidinium compound; a buffer, e.g., borate buffered saline; a protein carrier, e.g., an albumin, such as human, bovine, or fish albumin, or an IgG, to coat the wall of the capillary tube in the detection instrument; and a surfactant, e.g., an ionic or non-ionic detergent, selected so as to produce a relatively low background, e.g., Tween 20, Triton X-100, or SDS.

The elution buffer/label aliquot that is sampled into the single molecule detector is referred to as the "processing sample," to distinguish it from the original sample which was obtained from an individual.

In another embodiment, the solid phase binding assay may employ a competitive binding assay format. One such method comprises a) competitively binding to a capture antibody immobilized on a binding surface i) a troponin particle in a sample and ii) a labeled analog of the troponin particle comprising a detectable label (the detection reagent) and b) measuring the amount of the label using a single particle analyzer. Another such method comprises a) competitively binding to an antibody having a detectable label (the detection reagent) i) a troponin particle in a sample and ii) an analog of troponin particle that is immobilized on a binding surface (the capture reagent) and b) measuring the amount of the label using a single particle analyzer. An "analog of a troponin" refers, herein, to a species that competes with troponin for binding to a capture antibody. Examples of competitive immunoassays are disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

C. Detection of Troponin and Determination of Concentration

Following elution, the label is run through a single molecule detector in e.g., the elution buffer. A processing sample may contain no label, a single label, or a plurality of labels. The number of labels corresponds or is proportional to (if dilutions or fractions of samples are used) the number of molecules of cardiac troponin captured during the capture step.

Any suitable single molecule detector capable of detecting the label used with the protein of interest may be used. Suitable single molecule detectors are described herein. Typically the detector will be part of a system that includes an automatic sampler for sampling prepared samples, and, optionally, a recovery system to recover samples.

In some embodiments, the processing sample is analyzed in a single molecule analyzer that utilizes a capillary flow system, and that includes a capillary flow cell, a laser to illuminate an interrogation space in the capillary through which processing sample is passed, a detector to detect radiation emitted from the interrogation space, and a source of motive force to move a processing sample through the interrogation space. In some embodiments, the single molecule analyzer further comprises a microscope objective lens that collects light emitted from processing sample as it passes through the interrogation space, e.g., a high numerical aperture microscope objective. In some embodiments, the laser and detector are in a confocal arrangement. In some embodiments, the laser is a continuous wave laser. In some embodiments, the detector is a avalanche photodiode detector. In some embodiments, the source of motive force is a pump to provide pressure. In some embodiments, the invention provides an analyzer system that includes a sampling system capable of automatically sampling a plurality of samples providing a fluid communication between a sample container and the interrogation space. In some embodiments, the interrogation space has a volume of between about 0.001 and 500 pL, or between about 0.01 pL and 100 pL, or between about 0.01 pL and 10 pL, or between about 0.01 pL and 5 pL, or between about 0.01 pL and 0.5 pL, or between about 0.02 pL and about 300 pL, or between about 0.02 pL and about 50 pL or between about 0.02 pL and about 5 pL or between about 0.02 pL and about 0.5 pL or between about 0.02 pL and about 2 pL, or between about 0.05 pL and about 50 pL, or between about 0.05 pL and about 5 pL, or between about 0.05 pL and about 0.5 pL, or between about 0.05 pL and about 0.2 pL, or between about 0.1 pL and about 25 pL. In some embodiments, the interrogation space has a volume between about 0.004 pL and 100 pL. In some embodiments, the interrogation space has a volume between about 0.02 pL and 50 pL. In some embodiments, the interrogation space has a volume between about 0.001 pL and 10 pL. In some embodiments, the interrogation space has a volume between about 0.001 pL and 10 pL. In some embodiments, the interrogation space has a volume between about 0.01 pL and 5 pL. In some embodiments, the interrogation space has a volume between about 0.02 pL and about 5 pL. In some embodiments, the interrogation space has a volume between about 0.05 pL and 5 pL. In some embodiments, the interrogation space has a volume between about 0.05 pL and 10 pL. In some embodiments, the interrogation space has a volume between about 0.5 pL and about 5 pL. In some embodiments, the interrogation space has a volume between about 0.02 pL and about 0.5 pL.

In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space, an avalanche photodiode detector to detect radiation emitted from the interrogation space, and a pump to provide pressure to move a processing sample through the interrogation space, where the interrogation space is between about 0.02 pL and about 50 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.004 pL and about 100 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.05 pL and about 10 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.05 pL and about 5 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.5 pL and about 5 pL.

In some embodiments, the single molecule detector is capable of determining a concentration for a molecule of interest in a sample where sample may range in concentration over a range of at least about 100-fold, or 1000-fold, or 10,000-fold, or 100,000-fold, or 300,00-fold, or 1,000,000-fold, or 10,000,000-fold, or 30,000,000-fold.

In some embodiments, the methods of the invention utilize a single molecule detector capable detecting a difference of less than about 50%, 40%, 30%, 20%, 15%, or 10% in concentration of an analyte between a first sample and a second sample that are introduced into the detector, where the volume of the first sample and said second sample introduced into the analyzer is less than about 100, 90, 80, 70, 60, 50, 40, 30, 20, 15, 10, 5, 4, 3, 2, or 1 ul, and wherein the analyte is present at a concentration of less than about 100, 90, 80, 70, 60, 50, 40, 30, 20, 15, 10, 5, 4, 3, 2, or 1 femtomolar. In some embodiments, the methods of the invention utilize a single molecule detector capable detecting a difference of less than about 50% in concentration of an analyte between a first sample and a second sample that are introduced into the detector, where the volume of the first sample and said second sample introduced into the analyzer is less than about 100 ul, and wherein the analyte is present at a concentration of less than about 100 femtomolar. In some embodiments, the methods of the invention utilize a single molecule detector capable detecting a difference of less than about 40% in concentration of an analyte between a first sample and a second sample that are introduced into the detector, where the volume of the first sample and said second sample introduced into the analyzer is less than about 50 ul, and wherein the analyte is present at a concentration of less than about 50 femtomolar. In some embodiments, the methods of the invention utilize a single molecule detector capable detecting a difference of less than about 20% in concentration of an analyte between a first sample and a second sample that are introduced into the detector, where the volume of the first sample and said second sample introduced into the analyzer is less than about 20 ul, and wherein the analyte is present at a concentration of less than about 20 femtomolar. In some embodiments, the methods of the invention utilize a single molecule detector capable detecting a difference of less than about 20% in concentration of an analyte between a first sample and a second sample that are introduced into the detector, where the volume of the first sample and said second sample introduced into the analyzer is less than about 10 ul, and wherein the analyte is present at a concentration of less than about 10 femtomolar. In some embodiments, the methods of the invention utilize a single molecule detector capable detecting a difference of less than about 20% in concentration of an analyte between a first sample and a second sample that are introduced into the detector, where the volume of the first sample and said second sample introduced into the analyzer is less than about 5 ul, and wherein the analyte is present at a concentration of less than about 5 femtomolar.

The single molecule detector and systems are described in more detail below. Further embodiments of single molecule analyzers useful in the methods of the invention, such as detectors with more than one interrogation window, detectors utilize electrokinetic or electrophoretic flow, and the like, may be found in U.S. patent application Ser. No. 11/048,660, incorporated by reference herein in its entirety.

Between runs the instrument may be washed. A wash buffer that maintains the salt and surfactant concentrations of the sample may be used in some embodiments to maintain the conditioning of the capillary; i.e., to keep the capillary surface relatively constant between samples to reduce variability.

A feature that contributes to the extremely high sensitivity of the instruments and methods of the invention is the method of detecting and counting labels, which, in some embodiments, are attached to single molecules to be detected or, more typically, correspond to a single molecule to be detected. Briefly, the processing sample flowing through the capillary is effectively divided into a series of detection events, by subjecting a given interrogation space of the capillary to EM radiation from a laser that emits light at an appropriate excitation wavelength for the fluorescent moiety used in the label for a predetermined period of time, and detecting photons emitted during that time. Each predetermined period of time is a "bin." If the total number of photons detected in a given bin exceeds a predetermined threshold level, a detection event is registered for that bin, i.e., a label has been detected. If the total number of photons is not at the predetermined threshold level, no detection event is registered. In some embodiments, processing sample concentration is dilute enough that, for a large percentage of detection events, the detection event represents only one label passing through the window, which corresponds to a single molecule of interest in the original sample, that is, few detection events represent more than one label in a single bin. In some embodiments, further refinements are applied to allow greater concentrations of label in the processing sample to be detected accurately, i.e., concentrations at which the probability of two or more labels being detected as a single detection event is no longer insignificant.

Although other bin times may be used without departing from the scope of the present invention, in some embodiments the bin times are selected in the range of about 1 microsecond to about 5 ms. In some embodiments, the bin time is more than about 1, 2, 3, 4, 5, 6, 7, 8, 9, 10, 15, 20, 30, 40, 50, 60, 70, 80, 90, 100, 200, 250, 300, 400, 500, 600, 700, 750, 800, 900, 1000, 2000, 3000, 4000, or 5000 microseconds. In some embodiments, the bin time is less than about 2, 3, 4, 5, 6, 7, 8, 9, 10, 15, 20, 30, 40, 50, 60, 70, 80, 90, 100, 200, 250, 300, 400, 500, 600, 700, 750, 800, 900, 1000, 2000, 3000, 4000, or 5000 microseconds. In some embodiments, the bin time is about 1 to 1000 microseconds. In some embodiments, the bin time is about 1 to 750 microseconds. In some embodiments, the bin time is about 1 to 500 microseconds. In some embodiments, the bin time is about 1 to 250 microseconds. In some embodiments, the bin time is about 1 to 100 microseconds. In some embodiments, the bin time is about 1 to 50 microseconds. In some embodiments, the bin time is about 1 to 40 microseconds. In some embodiments, the bin time is about 1 to 30 microseconds. In some embodiments, the bin time is about 1 to 500 microseconds. In some embodiments, the bin time is about 1 to 20 microseconds. In some embodiments, the bin time is about 1 to 10 microseconds. In some embodiments, the bin time is about 1 to 500 microseconds. In some embodiments, the bin time is about 1 to 5 microseconds. In some embodiments, the bin time is about 5 to 500 microseconds. In some embodiments, the bin time is about 5 to 250 microseconds. In some embodiments, the bin time is about 5 to 100 microseconds. In some embodiments, the bin time is about 5 to 50 microseconds. In some embodiments, the bin time is about 5 to 20 microseconds. In some embodiments, the bin time is about 5 to 10 microseconds. In some embodiments, the bin time is about 10 to 500 microseconds. In some embodiments, the bin time is about 10 to 250 microseconds. In some embodiments, the bin time is about 10 to 100 microseconds. In some embodiments, the bin time is about 10 to 50 microseconds. In some embodiments, the bin time is about 10 to 30 microseconds. In some embodiments, the bin time is about 10 to 20 microseconds. In some embodiments, the bin time is about 5 microseconds. In some embodiments, the bin time is about 5 microseconds. In some embodiments, the bin time is about 6 microseconds. In some embodiments, the bin time is about 7 microseconds. In some embodiments, the bin time is about 8 microseconds. In some embodiments, the bin time is about 9 microseconds. In some embodiments, the bin time is about 10 microseconds. In some embodiments, the bin time is about 11 microseconds. In some embodiments, the bin time is about 12 microseconds. In some embodiments, the bin time is about 13 microseconds. In some embodiments, the bin time is about 14 microseconds. In some embodiments, the bin time is about 5 microseconds. In some embodiments, the bin time is about 15 microseconds. In some embodiments, the bin time is about 16 microseconds. In some embodiments, the bin time is about 17 microseconds. In some embodiments, the bin time is about 18 microseconds. In some embodiments, the bin time is about 19 microseconds. In some embodiments, the bin time is about 20 microseconds. In some embodiments, the bin time is about 25 microseconds. In some embodiments, the bin time is about 30 microseconds. In some embodiments, the bin time is about 40 microseconds. In some embodiments, the bin time is about 50 microseconds. In some embodiments, the bin time is about 100 microseconds. In some embodiments, the bin time is about 250 microseconds. In some embodiments, the bin time is about 500 microseconds. In some embodiments, the bin time is about 750 microseconds. In some embodiments, the bin time is about 1000 microseconds.

In some embodiments, the background noise level is determined from the mean noise level, or the root-mean-square noise. In other cases, a typical noise value or a statistical value is chosen. In most cases, the noise is expected to follow a Poisson distribution. Thus, in some embodiments, determining the concentration of a particle-label complex in a sample comprises determining the background noise level.

Thus, as a label flows through the capillary flow cell, it is irradiated by the laser beam to generate a burst of photons. The photons emitted by the label are discriminated from background light or background noise emission by considering only the bursts of photons that have energy above a predetermined threshold energy level which accounts for the amount of background noise that is present in the sample. Background noise typically comprises low frequency emission produced, for example, by the intrinsic fluorescence of non-labeled particles that are present in the sample, the buffer or diluent used in preparing the sample for analysis, Raman scattering and electronic noise. In some embodiments, the value assigned to the background noise is calculated as the average background signal noise detected in a plurality of bins, which are measurements of photon signals that are detected in an interrogation space during a predetermined length of time. Thus in some embodiments, background noise is calculated for each sample as a number specific to that sample.

Given the value for the background noise, the threshold energy level can be assigned. As discussed above, the threshold value is determined to discriminate true signals (due to fluorescence of a label) from the background noise. Care must be taken in choosing a threshold value such that the number of false positive signals from random noise is minimized while the number of true signals which are rejected is also minimized. Methods for choosing a threshold value include determining a fixed value above the noise level and calculating a threshold value based on the distribution of the noise signal. In one embodiment, the threshold is set at a fixed number of standard deviations above the background level. Assuming a Poisson distribution of the noise, using this method one can estimate the number of false positive signals over the time course of the experiment. In some embodiments, the threshold level is calculated as a value of 4 sigma above the background noise. For example, given an average background noise level of 200 photons, the analyzer system establishes a threshold level of $4\sqrt{200}$ above the average background/noise level of 200 photons to be 256 photons. Thus, in some embodiments, determining the concentration of a label in a sample includes establishing the threshold level above which photon signals represent the presence of a label. Conversely, photon signals that have an energy level that is not greater than that of the threshold level indicate the absence of a label.

Many bin measurements are taken to determine the concentration of a sample, and the absence or presence of a label is ascertained for each bin measurement. Typically, 60,000 measurements or more can made in one minute (e.g., in embodiments in which the bin size is 1 ms—for smaller bin sizes the number of measurements is correspondingly larger, e.g., 6,000,000 measurements per minute for a bin size of 10 microseconds). Thus, no single measurement is crucial and the method provides for a high margin of error. The bins that are determined not to contain a label ("no" bins) are discounted and only the measurements made in the bins that are determined to contain label ("yes" bins) are accounted in determining the concentration of the label in the processing sample. Discounting measurements made in the "no" bins or bins that are devoid of label increases the signal to noise ratio and the accuracy of the measurements. Thus, in some embodiments, determining the concentration of a label in a sample comprises detecting the bin measurements that reflect the presence of a label.

The signal to noise ratio or the sensitivity of the analyzer system can be increased by minimizing the time that background noise is detected during a bin measurement in which a particle-label complex is detected. For example, in a bin measurement lasting 1 millisecond during which one particle-label complex is detected when passing across an interrogation space within 250 microseconds, 750 microseconds of the 1 millisecond are spent detecting background noise emission. The signal to noise ratio can be improved by decreasing the bin time. In some embodiments, the bin time is 1 millisecond. In other embodiments, the bin time is 750, 500, 250 microseconds, 100 microseconds, 50 microseconds, 25 microseconds or 10 microseconds. Other bin times are as described herein.

Other factors that affect measurements are the brightness or dimness of the fluorescent moiety, the flow rate, and the power of the laser. Various combinations of the relevant factors that allow for detection of label will be apparent to those of skill in the art. In some embodiments, the bin time is adjusted without changing the flow rate. It will be appreciated by those of skill in the art that as bin time decreases, laser power output directed at the interrogation space must increase to maintain a constant total energy applied to the interrogation space during the bin time. For example, if bin time is decreased from 1000 microseconds to 250 microseconds, as a first approximation, laser power output must be increased approximately four-fold. These settings allow for the detection of the same number of photons in a 250 μs as the number of photons counted during the 1000 μs given the previous settings, and allow for faster analysis of sample with lower backgrounds and thus greater sensitivity. In addition, flow rates may be adjusted in order to speed processing of sample. These numbers are merely exemplary, and the skilled practitioner can adjust the parameters as necessary to achieve the desired result.

In some embodiments, the interrogation space encompasses the entire cross-section of the sample stream. When the interrogation space encompasses the entire cross-section of the sample stream, only the number of labels counted and the volume passing through a cross-section of the sample stream in a set length of time are needed to calculate the concentration of the label in the processing sample. In some embodiments, the interrogation space can be defined to be smaller than the cross-sectional area of sample stream by, for example, the interrogation space is defined by the size of the spot illuminated by the laser beam. In some embodiments, the interrogation space can be defined by adjusting the apertures 306 (FIG. 1A) or 358 and 359 (FIG. 1B) of the analyzer and reducing the illuminated volume that is imaged by the objective lens to the detector. In the embodiments when the interrogation space is defined to be smaller than the cross-sectional area of sample stream, the concentration of the label can be determined by interpolation of the signal emitted by the complex from a standard curve that is generated using one or more samples of known standard concentrations. In yet other embodiments, the concentration of the label can be determined by comparing the measured particles to an internal label standard. In embodiments when a diluted sample is analyzed, the dilution factor is accounted in calculating the concentration of the molecule of interest in the starting sample.

As discussed above, when the interrogation space encompasses the entire cross-section of the sample stream, only the number of labels counted passing through a cross-section of the sample stream in a set length of time (bin) and the volume of sample that was interrogated in the bin are needed to calculate the concentration the sample. The total number of labels contained in the "yes" bins is determined and related to the sample volume represented by the total number of bins used in the analysis to determine the concentration of labels in the processing sample. Thus, in one embodiment, determining the concentration of a label in a processing sample comprises determining the total number of labels detected "yes" bins and relating the total number of detected labels to the total sample volume that was analyzed. The total sample volume that is analyzed is the sample volume that is passed through the capillary flow cell and across the interrogation space in a specified time interval. Alternatively, the concentration of the label complex in a sample is determined by interpolation of the signal emitted by the label in a number of bins from a standard curve that is generated by determining the signal emitted by labels in the same number of bins by standard samples containing known concentrations of the label.

In some embodiments, the number of individual labels that are detected in a bin is related to the relative concentration of the particle in the processing sample. At relatively low concentrations, for example at concentrations below about 10-16 M the number of labels is proportional to the photon signal that is detected in a bin. Thus, at low concentrations of label the photon signal is provided as a digital signal. At relatively higher concentrations, for example at concentrations greater than about 10-16 M, the proportionality of photon signal to a label is lost as the likelihood of two or more labels crossing the interrogation space at about the same time and being counted as one becomes significant. Thus, in some embodiments, individual particles in a sample of a concentration greater than about $10^{-16}$ M are resolved by decreasing the length of time of the bin measurement.

Alternatively, in other embodiments, the total the photon signal that is emitted by a plurality of particles that are present in any one bin is detected. These embodiments allow for single molecule detectors of the invention wherein the dynamic range is at least 3, 3.5, 4, 4.5, 5.5, 6, 6.5, 7, 7.5, 8, or more than 8 logs.

"Dynamic range," as that term is used herein, refers to the range of sample concentrations that may be quantitated by the instrument without need for dilution or other treatment to alter the concentration of successive samples of differing concentrations, where concentrations are determined with an accuracy appropriate for the intended use. For example, if a microtiter plate contains a sample of 1 femtomolar concentration for an analyte of interest in one well, a sample of 10,000 femtomolar concentration for an analyte of interest in another well, and a sample of 100 femtomolar concentration for the analyte in a third well, an instrument with a dynamic range of at least 4 logs and a lower limit of quantitation of 1 femtomolar is able to accurately quantitate the concentration of all the samples without the need for further treatment to adjust concentration, e.g., dilution. Accuracy may be determined by standard methods, e.g., using a series of standards of concentrations that span the dynamic range and constructing a standard curve. Standard measures of fit of the resulting standard curve may be used as a measure of accuracy, e.g., an $r^2$ greater than about 0.7, 0.75, 0.8, 0.85, 0.9, 0.91, 0.92, 0.93, 0.94, 0.95, 0.96, 0.97, 0.98, or 0.99.

Increased dynamic range is achieved by altering the manner in which data from the detector is analyzed, and/or by the use of an attenuator between the detector and the interrogation space. At the low end of the range, where processing sample is sufficiently dilute that each detection event, i.e., each burst of photons above a threshold level in a bin (the "event photons"), likely represents only one label, the data is analyzed to count detection events as single molecules. I.e., each bin is analyzed as a simple "yes" or "no" for the presence of label, as described above. For a more concentrated processing sample, where the likelihood of two or more labels occupying a single bin becomes significant, the number of event photons in a significant number of bins is found to be substantially greater than the number expected for a single label, e.g., the number of event photons in a significant number of bins corresponds to two-fold, three-fold, or more, than the number of event photons expected for a single label. For these samples, the instrument changes its method of data analysis to one of integrating the total number of event photons for the bins of the processing sample. This total will be proportional to the total number of labels that were in all the bins. For an even more concentrated processing sample, where many labels are present in most bins, background noise becomes an insignificant portion of the total signal from each bin, and the instrument changes its method of data analysis to one of counting total photons per bin (including background). An even further increase in dynamic range can be achieved by the use of an attenuator between the flow cell and the detector, when concentrations are such that the intensity of light reaching the detector would otherwise exceed the capacity of the detector for accurately counting photons, i.e., saturate the detector.

The instrument may include a data analysis system that receives input from the detector and determines the appropriate analysis method for the sample being run, and outputs values based on such analysis. The data analysis system may further output instructions to use or not use an attenuator, if an attenuator is included in the instrument.

By utilizing such methods, the dynamic range of the instrument can be dramatically increased. Thus, in some embodiments, the instrument is capable of measuring concentrations of samples over a dynamic range of more than about 1000 (3 log), 10,000 (4 log), 100,000 (5 log), 350,000 (5.5 log), 1,000,000 (6 log), 3,500,000 (6.5 log), 10,000,000 (7 log), 35,000,000 (7.5 log), or 100,000,000 (8 log). In some embodiments, the instrument is capable of measuring concentrations of samples over a dynamic range of more than about 100,000 (5 log). In some embodiments, the instrument is capable of measuring concentrations of samples over a dynamic range of more than about 1,000,000 (6 log). In some embodiments, the instrument is capable of measuring concentrations of samples over a dynamic range of more than about 10,000,000 (7 log). In some embodiments, the instrument is capable of measuring the concentrations of samples over a dynamic range of from about 1-10 femtomolar to at least about 1000; 10,000; 100,000; 350,000; 1,000,000; 3,500,000; 10,000,000, or 35,000,000 femtomolar. In some embodiments, the instrument is capable of measuring the concentrations of samples over a dynamic range of from about 1-10 femtomolar to at least about 10,000 femtomolar. In some embodiments, the instrument is capable of measuring the concentrations of samples over a dynamic range of from about 1-10 femtomolar to at least about 100,000 femtomolar. In some embodiments, the instrument is capable of measuring the concentrations of samples over a dynamic range of from about 1-10 femtomolar to at least about 1,000,000 femtomolar. In some embodiments, the instrument is capable of measuring the concentrations of samples over a dynamic range of from about 1-10 femtomolar to at least about 10,000,000.

In some embodiments, an analyzer or analyzer system of the invention is capable of detecting an analyte, e.g., a biomarker at a limit of detection of less than 1 nanomolar, or 1 picomolar, or 1 femtomolar, or 1 attomolar, or 1 zeptomolar. In some embodiments, the analyzer or analyzer system is capable of detecting a change in concentration of the analyte, or of multiple analytes, e.g., a biomarker or biomarkers, from one sample to another sample of less than about 0.1, 1, 2, 5, 10, 20, 30, 40, 50, 60, or 80% when the biomarker is present at a concentration of less than 1 nanomolar, or 1 picomolar, or 1 femtomolar, or 1 attomolar, or 1 zeptomolar, in the samples, and when the size of each of the sample is less than about 100, 50, 40, 30, 20, 10, 5, 2, 1, 0.1, 0.01, 0.001, or 0.0001 ul. In some embodiments, the analyzer or analyzer system is capable of detecting a change in concentration of the analyte from a first sample to a second sample of less than about 20%, when the analyte is present at a concentration of less than about 1 picomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 100 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 50 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 5 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 5 femtomolar, and when the size of each of the samples is less than about 5 µl. In some embodiments, the analyzer or analyzer system is capable of detecting a change in concentration of the analyte from a first sample to a second sample of less than about 20%, when the analyte is present at a concentration of less than about 1 femtomolar, and when the size of each of the samples is less than about 5 µl.

V. Instruments and Systems Suitable for Highly Sensitive Analysis of Troponin

The methods of the invention utilize analytical instruments of high sensitivity, e.g., single molecule detectors. Such single molecule detectors include embodiments as hereinafter described.

A. Apparatus/System

In one aspect, the methods described herein utilize an analyzer system capable of detecting a single particle in a sample. In one embodiment, the analyzer system is capable of single particle detection of a fluorescently labeled particle wherein the analyzer system detects energy emitted by an excited fluorescent label in response to exposure by an electromagnetic radiation source when the single particle is present in an interrogation space defined within a capillary flow cell fluidly connected to the sampling system of the analyzer system. In a further embodiment of the analyzer system, the single particle moves through the interrogation space of the capillary flow cell by means of a motive force. In another embodiment of the analyzer system, an automatic sampling system may be included in the analyzer system for introducing the sample into the analyzer system. In another embodiment of the analyzer system, a sample preparation system may be included in the analyzer system for preparing a sample. In a further embodiment, the analyzer system may contain a sample recovery system for recovering at least a portion of the sample after analysis is complete.

In one aspect, the analyzer system consists of an electromagnetic radiation source for exciting a single particle labeled with a fluorescent label. In one embodiment, the electromagnetic radiation source of the analyzer system is a laser. In a further embodiment, the electromagnetic radiation source is a continuous wave laser.

In a typical embodiment, the electromagnetic radiation source excites a fluorescent moiety attached to a label as the label passes through the interrogation space of the capillary flow cell. In some embodiments, the fluorescent label moiety includes one or more fluorescent dye molecules. In some embodiments, the fluorescent label moiety is a quantum dot. Any fluorescent moiety as described herein may be used in the label.

A label is exposed to electromagnetic radiation when the label passes through an interrogation space located within the capillary flow cell. The interrogation space is typically fluidly connected to a sampling system. In some embodiments the label passes through the interrogation space of the capillary flow cell due to a motive force to advance the label through the analyzer system. The interrogation space is positioned such that it receives electromagnetic radiation emitted from the radiation source. In some embodiments, the sampling system is an automated sampling system capable of sampling a plurality of samples without intervention from a human operator.

The label passes through the interrogation space and emits a detectable amount of energy when excited by the electromagnetic radiation source. In one embodiment, an electromagnetic radiation detector is operably connected to the interrogation space. The electromagnetic radiation detector is capable of detecting the energy emitted by the label, e.g., by the fluorescent moiety of the label.

In a further embodiment of the analyzer system, the system further includes a sample preparation mechanism where a sample may be partially or completely prepared for analysis by the analyzer system. In some embodiments of the analyzer system, the sample is discarded after it is analyzed by the system. In other embodiments, the analyzer system further includes a sample recovery mechanism whereby at least a portion, or alternatively all or substantially all, of the sample may be recovered after analysis. In such an embodiment, the sample can be returned to the origin of the sample. In some embodiments, the sample can be returned to microtiter wells on a sample microtiter plate. The analyzer system typically further consists of a data acquisition system for collecting and reporting the detected signal.

B. Single Particle Analyzer

As shown in FIG. 1A, described herein is one embodiment of an analyzer system 300. The analyzer system 300 includes an electromagnetic radiation source 301, a mirror 302, a lens 303, a capillary flow cell 313, a microscopic objective lens 305, an aperture 306, a detector lens 307, a detector filter 308, a single photon detector 309, and a processor 310 operatively connected to the detector.

Figure 2A:
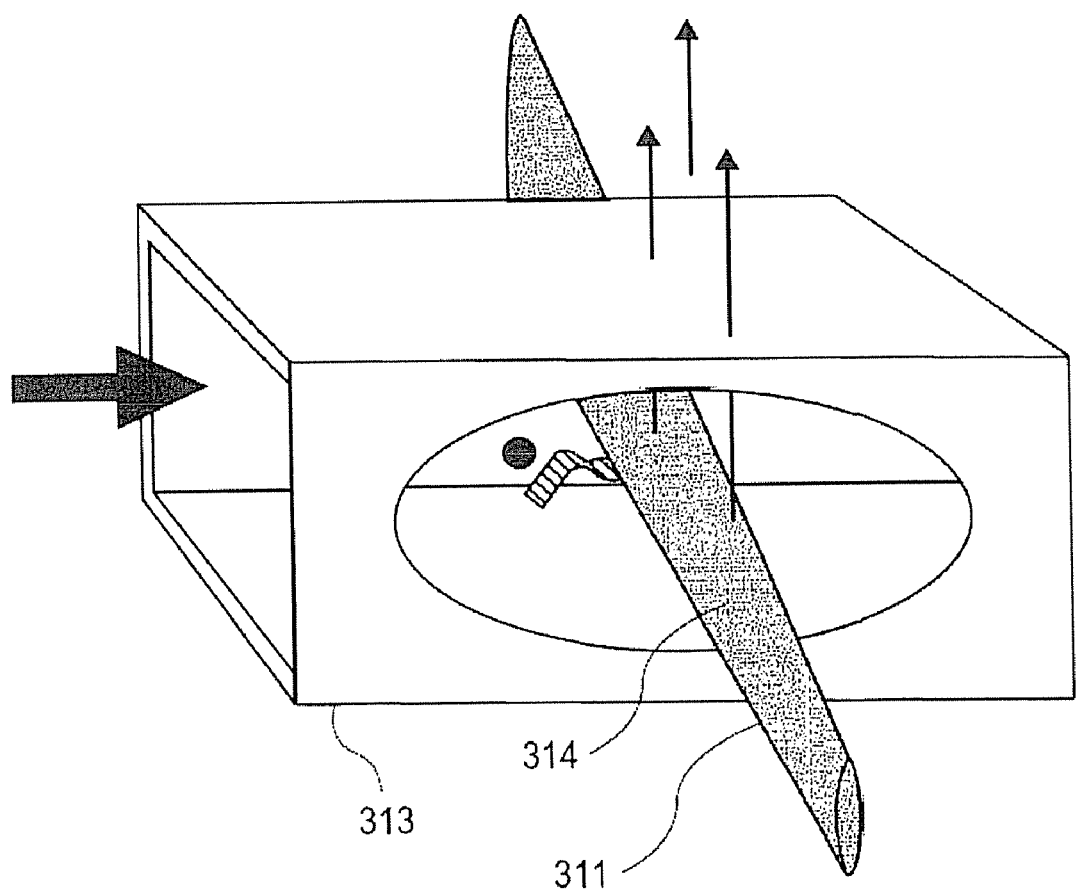
FIGS. 2A and 2B. Schematic diagrams of a capillary flow cell for a single particle analyzer.

In operation the electromagnetic radiation source 301 is aligned so that its output 311 is reflected off of a front surface 312 of mirror 302. The lens 303 focuses the beam 311 onto a single interrogation space (an illustrative example of an interrogation space 314 is shown in FIG. 2A) in the capillary flow cell 313. The microscope objective lens 305 collects light from sample particles and forms images of the beam onto the aperture 306. The aperture 306 affects the fraction of light emitted by the specimen in the interrogation space of the capillary flow cell 313 that can be collected. The detector lens 307 collects the light passing through the aperture 306 and focuses the light onto an active area of the detector 309 after it passes through the detector filters 308. The detector filters 308 minimize aberrant noise signals due to light scatter or ambient light while maximizing the signal emitted by the excited fluorescent moiety bound to the particle. The processor 310 processes the light signal from the particle according to the methods described herein.

In one embodiment, the microscope objective lens 305 is a high numerical aperture microscope objective. As used herein, "high numerical aperture lens" include a lens with a numerical aperture of equal to or greater than 0.6. The numerical aperture is a measure of the number of highly diffracted image-forming light rays captured by the objective. A higher numerical aperture allows increasingly oblique rays to enter the objective lens and thereby produce a more highly resolved image. Additionally, the brightness of an image increases with a higher numerical aperture. High numerical aperture lenses are commercially available from a variety of vendors, and any one lens having a numerical aperture of equal to or greater than approximately 0.6 may be used in the analyzer system. In some embodiments, the lens has a numerical aperture of about 0.6 to about 1.3. In some embodiments, the lens has a numerical aperture of about 0.6 to about 1.0. In some embodiments, the lens has a numerical aperture of about 0.7 to about 1.2. In some embodiments, the lens has a numerical aperture of about 0.7 to about 1.0. In some embodiments, the lens has a numerical aperture of about 0.7 to about 0.9. In some embodiments, the lens has a numerical aperture of about 0.8 to about 1.3. In some embodiments, the lens has a numerical aperture of about 0.8 to about 1.2. In some embodiments, the lens has a numerical aperture of about 0.8 to about 1.0. In some embodiments, the lens has a numerical aperture of at least about 0.6. In some embodiments, the lens has a numerical aperture of at least about 0.7. In some embodiments, the lens has a numerical aperture of at least about 0.8. In some embodiments, the lens has a numerical aperture of at least about 0.9. In some embodiments, the lens has a numerical aperture of at least about 1.0. In some embodiments, the aperture of the microscope objective lens 305 is approximately 1.25. In an embodiment where a microscope objective lens 305 of 0.8 is used, a Nikon 60X/0.8 NA Achromat lens (Nikon, Inc., USA) can be used.

In some embodiments, the electromagnetic radiation source 301 is a laser that emits light in the visible spectrum. In all embodiments, the electromagnetic radiation source is set such that wavelength of the laser is set such that it is of a sufficient wavelength to excite the fluorescent label attached to the particle. In some embodiments, the laser is a continuous wave laser with a wavelength of 639 nm. In other embodiments, the laser is a continuous wave laser with a wavelength of 532 nm. In other embodiments, the laser is a continuous wave laser with a wavelength of 422 nm. In other embodiments, the laser is a continuous wave laser with a wavelength of 405 nm. Any continuous wave laser with a wavelength suitable for exciting a fluorescent moiety as used in the methods and compositions of the invention may be used without departing from the scope of the invention.

In a single particle analyzer system 300, as each particle passes through the beam 311 of the electromagnetic radiation source, the particle enters into an excited state. When the particle relaxes from its excited state, a detectable burst of light is emitted. The excitation-emission cycle is repeated many times by each particle in the length of time it takes for it to pass through the beam allowing the analyzer system 300 to detect tens to thousands of photons for each particle as it passes through an interrogation space 314. Photons emitted by fluorescent particles are registered by the detector 309 (FIG. 1A) with a time delay indicative of the time for the particle label complex to pass through the interrogation space. The photon intensity is recorded by the detector 309 and sampling time is divided into bins, which are uniform, arbitrary, time segments with freely selectable time channel widths. The number of signals contained in each bin evaluated. One or a combination of several statistical analytical methods are employed in order to determine when a particle is present. Such methods include determining the baseline noise of the analyzer system and setting a signal strength for the fluorescent label at a statistical level above baseline noise to eliminate false positive signals from the detector.

The electromagnetic radiation source 301 is focused onto a capillary flow cell 313 of the analyzer system 300 where the capillary flow cell 313 is fluidly connected to the sample system. An interrogation space 314 is shown in FIG. 2A. The beam 311 from the continuous wave electromagnetic radiation source 301 of FIG. 1A is optically focused to a specified depth within the capillary flow cell 313. The beam 311 is directed toward the sample-filled capillary flow cell 313 at an angle perpendicular to the capillary flow cell 313. The beam 311 is operated at a predetermined wavelength that is selected to excite a particular fluorescent label used to label the particle of interest. The size or volume of the interrogation space 314 is determined by the diameter of the beam 311 together with the depth at which the beam 311 is focused. Alternatively, the interrogation space can be determined by running a calibration sample of known concentration through the analyzer system.

When single molecules are detected in the sample concentration, the beam size and the depth of focus required for single molecule detection are set and thereby define the size of the interrogation space 314. The interrogation space 314 is set such that, with an appropriate sample concentration, only one particle is present in the interrogation space 314 during each time interval over which time observations are made. It will be appreciated that the detection interrogation volume as defined by the beam is not perfectly spherically shaped, and typically is a "bow-tie" shape. However, for the purposes of definition, "volumes" of interrogation spaces are defined herein as the volume encompassed by a sphere of a diameter equal to the focused spot diameter of the beam. The focused spot of the beam 311 may have various diameters without departing from the scope of the present invention. In some embodiments, the diameter of the focused spot of the beam is about 1 to about 5, 10, 15, or 20 microns, or about 5 to about 10, 15, or 20 microns, or about 10 to about 20 microns, or about 10 to about 15 microns. In some embodiments, the diameter of the focused spot of the beam is about 1, 2, 3, 4, 5, 6, 7, 8, 9, 10, 11, 12, 13, 14, 15, 16, 17, 18, 19, or 20 microns. In some embodiments, the diameter of the focused spot of the beam is about 5 microns. In some embodiments, the diameter of the focused spot of the beam is about 10 microns. In some embodiments, the diameter of the focused spot of the beam is about 12 microns. In some embodiments, the diameter of the focused spot of the beam is about 13 microns. In some embodiments, the diameter of the focused spot of the beam is about 14 microns. In some embodiments, the diameter of the focused spot of the beam is about 15 microns. In some embodiments, the diameter of the focused spot of the beam is about 16 microns. In some embodiments, the diameter of the focused spot of the beam is about 17 microns. In some embodiments, the diameter of the focused spot of the beam is about 18 microns. In some embodiments, the diameter of the focused spot of the beam is about 19 microns. In some embodiments, the diameter of the focused spot of the beam is about 20 microns.

Figure 1B:
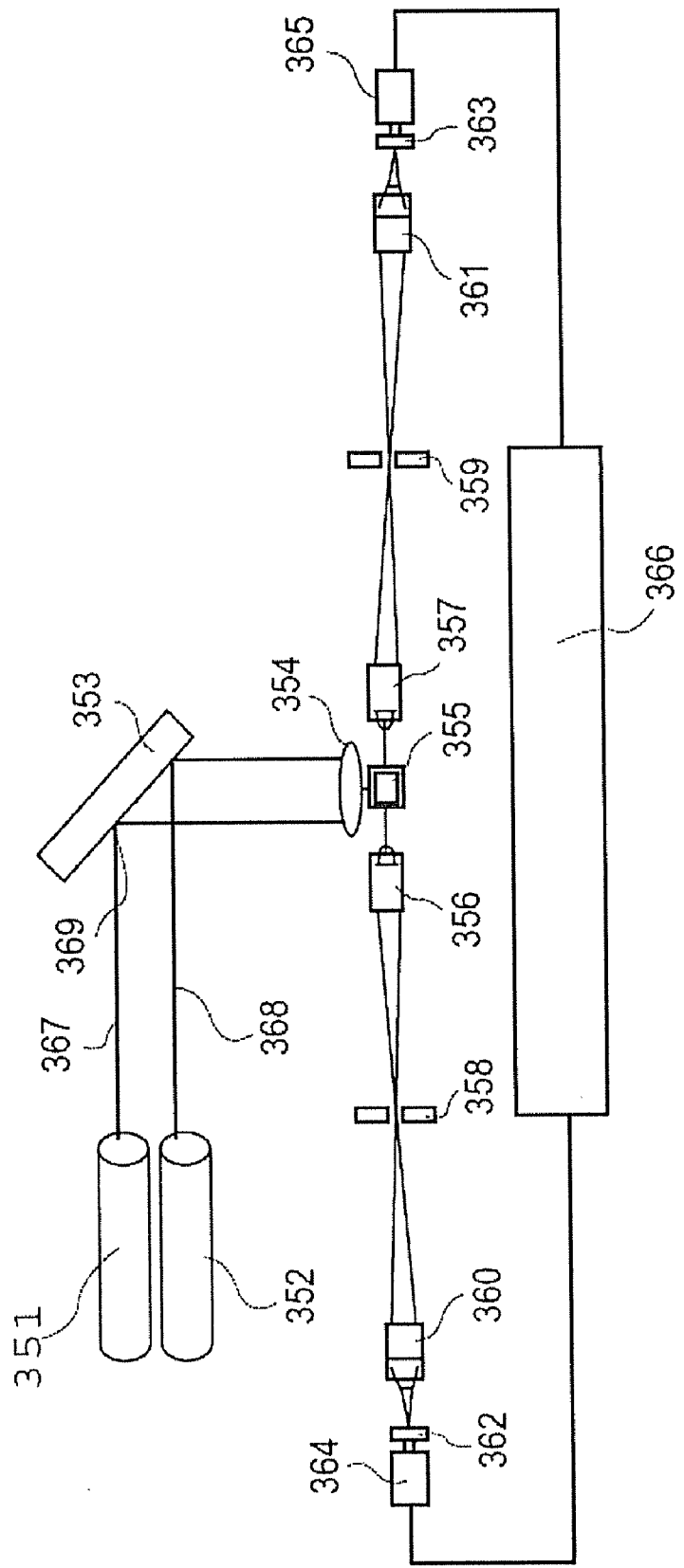

In an alternate embodiment of the single particle analyzer system, more than one electromagnetic radiation source can be used to excite particles labeled with fluorescent labels of different wavelengths. In another alternate embodiment, more than one interrogation space in the capillary flow cell can be used. In another alternate embodiment, multiple detectors can be employed to detect different emission wavelengths from the fluorescent labels. An illustration incorporating each of these alternative embodiments of an analyzer system is shown in FIG. 1B. These embodiments are incorporated by reference from previous U.S. patent application Ser. No. 11/048,660.

In some embodiments of the analyzer system 300, a motive force is required to move a particle through the capillary flow cell 313 of the analyzer system 300. In one embodiment, the motive force can be a form of pressure. The pressure used to move a particle through the capillary flow cell can be generated by a pump. In some embodiments, a Scivex, Inc. HPLC pump can be used. In some embodiments where a pump is used as a motive force, the sample can pass through the capillary flow cell at a rate of 1 µL/min to about 20 µL/min, or about 5 µL/min to about 20 µL/min. In some embodiments, the sample can pass through the capillary flow cell at a rate of about 5 µL/min. In some embodiments, the sample can pass through the capillary flow cell at a rate of about 10 µL/min. In some embodiments, the sample can pass through the capillary flow cell at a rate of about 15 µL/min. In some embodiments, the sample can pass through the capillary flow cell at a rate of about 20 µL/min. In some embodiments, an electrokinetic force can be used to move the particle through the analyzer system. Such a method has been previously disclosed and is incorporated by reference from previous U.S. patent application Ser. No. 11/048,660.

In one aspect of the analyzer system 300, the detector 309 of the analyzer system detects the photons emitted by the fluorescent label. In one embodiment, the photon detector is a photodiode. In a further embodiment, the detector is an avalanche photodiode detector. In some embodiments, the photodiodes can be silicon photodiodes with a wavelength detection of 190 nm and 1100 nm. When germanium photodiodes are used, the wavelength of light detected is between 400 nm to 1700 nm. In other embodiments, when an indium gallium arsenide photodiode is used, the wavelength of light detected by the photodiode is between 800 nm and 2600 nm. When lead sulfide photodiodes are used as detectors, the wavelength of light detected is between 1000 nm and 3500 nm.

In some embodiments, the optics of the electromagnetic radiation source 301 and the optics of the detector 309 are arranged in a conventional optical arrangement. In such an arrangement, the electromagnetic radiation source and the detector are aligned on different focal planes. The arrangement of the laser and the detector optics of the analyzer system as shown in FIGS. 1A and 1B is that of a conventional optical arrangement.

Figure 3A:
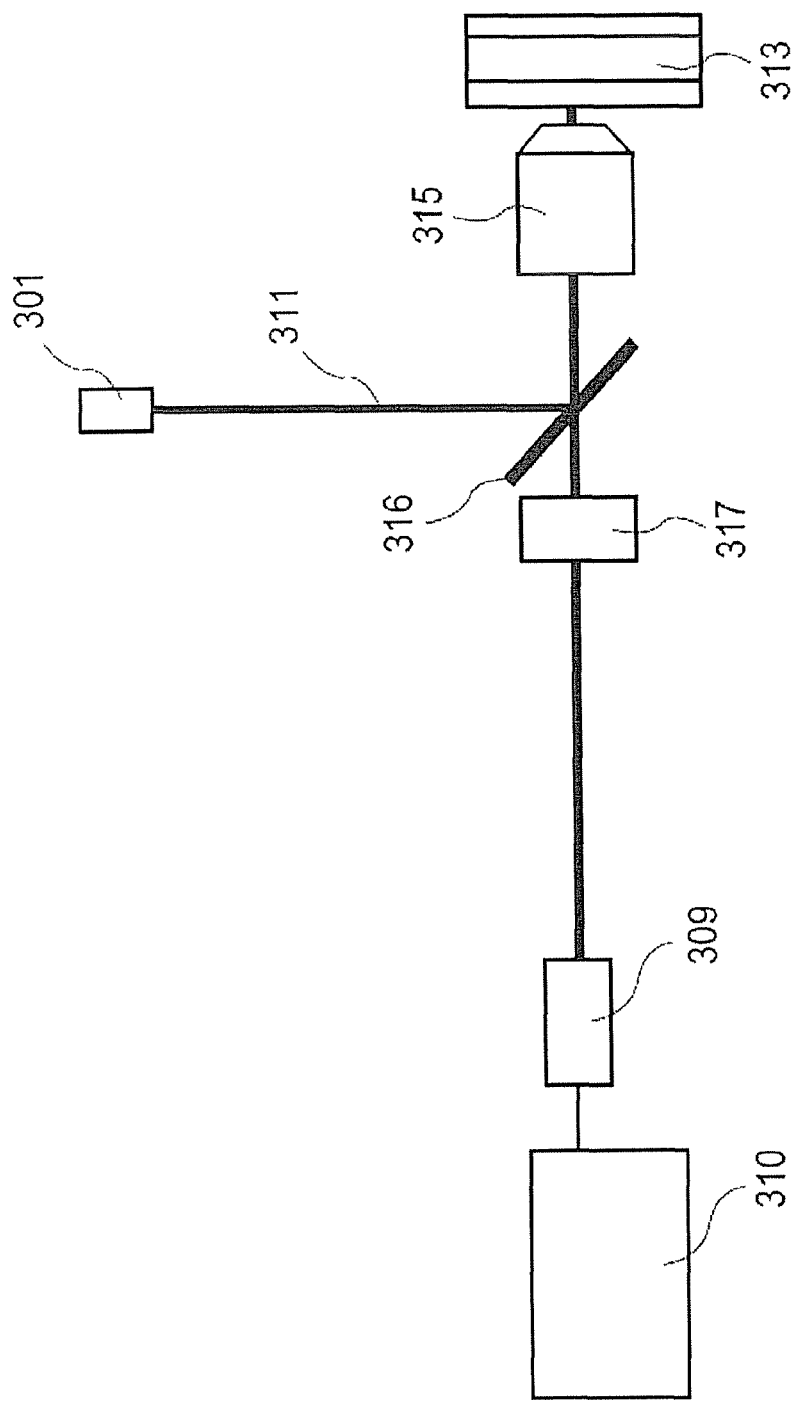
FIGS. 3A and 3B. Schematic diagrams showing the conventional (A) and confocal (B) positioning of laser and detector optics of a single particle analyzer.
Figure 3B:
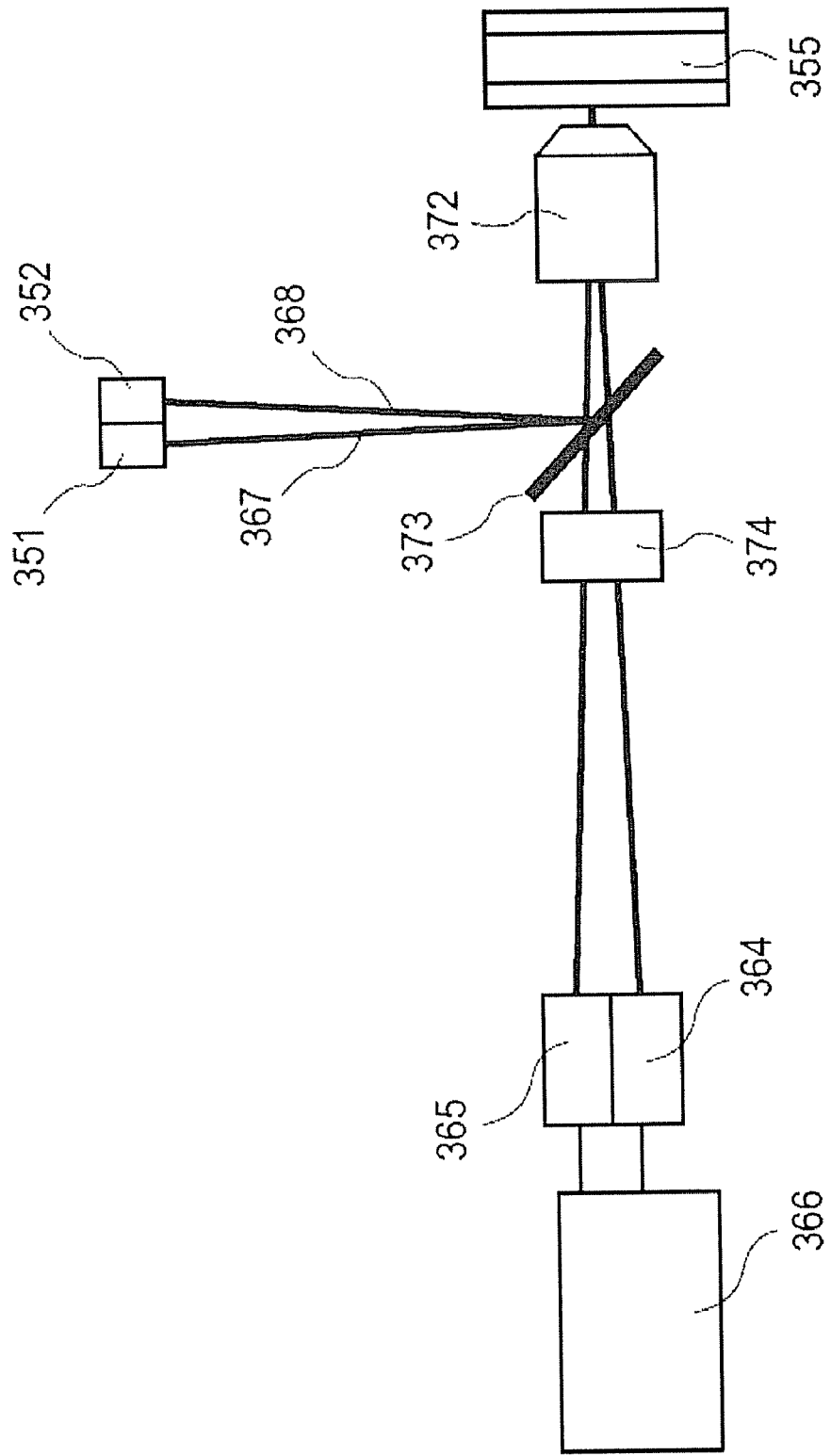
Figure 4:
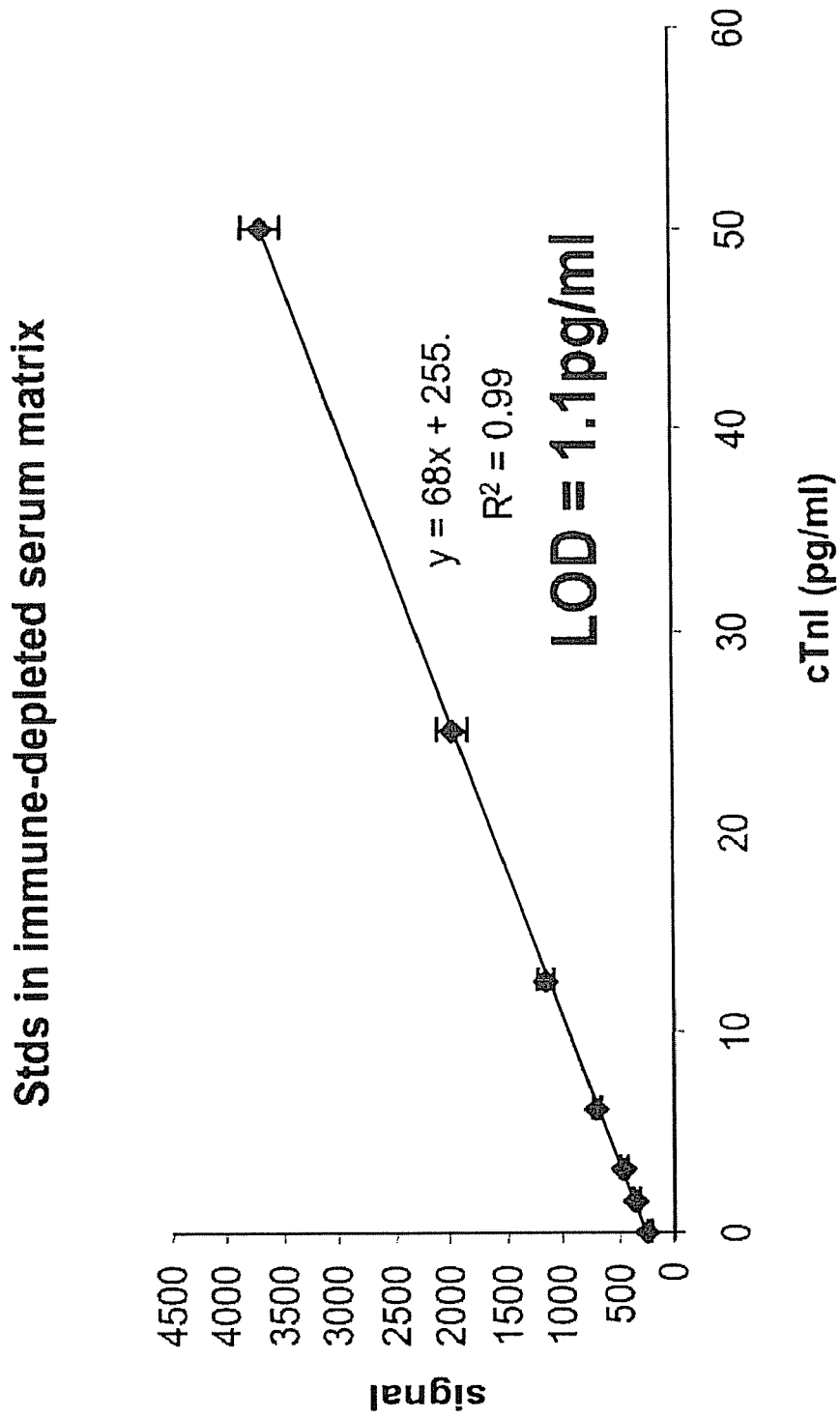
FIG. 4. Linearized standard curve for the range concentrations of cTnI.

In some embodiments, the optics of the electromagnetic radiation source and the optics of the detector are arranged in a confocal optical arrangement. In such an arrangement, the electromagnetic radiation source 301 and the detector 309 are aligned on the same focal plane. The confocal arrangement renders the analyzer more robust because the electromagnetic radiation source 301 and the detector optics 309 do not need to be realigned if the analyzer system is moved. This arrangement also makes the use of the analyzer more simplified because it eliminates the need to realign the components of the analyzer system. The confocal arrangement for the analyzer 300 (FIG. 1A) and the analyzer 355 (FIG. 1B) are shown in FIGS. 3A and 3B respectively. FIG. 3A shows that the beam 311 from an electromagnetic radiation source 301 is focused by the microscope objective 315 to form one interrogation space 314 (FIG. 2A) within the capillary flow cell 313. A dichroic mirror 316, which reflects laser light but passes fluorescent light, is used to separate the fluorescent light from the laser light. Filter 317 that is positioned in front of the detector eliminates any non-fluorescent light at the detector. In some embodiments, an analyzer system configured in a confocal arrangement can comprise two or more interrogations spaces. Such a method has been previously disclosed and is incorporated by reference from previous U.S. patent application Ser. No. 11/048,660.

The laser can be a tunable dye laser, such as a helium-neon laser. The laser can be set to emit a wavelength of 632.8 nm. Alternatively, the wavelength of the laser can be set to emit a wavelength of 543.5 nm or 1523 nm. Alternatively, the electromagnetic laser can be an argon ion laser. In such an embodiment, the argon ion laser can be operated as a continuous gas laser at about 25 different wavelengths in the visible spectrum, the wavelength set between 408.9 and 686.1 nm but at its optimum performance set between 488 and 514.5 nm.

1 Electromagnetic Radiation Source

In some embodiments of the analyzer system a chemiluminescent label may be used. In such an embodiment, it may not be necessary to utilize an EM source for detection of the particle. In another embodiment, the extrinsic label or intrinsic characteristic of the particle is a light-interacting label or characteristic, such as a fluorescent label or a light-scattering label. In such an embodiment, a source of EM radiation is used to illuminate the label and/or the particle. EM radiation sources for excitation of fluorescent labels are preferred.

In some embodiments, the analyzer system consists of an electromagnetic radiation source 301. Any number of radiation sources may be used in any one analyzer system 300 without departing from the scope of the invention. Multiple sources of electromagnetic radiation have been previously disclosed and are incorporated by reference from previous U.S. patent application Ser. No. 11/048,660. In some embodiments, all the continuous wave electromagnetic (EM) radiation sources emit electromagnetic radiation at the same wavelengths. In other embodiments, different sources emit different wavelengths of EM radiation.

In one embodiment, the EM source(s) 301, 351, 352 are continuous wave lasers producing wavelengths of between 200 nm and 1000 nm. Such EM sources have the advantage of being small, durable and relatively inexpensive. In addition, they generally have the capacity to generate larger fluorescent signals than other light sources. Specific examples of suitable continuous wave EM sources include, but are not limited to: lasers of the argon, krypton, helium-neon, helium-cadmium types, as well as, tunable diode lasers (red to infrared regions), each with the possibility of frequency doubling. The lasers provide continuous illumination with no accessory electronic or mechanical devices, such as shutters, to interrupt their illumination. In an embodiment where a continuous wave laser is used, an electromagnetic radiation source of 3 mW may be of sufficient energy to excite a fluorescent label. A beam from a continuous wave laser of such energy output may be between 2 to 5 µm in diameter. The time of exposure of the particle to laser beam in order to be exposed to 3 mW may be a time period of about 1 msec. In alternate embodiments, the time of exposure to the laser beam may be equal to or less than about 500 µsec. In an alternate embodiment, the time of exposure may be equal to or less than about 100 µsec. In an alternate embodiment, the time of exposure may be equal to or less than about 50 µsec. In an alternate embodiment, the time of exposure may be equal to or less than about 10 µsec.

LEDs are another low-cost, high reliability illumination source. Recent advances in ultra-bright LEDs and dyes with high absorption cross-section and quantum yield support the applicability of LEDs to single particle detection. Such lasers could be used alone or in combination with other light sources such as mercury arc lamps, elemental arc lamps, halogen lamps, arc discharges, plasma discharges, light-emitting diodes, or combination of these.

In other embodiments, the EM source could be in the form of a pulse wave laser. In such an embodiment, the pulse size of the laser is an important factor. In such an embodiment, the size, focus spot, and the total energy emitted by the laser is important and must be of sufficient energy as to be able to excite the fluorescent label. When a pulse laser is used, a pulse of longer duration may be required. In some embodiments a laser pulse of 2 nanoseconds may be used. In some embodiments a laser pulse of 5 nanoseconds may be used. In some embodiments a pulse of between 2 to 5 nanoseconds may be used.

The optimal laser intensity depends on the photo bleaching characteristics of the single dyes and the length of time required to traverse the interrogation space (including the speed of the particle, the distance between interrogation spaces if more than one is used and the size of the interrogation space(s)). To obtain a maximal signal, it is desirable to illuminate the sample at the highest intensity which will not result in photo bleaching a high percentage of the dyes. The preferred intensity is one such that no more that 5% of the dyes are bleached by the time the particle has traversed the interrogation space.

The power of the laser is set depending on the type of dye molecules that need to be stimulated and the length of time the dye molecules are stimulated, and/or the speed with which the dye molecules pass through the capillary flow cell. Laser power is defined as the rate at which energy is delivered by the beam and is measured in units of Joules/second, or Watts. It will be appreciated that the greater the power output of the laser, the shorter the time that the laser illuminates the particle may be, while providing a constant amount of energy to the interrogation space while the particle is passing through the space. Thus, in some embodiments, the combination of laser power and time of illumination is such that the total energy received by the interrogation space during the time of illumination is more than about 0.1, 0.5, 1, 2, 3, 4, 5, 6, 7, 8, 9, 10, 12, 15, 20, 25, 30, 35, 40, 45, 50, 60, 70, 80, 90, or 100 microJoule. In some embodiments, the combination of laser power and time of illumination is such that the total energy received by the interrogation space during the time of illumination is less than about 0.5, 1, 2, 3, 4, 5, 6, 7, 8, 9, 10, 12, 15, 20, 25, 30, 35, 40, 45, 50, 60, 70, 80, 90, 100, or 110 microJoule. In some embodiments, the combination of laser power and time of illumination is such that the total energy received by the interrogation space during the time of illumination is between about 0.1 and 100 microJoule. In some embodiments, the combination of laser power and time of illumination is such that the total energy received by the interrogation space during the time of illumination is between about 1 and 100 microJoule. In some embodiments, the combination of laser power and time of illumination is such that the total energy received by the interrogation space during the time of illumination is between about 1 and 50 microJoule. In some embodiments, the combination of laser power and time of illumination is such that the total energy received by the interrogation space during the time of illumination is between about 2 and 50 microJoule. In some embodiments, the combination of laser power and time of illumination is such that the total energy received by the interrogation space during the time of illumination is between about 3 and 60 microJoule. In some embodiments, the combination of laser power and time of illumination is such that the total energy received by the interrogation space during the time of illumination is between about 3 and 50 microJoule. In some embodiments, the combination of laser power and time of illumination is such that the total energy received by the interrogation space during the time of illumination is between about 3 and 40 microJoule. In some embodiments, the combination of laser power and time of illumination is such that the total energy received by the interrogation space during the time of illumination is between about 3 and 30 microJoule. In some embodiments, the combination of laser power and time of illumination is such that the total energy received by the interrogation space during the time of illumination is about 1 microJoule. In some embodiments, the combination of laser power and time of illumination is such that the total energy received by the interrogation space during the time of illumination is about 3 microJoule. In some embodiments, the combination of laser power and time of illumination is such that the total energy received by the interrogation space during the time of illumination is about 5 microJoule. In some embodiments, the combination of laser power and time of illumination is such that the total energy received by the interrogation space during the time of illumination is about 10 microJoule. In some embodiments, the combination of laser power and time of illumination is such that the total energy received by the interrogation space during the time of illumination is about 15 microJoule. In some embodiments, the combination of laser power and time of illumination is such that the total energy received by the interrogation space during the time of illumination is about 20 microJoule. In some embodiments, the combination of laser power and time of illumination is such that the total energy received by the interrogation space during the time of illumination is about 30 microJoule. In some embodiments, the combination of laser power and time of illumination is such that the total energy received by the interrogation space during the time of illumination is about 40 microJoule. In some embodiments, the combination of laser power and time of illumination is such that the total energy received by the interrogation space during the time of illumination is about 50 microJoule. In some embodiments, the combination of laser power and time of illumination is such that the total energy received by the interrogation space during the time of illumination is about 60 microJoule. In some embodiments, the combination of laser power and time of illumination is such that the total energy received by the interrogation space during the time of illumination is about 70 microJoule. In some embodiments, the combination of laser power and time of illumination is such that the total energy received by the interrogation space during the time of illumination is about 80 microJoule. In some embodiments, the combination of laser power and time of illumination is such that the total energy received by the interrogation space during the time of illumination is about 90 microJoule. In some embodiments, the combination of laser power and time of illumination is such that the total energy received by the interrogation space during the time of illumination is about 100 microJoule.

In some embodiments, the laser power output is set to at least about 1 mW, 2 mW, 3 mW, 4 mW, 5 mW, 6, mw, 7 mW, 8 mW, 9 mW, 10 mW, 13 mW, 15 mW, 20 mW, 25 mW, 30 mW, 40 mW, 50 mW, 60 mW, 70 mW, 80 mW, 90 mW, 100 mW, or more than 100 mW. In some embodiments, the laser power output is set to at least about 1 mW. In some embodiments, the laser power output is set to at least about 3 mW. In some embodiments, the laser power output is set to at least about 5 mW. In some embodiments, the laser power output is set to at least about 10 mW. In some embodiments, the laser power output is set to at least about 20 mW. In some embodiments, the laser power output is set to at least about 30 mW. In some embodiments, the laser power output is set to at least about 40 mW. In some embodiments, the laser power output is set to at least about 50 mW. In some embodiments, the laser power output is set to at least about 60 mW. In some embodiments, the laser power output is set to at least about 90 mW.

The time that the laser illuminates the interrogation space can be set to no less than about 1, 2, 3, 4, 5, 10, 15, 20, 30, 40, 50, 60, 70, 80, 90, 100, 150, 200, 150, 300, 350, 400, 450, 500, 600, 700, 800, 900, or 1000 microseconds. The time that the laser illuminates the interrogation space can be set to no more than about 2, 3, 4, 5, 10, 15, 20, 30, 40, 50, 60, 70, 80, 90, 100, 150, 200, 150, 300, 350, 400, 450, 500, 600, 700, 800, 900, 1000, 1500, or 2000 microseconds. The time that the laser illuminates the interrogation space can be set between about 1 and 1000 microseconds. The time that the laser illuminates the interrogation space can be set between about 5 and 500 microseconds. The time that the laser illuminates the interrogation space can be set between about 5 and 100 microseconds. The time that the laser illuminates the interrogation space can be set between about 10 and 100 microseconds. The time that the laser illuminates the interrogation space can be set between about 10 and 50 microseconds. The time that the laser illuminates the interrogation space can be set between about 10 and 20 microseconds. The time that the laser illuminates the interrogation space can be set between about 5 and 50 microseconds. The time that the laser illuminates the interrogation space can be set between about 1 and 100 microseconds. In some embodiments, the time that the laser illuminates the interrogation space is about 1 microsecond. In some embodiments, the time that the laser illuminates the interrogation space is about 5 microseconds. In some embodiments, the time that the laser illuminates the interrogation space is about 10 microseconds. In some embodiments, the time that the laser illuminates the interrogation space is about 25 microseconds. In some embodiments, the time that the laser illuminates the interrogation space is about 50 microseconds. In some embodiments, the time that the laser illuminates the interrogation space is about 100 microseconds. In some embodiments, the time that the laser illuminates the interrogation space is about 250 microseconds. In some embodiments, the time that the laser illuminates the interrogation space is about 500 microseconds. In some embodiments, the time that the laser illuminates the interrogation space is about 1000 microseconds.

For example, the time that the laser illuminates the interrogation space can be set to 1 millisecond, 250 microseconds, 100 microseconds, 50 microseconds, 25 microseconds or 10 microseconds with a laser that provides a power output of 3 mW, 4 mw, 5 mW, or more than 5 mW. In some embodiments, a label is illuminated with a laser that provides a power output of 3 mW and illuminates the label for about 1000 microseconds. In other embodiments, a label is illuminated for less than 1000 milliseconds with a laser providing a power output of not more than about 20 mW. In other embodiments, the label is illuminated with a laser power output of 20 mW for less than or equal to about 250 microseconds. In some embodiments, the label is illuminated with a laser power output of about 5 mW for less than or equal to about 1000 microseconds.

2. Capillary Flow Cell

The capillary flow cell is fluidly connected to the sample system. In one embodiment, the interrogation space 314 of an analyzer system, is determined by the cross sectional area of the corresponding beam 311 and by a segment of the beam within the field of view of the detector 309. In one embodiment of the analyzer system, the interrogation space 314 has a volume, as defined herein, of between about between about 0.01 and 500 pL, or between about 0.01 pL and 100 pL, or between about 0.01 pL and 10 pL, or between about 0.01 pL and 1 pL, or between about 0.01 pL and 0.5 pL, or between about 0.02 pL and about 300 pL, or between about 0.02 pL and about 50 pL or between about 0.02 pL and about 5 pL or between about 0.02 pL and about 0.5 pL or between about 0.02 pL and about 2 pL, or between about 0.05 pL and about 50 pL, or between about 0.05 pL and about 5 pL, or between about 0.05 pL and about 0.5 pL, or between about 0.05 pL and about 0.2 pL, or between about 0.1 pL and about 25 pL. In some embodiments, the interrogation space has a volume between about 0.01 pL and 10 pL. In some embodiments, the interrogation space 314 has a volume between about 0.01 pL and 1 pL. In some embodiments, the interrogation space 314 has a volume between about 0.02 pL and about 5 pL. In some embodiments, the interrogation space 314 has a volume between about 0.02 pL and about 0.5 pL. In some embodiments, the interrogation space 314 has a volume between about 0.05 pL and about 0.2 pL. In some embodiments, the interrogation space 314 has a volume of about 0.1 pL. Other useful interrogation space volumes are as described herein. It should be understood by one skilled in the art that the interrogation space 314 can be selected for maximum performance of the analyzer. Although very small interrogation spaces have been shown to minimize the background noise, large interrogation spaces have the advantage that low concentration samples can be analyzed in a reasonable amount of time. In embodiments in which two interrogation spaces 370 and 371 are used, volumes such as those described herein for a single interrogation space 314 may be used.

In one embodiment of the present invention, the interrogation spaces are large enough to allow for detection of particles at concentrations ranging from about 1000 femtomolar (fM) to about 1 zeptomolar (zM). In one embodiment of the present invention, the interrogation spaces are large enough to allow for detection of particles at concentrations ranging from about 1000 fM to about 1 attomolar (aM). In one embodiment of the present invention, the interrogation spaces are large enough to allow for detection of particles at concentrations ranging from about 10 fM to about 1 attomolar (aM). In many cases, the large interrogation spaces allow for the detection of particles at concentrations of less than about 1 fM without additional pre-concentration devices or techniques. One skilled in the art will recognize that the most appropriate interrogation space size depends on the brightness of the particles to be detected, the level of background signal, and the concentration of the sample to be analyzed.

The size of the interrogation space 314 can be limited by adjusting the optics of the analyzer. In one embodiment, the diameter of the beam 311 can be adjusted to vary the volume of the interrogation space 314. In another embodiment, the field of view of the detector 309 can be varied. Thus, the source 301 and the detector 309 can be adjusted so that single particles will be illuminated and detected within the interrogation space 314. In another embodiment, the width of aperture 306 (FIG. 1A) that determine the field of view of the detector 309 is variable. This configuration allows for altering the interrogation space, in near real time, to compensate for more or less concentrated samples, ensuring a low probability of two or more particles simultaneously being within an interrogation space. Similar alterations for two or more interrogation spaces, 370 and 371, may performed.

In another embodiment, the interrogation space can be defined through the use of a calibration sample of known concentration that is passed through the capillary flow cell prior to the actual sample being tested. When only one single particle is detected at a time in the calibration sample as the sample is passing through the capillary flow cell, the depth of focus together with the diameter of the beam of the electromagnetic radiation source determines the size of the interrogation space in the capillary flow cell.

Figure 2B:
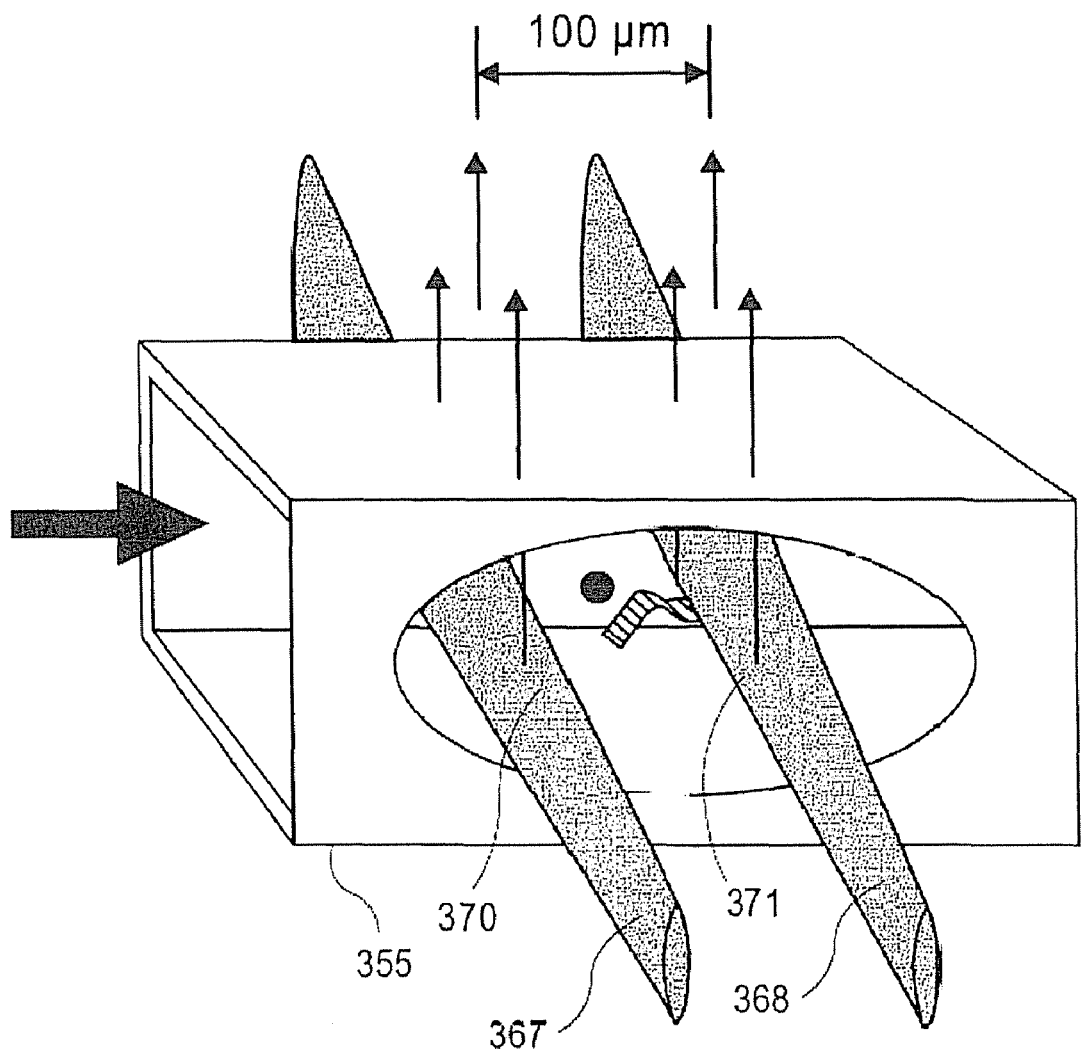

Physical constraints to the interrogation spaces can also be provided by a solid wall. In one embodiment, the wall is one or more of the walls of a flow cell 313 (FIG. 2A), when the sample fluid is contained within a capillary. In one embodiment, the cell is made of glass, but other substances transparent to light in the range of about 200 to about 1,000 nm or higher, such as quartz, fused silica, and organic materials such as Teflon, nylon, plastics, such as polyvinylchloride, polystyrene, and polyethylene, or any combination thereof, may be used without departing from the scope of the present invention. Although other cross-sectional shapes (e.g., rectangular, cylindrical) may be used without departing from the scope of the present invention, in one embodiment the capillary flow cell 313 has a square cross section. In another embodiment, the interrogation space may be defined at least in part by a channel (not shown) etched into a chip (not shown). Similar considerations apply to embodiments in which two interrogation spaces are used (370 and 371 in FIG. 2B).

The interrogation space is bathed in a fluid. In one embodiment, the fluid is aqueous. In other embodiments, the fluid is non-aqueous or a combination of aqueous and non-aqueous fluids. In addition the fluid may contain agents to adjust pH, ionic composition, or sieving agents, such as soluble macroparticles or polymers or gels. It is contemplated that valves or other devices may be present between the interrogation spaces to temporarily disrupt the fluid connection. Interrogation spaces temporarily disrupted are considered to be connected by fluid.

In another embodiment of the invention, an interrogation space is the single interrogation space present within the flow cell 313 which is constrained by the size of a laminar flow of the sample material within a diluent volume, also called sheath flow. In these and other embodiments, the interrogation space can be defined by sheath flow alone or in combination with the dimensions of the illumination source or the field of view of the detector. Sheath flow can be configured in numerous ways, including: The sample material is the interior material in a concentric laminar flow, with the diluent volume in the exterior; the diluent volume is on one side of the sample volume; the diluent volume is on two sides of the sample material; the diluent volume is on multiple sides of the sample material, but not enclosing the sample material completely; the diluent volume completely surrounds the sample material; the diluent volume completely surrounds the sample material concentrically; the sample material is the interior material in a discontinuous series of drops and the diluent volume completely surrounds each drop of sample material.

In some embodiments, single molecule detectors of the invention comprise no more than one interrogation space. In some embodiments, multiple interrogation spaces are used. Multiple interrogation spaces have been previously disclosed and are incorporated by reference from U.S. patent application Ser. No. 11/048,660. One skilled in the art will recognize that in some cases the analyzer will contain 2, 3, 4, 5, 6 or more distinct interrogation spaces.

3. Motive Force

In one embodiment of the analyzer system, the particles are moved through the interrogation space by a motive force. In some embodiments, the motive force for moving particles is pressure. In some embodiments, the pressure is supplied by a pump, and air pressure source, a vacuum source, a centrifuge, or a combination thereof. In some embodiments, the motive force for moving particles is an electrokinetic force. The use of an electrokinetic force as a motive force has been previously disclosed in a prior application and is incorporated by reference from U.S. patent application Ser. No. 11/048,660.

In one embodiment, pressure can be used as a motive force to move particles through the interrogation space of the capillary flow cell. In a further embodiment, pressure is supplied to move the sample by means of a pump. Suitable pumps are known in the art. In one embodiment, pumps manufactured for HPLC applications, such as those made by Scivax, Inc. can be used as a motive force. In other embodiments, pumps manufactured for microfluidics applications can be used when smaller volumes of sample are being pumped. Such pumps are described in U.S. Pat. Nos. 5,094,594, 5,730,187, 6,033,628, and 6,533,553, which discloses devices which can pump fluid volumes in the nanoliter or picoliter range. Preferably all materials within the pump that come into contact with sample are made of highly inert materials, e.g., polyetheretherketone (PEEK), fused silica, or sapphire.

A motive force is necessary to move the sample through the capillary flow cell to push the sample through the interrogation space for analysis. A motive force is also required to push a flushing sample through the capillary flow cell after the sample has been passed through. A motive force is also required to push the sample back out into a sample recovery vessel, when sample recovery is employed. Standard pumps come in a variety of sizes, and the proper size may be chosen to suit the anticipated sample size and flow requirements. In some embodiments, separate pumps are used for sample analysis and for flushing of the system. The analysis pump may have a capacity of approximately 0.000001 mL to approximately 10 mL, or approximately 0.001 mL to approximately 1 mL, or approximately 0.01 mL to approximately 0.2 mL, or approximately 0.005, 0.01, 0.05, 0.1, or 0.5 mL. Flush pumps may be of larger capacity than analysis pumps. Flush pumps may have a volume of about 0.01 mL to about 20 mL, or about 0.1 mL to about 10 mL, or about 0.1 mL to about 2 mL, or about or about 0.05, 0.1, 0.5, 1, 5, or 10 mL. These pump sizes are illustrative only, and those of skill in the art will appreciate that the pump size may be chosen according to the application, sample size, viscosity of fluid to be pumped, tubing dimensions, rate of flow, temperature, and other factors well known in the art. In some embodiments, pumps of the system are driven by stepper motors, which are easy to control very accurately with a microprocessor.

In preferred embodiments, the flush and analysis pumps are used in series, with special check valves to control the direction of flow. The plumbing is designed so that when the analysis pump draws up the maximum sample, the sample does not reach the pump itself. This is accomplished by choosing the ID and length of the tubing between the analysis pump and the analysis capillary such that the tubing volume is greater than the stroke volume of the analysis pump.

4. Detectors

In one embodiment, light (e.g., light in the ultra-violet, visible or infrared range) emitted by a fluorescent label after exposure to electromagnetic radiation is detected. The detector 309 (FIG. 1A), or detectors (364, 365, FIG. 1B), is capable of capturing the amplitude and duration of photon bursts from a fluorescent label-moiety complex, and further converting the amplitude and duration of the photon burst to electrical signals. Detection devices such as CCD cameras, video input module cameras, and Streak cameras can be used to produce images with contiguous signals. In another embodiment, devices such as a bolometer, a photodiode, a photodiode array, avalanche photodiodes, and photomultipliers which produce sequential signals may be used. Any combination of the aforementioned detectors may also be used. In one embodiment, avalanche photodiodes are used for detecting photons.

Using specific optics between an interrogation space 314 (FIG. 2A) and its corresponding detector 309 (FIG. 1A), several distinct characteristics of the emitted electromagnetic radiation can be detected including: emission wavelength, emission intensity, burst size, burst duration, and fluorescence polarization. In some embodiments, the detector 309 is a photodiode that is used in reverse bias. A photodiode set in reverse bias usually has an extremely high resistance. This resistance is reduced when light of an appropriate frequency shines on the P/N junction. Hence, a reverse biased diode can be used as a detector by monitoring the current running through it. Circuits based on this effect are more sensitive to light than ones based on zero bias.

In one embodiment of the analyzer system, the photodiode can be an avalanche photodiode, which can be operated with much higher reverse bias than conventional photodiodes, thus allowing each photo-generated carrier to be multiplied by avalanche breakdown, resulting in internal gain within the photodiode, which increases the effective responsiveness (sensitivity) of the device. The choice of photodiode is determined by the energy or emission wavelength emitted by the fluorescently labeled particle. In some embodiments, the photodiode is a silicon photodiode that detects energy in the range of 190-1100 nm; in another embodiment the photodiode is a germanium photodiode that detects energy in the range of 800-1700 nm; in another embodiment the photodiode is an indium gallium arsenide photodiode that detects energy in the range of 800-2600 nm; and in yet other embodiments, the photodiode is a lead sulfide photodiode that detects energy in the range of between less than 1000 nm to 3500 nm. In some embodiments, the avalanche photodiode is a single-photon detector designed to detect energy in the 400 nm to 1100 nm wavelength range. Single photon detectors are commercially available (for example Perkin Elmer, Wellesley, Mass.).

In some embodiments the detector is a avalanche photodiode detector that detects energy between 300 nm and 1700 nm. In one embodiment, silicon avalanche photodiodes can be used to detect wavelengths between 300 nm and 1100 nm. Indium gallium arsenic photodiodes can be used to detect wavelengths between 900 nm and 1700 nm. In some embodiments, an analyzer system can comprise at least one detector; in other embodiments, the analyzer system can comprise at least two detectors, and each detector can be chosen and configured to detect light energy at a specific wavelength range. For example, two separate detectors can be used to detect particles that have been tagged with different labels, which upon excitation with an EM source, will emit photons with energy in different spectra. In one embodiment, an analyzer system can comprise a first detector that can detect fluorescent energy in the range of 450-700 nm such as that emitted by a green dye (e.g. Alexa 546); and a second detector that can detect fluorescent energy in the range of 620-780 nm such as that emitted by a far-red dye (e.g. Alexa 647). Detectors for detecting fluorescent energy in the range of 400-600 nm such as that emitted by blue dyes (e.g. Hoechst 33342), and for detecting energy in the range of 560-700 nm such as that emitted by red dyes (Alexa 546 and Cy3) can also be used.

A system comprising two or more detectors can be used to detect individual particles that are each tagged with two or more labels that emit light in different spectra. For example, two different detectors can detect an antibody that has been tagged with two different dye labels. Alternatively, an analyzer system comprising two detectors can be used to detect particles of different types, each type being tagged with a different dye molecules, or with a mixture of two or more dye molecules. For example, two different detectors can be used to detect two different types of antibodies that recognize two different proteins, each type being tagged with a different dye label or with a mixture of two or more dye label molecules. By varying the proportion of the two or more dye label molecules, two or more different particle types can be individually detected using two detectors. It is understood that three or more detectors can be used without departing from the scope of the invention.

It should be understood by one skilled in the art that one or more detectors can be configured at each interrogation space, whether one or more interrogation spaces are defined within a flow cell, and that each detector may be configured to detect any of the characteristics of the emitted electromagnetic radiation listed above. The use of multiple detectors, e.g., for multiple interrogation spaces, has been previously disclosed in a prior application and is incorporated by reference here from U.S. patent application Ser. No. 11/048,660. Once a particle is labeled to render it detectable (or if the particle possesses an intrinsic characteristic rendering it detectable), any suitable detection mechanism known in the art may be used without departing from the scope of the present invention, for example a CCD camera, a video input module camera, a Streak camera, a bolometer, a photodiode, a photodiode array, avalanche photodiodes, and photomultipliers producing sequential signals, and combinations thereof. Different characteristics of the electromagnetic radiation may be detected including: emission wavelength, emission intensity, burst size, burst duration, fluorescence polarization, and any combination thereof.

C. Sampling System

In a further embodiment, the analyzer system may include a sampling system to prepare the sample for introduction into the analyzer system. The sampling system included is capable of automatically sampling a plurality of samples and providing a fluid communication between a sample container and a first interrogation space.

In some embodiments, the analyzer system of the invention includes a sampling system for introducing an aliquot of a sample into the single particle analyzer for analysis. Any mechanism that can introduce a sample may be used. Samples can be drawn up using either a vacuum suction created by a pump or by pressure applied to the sample that would push liquid into the tube, or by any other mechanism that serves to introduce the sample into the sampling tube. Generally, but not necessarily, the sampling system introduces a sample of known sample volume into the single particle analyzer; in some embodiments where the presence or absence of a particle or particles is detected, precise knowledge of the sample size is not critical. In preferred embodiments the sampling system provides automated sampling for a single sample or a plurality of samples. In embodiments where a sample of known volume is introduced into the system, the sampling system provides a sample for analysis of more than about 0.0001, 0.001, 0.01, 0.1, 1, 2, 5, 10, 20, 30, 40, 50, 60, 70, 80, 90, 100, 150, 200, 500, 1000, 1500, or 2000 μl. In some embodiments the sampling system provides a sample for analysis of less than about 2000, 1000, 500, 200, 100, 90, 80, 70, 60, 50, 40, 30, 20, 10, 5, 2, 1, 0.1, 0.01, or 0.001 μl. In some embodiments the sampling system provides a sample for analysis of between about 0.01 and 1500 μl, or about 0.1 and 1000 μl, or about 1 and 500 μl, or about 1 and 100 μl, or about 1 and 501, or about 1 and 20 μl. In some embodiments, the sampling system provides a sample for analysis between about 5 μl and 200 μl, or about 5 μl and 100 μl, or about 5 μl and 50 μl. In some embodiments, the sampling system provides a sample for analysis between about 10 μl and 200 μl, or between about 10 μl and 100 ul, or between about 10 μl and 50 μl. In some embodiments, the sampling system provides a sample for analysis between about 0.5 μl and about 50 μl.

In some embodiments, the sampling system provides a sample size that can be varied from sample to sample. In these embodiments, the sample size may be any one of the sample sizes described herein, and may be changed with every sample, or with sets of samples, as desired.

Sample volume accuracy, and sample to sample volume precision of the sampling system, is required for the analysis at hand. In some embodiments, the precision of the sampling volume is determined by the pumps used, typically represented by a CV of less than about 50, 40, 30, 20, 10, 5, 4, 3, 2, 1, 0.5, 0.1, 0.05, or 0.01% of sample volume. In some embodiments, the sample to sample precision of the sampling system is represented by a CV of less than about 50, 40, 30, 20, 10, 5, 4, 3, 2, 1, 0.5, 0.1, 0.05, or 0.01%. In some embodiments, the intra-assay precision of the sampling system is represented by a CV of less than about 10, 5, 1, 0.5, or 0.1%. In some embodiments, the intra-assay precision of the sampling system shows a CV of less than about 5%. In some embodiments, the interassay precision of the sampling system is represented by a CV of less than about 10, 5, or 1%. In some embodiments, the interassay precision of the sampling system shows a CV of less than about 5%.

In some embodiments, the sampling system provides low sample carryover, advantageous in that an additional wash step is not required between samples. Thus, in some embodiments, sample carryover is less than about 1, 0.5, 0.1, 0.05, 0.04, 0.03, 0.02, 0.01, 0.005, or 0.001%. In some embodiments, sample carryover is less than about 0.02%. In some embodiments, sample carryover is less than about 0.01%.

In some embodiments the sampler provides a sample loop. In these embodiments, multiple samples are drawn into tubing sequentially and each is separated from the others by a "plug" of buffer. The samples typically are read one after the other with no flushing in between. Flushing is done once at the end of the loop. In embodiments where a buffer "plug" is used, the plug may be recovered ejecting the buffer plug into a separate well of a microtiter plate.

The sampling system may be adapted for use with standard assay equipment, for example, a 96-well microtiter plate, or, preferably, a 384-well plate. In some embodiments the system includes a 96 well plate positioner and a mechanism to dip the sample tube into and out of the wells, e.g., a mechanism providing movement along the X, Y, and Z axes. In some embodiments, the sampling system provides multiple sampling tubes from which samples may be stored and extracted from, when testing is commenced. In some embodiments, all samples from the multiple tubes are analyzed on one detector. In other embodiments, multiple single molecule detectors may be connected to the sample tubes. Samples may be prepared by steps that include operations performed on sample in the wells of the plate prior to sampling by the sampling system, or sample may be prepared within the analyzer system, or some combination of both.

D. Sample Preparation System

Sample preparation includes the steps necessary to prepare a raw sample for analysis. These steps can involve, by way of example, one or more steps of: separation steps such as centrifugation, filtration, distillation, chromatography; concentration, cell lysis, alteration of pH, addition of buffer, addition of diluents, addition of reagents, heating or cooling, addition of label, binding of label, cross-linking with illumination, separation of unbound label, inactivation and/or removal of interfering compounds and any other steps necessary for the sample to be prepared for analysis by the single particle analyzer. In some embodiments, blood is treated to separate out plasma or serum. Additional labeling, removal of unbound label, and/or dilution steps may also be performed on the serum or plasma sample.

In some embodiments, the analyzer system includes a sample preparation system that performs some or all of the processes needed to provide a sample ready for analysis by the single particle analyzer. This system may perform any or all of the steps listed above for sample preparation. In some embodiments samples are partially processed by the sample preparation system of the analyzer system. Thus, in some embodiments, a sample may be partially processed outside the analyzer system first. For example, the sample may be centrifuged first. The sample may then be partially processed inside the analyzer by a sample preparation system. Processing inside the analyzer includes labeling the sample, mixing the sample with a buffer and other processing steps that will be known to one in the art. In some embodiments, a blood sample is processed outside the analyzer system to provide a serum or plasma sample, which is introduced into the analyzer system and further processed by a sample preparation system to label the particle or particles of interest and, optionally, to remove unbound label. In other embodiments preparation of the sample can include immunodepletion of the sample to remove particles that are not of interest or to remove particles that can interfere with sample analysis. In yet other embodiments, the sample can be depleted of particles that can interfere with the analysis of the sample. For example, sample preparation can include the depletion of heterophilic antibodies, which are known to interfere with immunoassays that use non-human antibodies to directly or indirectly detect a particle of interest. Similarly, other proteins that interfere with measurements of the particles of interest can be removed from the sample using antibodies that recognize the interfering proteins.

In some embodiments, the sample can be subjected to solid phase extraction prior to being assayed and analyzed. For example, a serum sample that is assayed for cAMP can first be subjected to solid phase extraction using a c18 column to which it binds. Other proteins such as proteases, lipases and phosphatases are washed from the column, and the cAMP is eluted essentially free of proteins that can degrade or interfere with measurements of cAMP. Solid phase extraction can be used to remove the basic matrix of a sample, which can diminish the sensitivity of the assay. In yet other embodiments, the particles of interest present in a sample may be concentrated by drying or lyophilizing a sample and solubilizing the particles in a smaller volume than that of the original sample. For example, a sample of exhaled breath condensate (EBC) can be dried and resuspended in a small volume of a suitable buffer solution to enhance the detection of the particle of interest.

In some embodiments the analyzer system provides a sample preparation system that provides complete preparation of the sample to be analyzed on the system, such as complete preparation of a blood sample, a saliva sample, a urine sample, a cerebrospinal fluid sample, a lymph sample, a BAL sample, an exhaled breath condensate sample (EBC), a biopsy sample, a forensic sample, a bioterrorism sample, and the like. In some embodiments the analyzer system provides a sample preparation system that provides some or all of the sample preparation. In some embodiments, the initial sample is a blood sample that is further processed by the analyzer system. In some embodiments, the sample is a serum or plasma sample that is further processed by the analyzer system. The serum or plasma sample may be further processed by, e.g., contacting with a label that binds to a particle or particles of interest; the sample may then be used with or without removal of unbound label.

In some embodiments, sample preparation is performed, either outside the analysis system or in the sample preparation component of the analysis system, on one or more microtiter plates, such as a 96-well plate. Reservoirs of reagents, buffers, and the like can be in intermittent fluid communication with the wells of the plate by means of tubing or other appropriate structures, as are well-known in the art. Samples may be prepared separately in 96 well plates or tubes. Sample isolation, label binding and, if necessary, label separation steps may be done on one plate. In some embodiments, prepared particles are then released from the plate and samples are moved into tubes for sampling into the sample analysis system. In some embodiments, all steps of the preparation of the sample are done on one plate and the analysis system acquires sample directly from the plate. Although this embodiment is described in terms of a 96-well plate, it will be appreciated that any vessel for containing one or more samples and suitable for preparation of sample may be used. For example, standard microtiter plates of 384 or 1536 wells may be used. More generally, in some embodiments, the sample preparation system is capable of holding and preparing more than about 5, 10, 20, 30, 40, 50, 60, 70, 80, 90, 100, 200, 300, 500, 1000, 5000, or 10,000 samples. In some embodiments, multiple samples may be sampled for analysis in multiple analyzer systems. Thus, in some embodiments, 2 samples, or more than about 2, 3, 4, 5, 7, 10, 15 20, 50, or 100 samples are sampled from the sample preparation system and run in parallel on multiple sample analyzer systems.

Microfluidics systems may also be used for sample preparation and as sample preparation systems that are part of analyzer systems, especially for samples suspected of containing concentrations of particles high enough that detection requires smaller samples. Principles and techniques of microfluidic manipulation are known in the art. See, e.g., U.S. Pat. Nos. 4,979,824; 5,770,029; 5,755,942; 5,746,901; 5,681,751; 5,658,413; 5,653,939; 5,653,859; 5,645,702; 5,605,662; 5,571,410; 5,543,838; 5,480,614; 5,716,825; 5,603,351; 5,858,195; 5,863,801; 5,955,028; 5,989,402; 6,041,515; 6,071,478; 6,355,420; 6,495,104; 6,386,219; 6,606,609; 6,802,342; 6,749,734; 6,623,613; 6,554,744; 6,361,671; 6,143,152; 6,132,580; 5,274,240; 6,689,323; 6,783,992; 6,537,437; 6,599,436; 6,811,668 and published PCT patent application no. WO9955461(A1). Samples may be prepared in series or in parallel, for use in a single or multiple analyzer systems.

Preferably, the sample comprises a buffer. The buffer may be mixed with the sample outside the analyzer system, or it may be provided by the sample preparation mechanism. While any suitable buffer can be used, the preferable buffer has low fluorescence background, is inert to the detectably labeled particle, can maintain the working pH and, in embodiments wherein the motive force is electrokinetic, has suitable ionic strength for electrophoresis. The buffer concentration can be any suitable concentration, such as in the range from about 1 to about 200 mM. Any buffer system may be used as long as it provides for solubility, function, and delectability of the molecules of interest. Preferably, for application using pumping, the buffer is selected from the group consisting of phosphate, glycine, acetate, citrate, acidulate, carbonate/bicarbonate, imidazole, triethanolamine, glycine amide, borate, MES, Bis-Tris, ADA, aces, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, and CABS. The buffer can also be selected from the group consisting of Gly-Gly, bicine, tricine, 2-morpholine ethanesulfonic acid (MES), 4-morpholine propanesulfonic acid (MOPS) and 2-amino-2-methyl-1-propanol hydrochloride (AMP). A useful buffer is 2 mM Tris/borate at pH 8.1, but Tris/glycine and Tris/HCl are also acceptable. Other buffers are as described herein.

Buffers useful for electrophoresis are disclosed in a prior application and are incorporated by reference herein from U.S. patent application Ser. No. 11/048,660.

E. Sample Recovery

One highly useful feature of embodiments of the analyzers and analysis systems of the invention is that the sample can be analyzed without consuming it. This can be especially important when sample materials are limited. Recovering the sample also allows one to do other analyses or reanalyze it. The advantages of this feature for applications where sample size is limited and/or where the ability to reanalyze the sample is desirable, e.g., forensic, drug screening, and clinical diagnostic applications, will be apparent to those of skill in the art.

Thus, in some embodiments, the analyzer system of the invention further provides a sample recovery system for sample recovery after analysis. In these embodiments, the system includes mechanisms and methods by which the sample is drawn into the analyzer, analyzed and then returned, e.g., by the same path, to the sample holder, e.g., the sample tube. Because no sample is destroyed and because it does not enter any of the valves or other tubing, it remains uncontaminated. In addition, because all the materials in the sample path are highly inert, e.g., PEEK, fused silica, or sapphire, there is little contamination from the sample path. The use of the stepper motor controlled pumps (particularly the analysis pump) allows precise control of the volumes drawn up and pushed back out. This allows complete or nearly complete recovery of the sample with little if any dilution by the flush buffer. Thus, in some embodiments, more than about 50%, 60%, 70%, 80%, 85%, 90%, 95%, 96%, 97%, 98%, 99%, 99.5%, or 99.9% of the sample is recovered after analysis. In some embodiments, the recovered sample is undiluted. In some embodiments, the recovered sample is diluted less than about 1.5-fold, 1.4-fold, 1.3-fold, 1.2-fold, 1.1-fold, 1.05-fold, 1.01-fold, 1.005-fold, or 1.001-fold.

For sampling and/or sample recovery, any mechanism for transporting a liquid sample from a sample vessel to the analyzer may be used. In some embodiments the inlet end of the analysis capillary has attached a short length of tubing, e.g., PEEK tubing that can be dipped into a sample container, e.g. a test tube or sample well, or can be held above a waste container. When flushing, to clean the previous sample from the apparatus, this tube is positioned above the waste container to catch the flush waste. When drawing a sample in, the tube is put into the sample well or test tube. Typically the sample is drawn in quickly, and then pushed out slowly while observing particles within the sample. Alternatively, in some embodiments, the sample is drawn in slowly during at least part of the draw-in cycle; the sample may be analyzed while being slowly drawn in. This can be followed by a quick return of the sample and a quick flush. In some embodiments, the sample may be analyzed both on the inward (draw-in) and outward (pull out) cycle, which improves counting statistics, e.g., of small and dilute samples, as well as confirming results, and the like. If it is desired to save the sample, it can be pushed back out into the same sample well it came from, or to another. If saving the sample is not desired, the tubing is positioned over the waste container.

VI. Methods Using Highly Sensitive Analysis of Cardiac Troponin

The methods of the present invention make possible measurement of cardiac troponin levels at concentrations far lower than previously measured. Although cardiac troponin is an accepted marker for cardiac muscle damage, its usefulness has been limited by the fact that, with current methods of analysis, it is only detectable after considerable damage to cardiac muscle has occurred, because of the lack of sensitivity of current methods. The Joint European Society of Cardiology/American College of Cardiology committee for the Redefinition of Myocardial Infarction has recommended that an increased concentration of cardiac troponin be defined as a measurement exceeding the $99^{th}$ percentile of the distribution of cardiac troponin concentrations in the reference group, a very low threshold. A total imprecision (CV) at this decision limit of <10% is recommended. However, the analytical imprecision obtained with presently available immunoassays for cardiac troponins is not uniform, mainly at the low concentration range. In addition, the assays that are currently available lack sufficient sensitivity for detecting troponin levels in nonclinical (normal) subjects, and a true baseline or a level of troponin defined in a normal population, has not been defined. The analyzer systems of the invention have been shown to be able to consistently detect levels of cTnI at concentrations of less than 10 pg/ml with a total imprecision of less than 10% (See Examples). Thus, the invention provides methods for diagnosis, prognosis, or methods of treatment based on the highly sensitive detection of cardiac troponin in individuals.

In some embodiments, the invention provides a method for determining a diagnosis, prognosis, or method of treatment in an individual by i) determining a concentration of cardiac troponin in a sample or determining the concentrations of cardiac troponin in a series of samples from the individual, where the concentration is determined by a cardiac troponin assay with a limit of detection for the cardiac troponin in said sample of less than about 50, 40, 30, 10, 5, 4, 3, 2 or 1 pg/ml, e.g., less than about 20 pg/ml; and ii) determining a diagnosis, prognosis, or method of treatment in said individual, based on the concentration in the sample, or on the concentrations in the series of samples. The method of determining the concentration of cardiac troponin includes any suitable method with the requisite sensitivity, e.g., the methods descried herein. In some embodiments, the methods utilize a method of determining a concentration of cardiac troponin in the sample where the method comprises detecting single molecules of troponin, or complexes or fragments thereof.

In some embodiments, the threshold concentration of troponin is determined by analyzing samples, e.g., blood, serum, or plasma samples, from an apparently healthy population for cardiac troponin, e.g., cardiac troponin I, and determining the level at which 80, 90, 95, 96, 97, 98, 99, 99.5, or 99.9% of the population fall below that level (concentration). This value is the threshold value. In some embodiments, the threshold value is set at the $99^{th}$ percentile. In some embodiments, the analyzing is performed using a method with a level of detection for the cardiac troponin of less than about 50, 20, 10, 5, or 1 pg/ml, e.g., less than about 5 pg/ml.

In some embodiments, the invention provides a method for determining a diagnosis, prognosis, or method of treatment in an individual by comparing a value for a concentration of cardiac troponin in a sample from the individual with a normal value or a range of normal values for cardiac troponin, where the normal vale or range of normal values is determined by a cardiac troponin assay with a limit of detection for the cardiac troponin in said sample of less than about 50, 40, 30, 10, 5, 4, 3, 2 or 1 pg/ml, e.g., less than about 20 pg/ml; and ii) determining a diagnosis, prognosis, or method of treatment in said individual, based on comparison.

In some embodiments, the cardiac troponin is cardiac troponin I or cardiac troponin T. In some embodiments, the cardiac troponin is cardiac troponin T. In some embodiments, the cardiac troponin is cardiac troponin I. The method may use total troponin, e.g., total cTnI, or cTnT, or total cTnI+cTnT, as described herein, in determining a diagnosis, prognosis, or method of treatment. In some embodiments, the method may use the concentration of free, complexed, or fragments of the cardiac troponin, or a comparison of these (e.g., a ratio), to determine a diagnosis, prognosis, or method of treatment.

A. Samples

The sample or series of samples may be any suitable sample; in some embodiments, the sample(s) will be blood, serum, or plasma. In some embodiments, the sample or series of samples are serum samples. The individual may be an animal, e.g., mammal, e.g., human.

A single sample may be taken, or a series of samples may be taken. If a series of samples is taken, they may be taken at any suitable interval, e.g., intervals of minutes, hours, days, weeks, months, or years. In an acute clinical setting, typically a series of samples will be taken over the course of hours and days, with the samples separated by a matter of hours. When an individual is followed for longer periods, sample intervals may be months or years. Diagnosis, prognosis, or method of treatment may be determined from a single sample, or from one or more of a series of samples, or from changes in the series of samples, e.g., an increase in concentration at a certain rate may indicate a severe condition whereas increase at a slower rate or no increase may indicate a relatively benign or less serious condition. The rate of change may be measured over the course of hours, days, weeks, months, or years. Rate of change in a given individual may, in some cases, be more relevant than an absolute value. In acute setting, an extremely rapid rate of change, e.g., a "spike", can indicate an imminent, ongoing, or recent cardiac event. In other settings, a rise in values over a period of days, weeks, months or years in an individual can indicate ongoing and worsening cardiac damage, e.g., cardiac damage due to a cardiac condition (e.g., cardiac hypertrophy or congestive heart failure) or cardiac damage due to a non-cardiac condition (e.g., toxicity from drug exposure).

In some embodiments, at least one sample is taken during or after a cardiac stress test. E.g., a sample may be taken before the stress test, and one or more samples taken during the test. Deviations in cardiac troponin levels between the sample before the test and the sample(s) taken during the test can provide diagnostic or prognostic information, e.g., indicate the likelihood of coronary artery disease or other pathology associated with the cardiac muscle. Other comparisons may be done as well, such as comparisons of any of the samples to normal or threshold levels, or determination of a rate of change in the concentration of cardiac troponin in the samples, all of which may yield useful information regarding cardiac and cardiovascular health, as well as other conditions as described herein.

In some embodiments, at least one sample is taken at or near the time the individual presents to a health professional with one or more symptoms indicative of a condition that may involve cardiac damage. Settings in which an individual may present to a health care professional include, but are not limited to ambulatory, urgent care, critical care, intensive care, monitoring unit, inpatient, outpatient, physician office, medical clinic, emergency response setting, including an ambulance, and health screening settings. In some embodiments, one or more samples are taken from the individual and are assayed for cardiac troponin locally, i.e., at or near the setting at which the samples are taken. For example, an individual who presents at a hospital may have one or more samples taken that are assayed for cardiac troponin within the hospital. For example, an individual who presents at a hospital may have one or more samples taken that are assayed for cardiac troponin within the hospital. In some embodiments, one or more samples are taken from the individual and are assayed for cardiac troponin in a CLIA laboratory. In some embodiments, the individual displays one or more symptoms consistent with acute coronary syndrome. In some embodiments, the individual displays one or more symptoms consistent with AMI. Such symptoms include, but are not limited to, chest pain, chest pressure, arm pain, abnormal EKG, abnormal enzyme levels, and shortness of breath.

B. Determination of Diagnosis, Prognosis, or Method of Treatment

In some embodiments, step ii) includes comparing said concentration or series of concentrations to a normal value for said concentration, comparing said concentration or series of concentrations to a predetermined threshold level, comparing said concentration or series of concentrations to a baseline value, or determining a rate of change of concentration for said series of concentrations.

In some embodiments, step ii) comprises comparing said concentration of troponin in said sample with a predetermined threshold concentration, and determining a diagnosis, prognosis, or method of treatment if the sample concentration is greater than the threshold level. The threshold concentration can be determined by, e.g., determining the 99th percentile concentration of troponin in a group of individuals, and setting said threshold concentration at said 99th percentile concentration. An example of this is given in Examples.

Normal values, threshold values, rates of change, ratios of values, and other useful diagnostic and prognostic indicators may be established by methods well-known in the art. For example, these values may be determined by comparing samples from a case population and a control population, where the case population exhibits the biological state for which diagnosis, prognosis, or method of treatment is desired, and the control population does not exhibit the biological state. In some embodiments, a longitudinal study may be done, e.g., the case population may be a subset of the control population that, over time, exhibits the biological state. It will be appreciated that data from a plurality of studies may be used to determine a consensus value or range of values for normal, and for prognostic or diagnostic levels.

In developing diagnostic or prognostic test, data for one or more potential markers may be obtained from a group of subjects. The group of subjects is divided into at least two sets, and preferably the first set and the second set each have an approximately equal number of subjects. The first set includes subjects who have been confirmed as having a disease or, more generally, being in a first condition state. For example, this first set of patients may be those that have recently had a disease incidence, or may be those having a specific type of disease, such as AMI. The confirmation of the condition state may be made through a more rigorous and/or expensive testing such as MRI or CT. Hereinafter, subjects in this first set will be referred to as "diseased". The second set of subjects is simply those who do not fall within the first set. Subjects in this second set may be "non-diseased;" that is, normal subjects. Alternatively, subjects in this second set may be selected to exhibit one symptom or a constellation of symptoms that mimic those symptoms exhibited by the "diseased" subjects. In still another alternative, this second set may represent those at a different time point from disease incidence. Preferably, data for the same set of markers is available for each patient. This set of markers may include all candidate markers which may be suspected as being relevant to the detection of a particular disease or condition. Actual known relevance is not required. Embodiments of the compositions, methods and systems described herein may be used to determine which of the candidate markers are most relevant to the diagnosis of the disease or condition. The levels of each marker in the two sets of subjects may be distributed across a broad range, e.g., as a Gaussian distribution. However, no distribution fit is required.

1. Acute Myocardial Infarct

The methods of the invention are especially useful in diagnosis, prognosis, and/or treatment selection in patients suspected of acute myocardial infarct (AMI). Single or serial cardiac troponin measurements in patients suspected of AMI provide incremental prognostic information that improves the prognosis and indicates appropriate and early therapeutic intervention to minimize the risk of adverse outcomes.

Thus, the invention provides a method of diagnosing, predicting, and/or preventing or treating AMI in an individual by assaying a sample from the individual, e.g., a blood sample, plasma sample, and/or serum sample, for cardiac troponin, e.g., cTnI, and detecting a concentration of cardiac troponin in the sample at a limit of detection of less than about 50, 40, 30, 20, 15, 10, 9, 8, 7, 6, 5, 4, 3, 2, or 1 pg/ml, e.g., less than about 20 pg/ml, wherein the concentration of cardiac troponin in the sample indicates or predicts AMI. The cardiac troponin may be cTnI or cTnT, and may be total troponin or a measure of a particular form, e.g., free, complexed, or fragment; in some embodiments, a ratio of one or more forms of the troponin is used, as described herein. In some embodiments, total cTnI is measured in the sample or series of samples. In some embodiments, total cTnT is measured in the sample or series of samples. In some embodiments, total cTnI+cTnT is measured in the sample or series of samples. In some embodiments, the cardiac troponin level is determined at or near the time the individual presents to a health professional with symptoms indicative of AMI. Such symptoms include, but are not limited to, chest pain, chest pressure, arm pain, abnormal EKG, abnormal enzyme levels, and shortness of breath.

In some embodiments, a series of measurements is taken, and a spike in the cardiac troponin concentration in the samples indicates, predicts, or provides a basis for prognosis of AMI. In some embodiments, a spike of over 50%, over 100%, over 150%, over 200%, over 250%, over 300%, over 400%, or over 500% of baseline indicates, predicts, or provides a basis for prognosis of AMI. In some embodiments, a cardiac troponin level of over about 1, 2, 3, 4, 5, 6, 7, 8, 9, 10, 15, 20, 25, 30, 35, 40, 45, or 50 pg/ml in a single sample indicates, predicts, or provides a basis for prognosis of AMI, regardless of baseline levels, if obtained. In some embodiments, a cardiac troponin level of about 1-10, or about 5-15, or about 10-50, about 10-200, about 10-100, or about 10-40, or about 15-50, or about 15-40, or about 20-200, about 20-150, about 20-100, about 20-50, or about 20-40, or about 20-30 pg/ml indicates, predicts, or provides a basis for prognosis of AMI.

In some embodiments diagnosis or prognosis includes stratification for the individual, based on cardiac troponin concentration in the sample or series of samples. Such stratification may be based on the concentration of cardiac troponin in single samples, presence of spikes and/or size of spikes from baseline in a series of samples, ratios of different forms of the cardiac troponin, absolute values for different forms of cardiac troponin, rate of change in concentration for the cardiac troponin or for one or more forms of the cardiac troponin in a series of samples, change in ratios of different forms of cardiac troponin over time in a series of samples, and any other information based at least in part on cardiac troponin concentration in the sample or series of samples. Stratification may be based on values obtained from populations of normal and diseased subjects, as described herein. Appropriate treatment may also be determined based on the stratification of the individual.

In some embodiments, concentration of cardiac troponin is determined in combination with one or more other markers, e.g., markers of myocardial ischemia, myocardial infarct or markers of stroke, and the concentrations of each marker are considered in determining the diagnosis, prognosis, or method of treatment. Other clinical indications typically will also be taken into account, e.g., EKG, symptoms, history, and the like, as will be apparent to those of skill in the art. Appropriate algorithms for diagnosis, prognosis, or treatment may be constructed based on the combinations of such markers and clinical indications in combination with troponin levels.

Markers useful in combination with cardiac troponin in the methods of the invention include but are not limited to creatine kinase (CK) and its myocardial fraction CK myocardial band (MB), aspartate aminotransferase, lactate dehydrogenase (LDH), α-hydroxybutyrate dehaydrogenase, myoglobin, glutamate oxaloacetate transaminase, glycogen phosphorylase BB, unbound free fatty acids, heart fatty acid binding protein (H-FABP), ischemia-modified albumin, myosin light chain 1, myosin light chain 2. Markers of inflammation and plaque instability useful in combination with cardiac troponin in the methods of the invention include but are not limited to C-reactive protein, white blood cell count, soluble CD40 ligand, myeloperoxidase, monocyte chemoattractant protein-1, whole blood choline, and pregnancy-associated plasma protein A. Other markers of inflammation may be detected, and include combinations of Il-8, IL-1β, IL6, IL10, TNF, and IL-12p70, as well as other cytokines or markers that will be apparent to those of skill in the art.

In some embodiments, cardiac troponin, e.g., cTnI, is measured together, e.g., in the same sample, or in samples from the same individual taken at or near the same time, with a marker selected from the group consisting of creatine kinase (CK) and its myocardial fraction CK myocardial band (MB), aspartate aminotransferase, lactate dehydrogenase (LDH), α-hydroxybutyrate dehaydrogenase, myoglobin, glutamate oxaloacetate transaminase, glycogen phosphorylase BB, unbound free fatty acids, heart fatty acid binding protein (H-FABP), ischemia-modified albumin, myosin light chain 1, and myosin light chain 2. In some embodiments cardiac troponin, e.g., cTnI, is measured together with CK-MB, e.g., in the same sample, or in samples from the same individual taken at or near the same time.

In some embodiments, cardiac troponin, alone or in combination with other markers or clinical signs, measured as described herein, is used to determine reinfarction. In some embodiments, cardiac troponin, alone or in combination with other markers or clinical signs, measured as described herein, is used to determine characteristics of an infarct, e.g., size, or duration since infarct. In the latter case, fragments of troponin produced by proteolysis in the blood may be compared to total troponin; the greater the proportion of fragments, the more time has elapsed since infarct.

2. Conditions Other than AMI

The methods of the invention also include methods of diagnosis, prognosis, and treatment based on concentration of cardiac troponin in a sample that are useful in conditions other than AMI.

Many conditions include potential or actual cardiac damage, and the ability to measure cardiac troponin at the levels described herein allow for early detection of such damage and early intervention. Knowledge of the concentration of cardiac troponin as measured by the methods and compositions of the invention is useful in diagnosis, prognosis, and determination of treatment for such conditions. Conditions include percutaneous coronary interventions, cardiac surgery, heart failure, acute rheumatic fever, amyloidosis, cardiac trauma (including contusion, ablation, pacing, firing, cardioversion, catheterization and cardiac surgery), reperfusion injury, cardiotoxicity from cancer therapy, congestive heart failure, end-stage renal failure, glycogen storage disease type II (Pompe's disease), heart transplantation, haeomoglobinopathy with transfusion haemosiderosis, hypertension, including gestational hypertension, hypotension, often with arrhythmias, hypothyroidism, myocarditis, pericarditis, post-operative non-cardiac surgery, pulmonary embolism, and sepsis.

In these embodiments, the troponin levels may be determined concomitantly with the levels of marker(s) that are specific for the non-cardiac disease, or other symptoms or clinical signs of the disease; the marker(s) concentration and/or information regarding other symptoms or clinical signs is combined with information regarding cardiac troponin concentrations, determined as described herein, to determine a diagnosis, prognosis, and/or method of treatment. For example, embodiments of the invention may employ, in addition to determination of cardiac troponin concentration, determination of the concentration of one or more of the polypeptides referenced above, or other protein markers useful in diagnosis, prognosis, or differentiation of disease. In some embodiments, a panel of markers for the disease is provided, where the panel includes cardiac troponin concentration, as described herein, and at least on other marker for the disease. The panel may include, 2, 3, 4, 5, 6, 7, 8, 9, 10, 15, 20, or more or individual markers, which including one or more cardiac troponins, e.g., total cTnI. The analysis of a single marker or subsets of marker can be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single marker or a subset of markers in combination with an adjustment of the diagnostic threshold in each of the aforementioned settings to optimize clinical sensitivity and specificity.

a. Cardiac toxicity The compositions and methods of the invention are especially useful in determining and monitoring cardiac toxicity that results from a treatment, e.g., cardiac toxicity of drug treatment. Thus, for example, the invention provides a method of assessing cardiac toxicity of a treatment by measuring cardiac troponin in an individual by i) determining a concentration of cardiac troponin in a sample or determining the concentrations of cardiac troponin in a series of samples from the individual, where at least one of the samples is taken from the individual during or after a time when the individual is receiving the treatment, where the concentration or concentrations is determined by a cardiac troponin assay with a limit of detection for the cardiac troponin in said sample of less than about 50, 40, 30, 10, 5, 4, 3, 2 or 1 pg/ml, e.g., less than about 20 pg/ml; and ii) assessing the degree of cardiac toxicity of the treatment based on said concentration or concentrations. In some embodiments, the treatment is a drug treatment. In some embodiments, the treatment is a non-drug treatment. The method of determining the concentration of cardiac troponin includes any suitable method with the requisite sensitivity, e.g., the methods described herein. In some embodiments, the methods utilize a method of determining a concentration of cardiac troponin in the sample where the method comprises detecting single molecules of troponin, or complexes or fragments thereof.

Especially useful are methods of determination of cardiac toxicity utilizing the cross-reacting antibodies described herein, i.e., antibodies that react with troponin from at least two species, such as humans and another species such as rat, dog, mouse, or monkey. Such antibodies may be used in animal studies of drug toxicity, where the individual for which toxicity is assessed is, e.g., a mammal, such as a rat, mouse, dog, monkey, or other animal used in such studies. Toxicity in various species may be directly compared when the antibody used in the assay is the same antibody, thus reducing variability.

It will be appreciated that the compositions and methods of the invention may be used in conjunction with specific drugs whose side effects include cardiotoxicity in order to monitor the cardiac toxicity. Thus, the invention provides methods of monitoring cardiac toxicity in an individual who is receiving a drug that is known to cause cardiac toxicity by determining the concentration of cardiac troponin in one or more samples obtained from the individual, where the concentration or concentrations is determined by a cardiac troponin assay with a limit of detection for the cardiac troponin in said sample or samples of less than about 50, 40, 30, 10, 5, 4, 3, 2 or 1 pg/ml, e.g., less than about 20 pg/ml; and ii) assessing the degree of cardiac toxicity of the drug treatment based on said concentration or concentrations. In some embodiments the method further includes a step iii) determining whether or not to continue the drug treatment based on the assessment of step ii). Drugs whose side effects include cardiac toxicity are well-known in the art.

C. Serial Testing

A clinical need for very high sensitivity troponin is developing and with it the development of highly sensitive assays for the detection of troponin as described herein. There are three major areas where next-generation troponin assays, e.g. assays for cTnI, can potentially improve current practice. These ways include the earlier diagnosis of an individual than is currently possible with existing routine markers e.g., with troponin, Creatine kinase-MB, and myoglobin, improved risk stratification for future adverse cardiac events among AMI ruleouts, and monitoring of therapeutic drugs that have the potential to cause cardiotoxicity. For AMI patients, the first detectable increase in troponin after the onset of chest pain will enable an earlier diagnosis and triage of patients to the appropriate level of cardiac care. The sensitivity of the analyzer, compositions, and assays described herein has the improved analytical sensitivity and precision to lower the 99th percentile cutoff value. In particular the analyzer system can be used to detect low concentrations of troponin levels and to detect the biological variability (the variability between samples), reference change values, and the index of individuality between samples. The reference change value (RCV) is used to interpret serial results. For serial results to be significantly different, the difference in the numerical results must be greater than the combined variation inherent in the two results. The index of individuality corresponds to the ratio of the within subject biological variation to the between-subject variation. Increasing the analytical sensitivity will result in a lowering of the cutoff concentration at the 99th percentile recommended by The Joint European Society of Cardiology/American College of Cardiology committee for the Redefinition of Myocardial Infarction, and will result in a higher frequency of positive troponin results in patients who present to the emergency room with chest pain. Unless ischemia can be ruled out by clinical or other means, a mildly increased detected level of troponin will produce more false positive cases of AMI. In order to reduce the diagnostic confusion caused by high sensitivity troponin assays, the National Academy of Clinical Biochemistry advocate the use of serial testing, using a more rigorous determination of statistically significant reference change values that are based on the detection or measurement of an analyte's biologic variation in a patient.

The determination of the biological variation for cardiac troponin has not been previously possible due to the lack of analytical sensitivity of assays to reliably measure troponin in the blood of healthy subjects. The availability of high sensitivity troponin assays now enables the reliable detection of troponin due to the normal turnover of cardiac myocytes with the requisite imprecision ($\leq 10\%$). The biological variation data does not influence the interpretation of patients who have a very high troponin concentration, e.g., a 10-fold increases relative to the 99th percentile cutoff. These patients should be immediately admitted and treated without a need for serial troponin testing. In contrast, proper use of the biological variation will be important in the interpretation of minor increases of troponin, i.e., values at or just above the 99th percentile limit when very high sensitivity assays are used. Serial cardiac troponin values that exceed the upper RCV in the clinical context of chest pain increase the likelihood that the patient is suffering an evolving AMI. This interpretation may be valid even if all serial troponin results are below the population-based reference limit (due to the low index of individuality). However, there may be other acute disease processes that can increase troponin concentrations over the short term, such as sepsis. Patients with serial troponin values that are mildly increased but are unchanging would increase the likelihood that a chronic cardiac condition is present that is known to cause cardiac damage (e.g., myocarditis, heart and kidney failure). Patients with declining serial troponin results might indicate a resolving AMI, particularly if there is a history of chest pain from the prior days or week. It should be noted that patients with a positive troponin due to a chronic disease can present with an acute exacerbation and increasing troponin values that mimic an AMI release pattern. Therefore clinical judgment remains paramount in the interpretation of troponin testing.

Using the highly sensitive analyzers described previously, an individual having one or more symptoms of cardiac infarct can be classified with a series of steps comprising: i) obtaining a sample from said individual, ii) detecting the level of troponin in the sample and iii) if the level of troponin is above 10-fold of the 99th percentile, taking a first action with respect to the individual and if the level of troponin is below 10-fold of the 99th percentile taking a second action. In some embodiments, the first action is taken if patient has about a 3-fold to about a 10-fold increase relative to the 99th percentile cutoff. In some embodiments, the first action is taken if patient has about a 4-fold to about a 5-fold increase relative to the 99th percentile cutoff. In some embodiments, the first action is taken if patient has about a 6-fold to about a 7-fold increase relative to the 99th percentile cutoff. In some embodiments, the first action is taken if patient has about an 8-fold to about a 10-fold increase relative to the 99th percentile cutoff. In some embodiments, the first action is taken if patient has about a 1.5-fold to about a 2-fold increase. In some embodiments, the first action is taken if patient has about a 2-fold to about a 2.5-fold increase. In some embodiments, the first action is taken if patient has about a 2.5-fold to about a 3-fold increase. In some embodiments, the first action is taken if patient has about a 3-fold to about a 3.5-fold increase. In some embodiments, the first action is taken if patient has about a 3.5-fold to about a 4-fold increase. In some embodiments, the first action is taken if patient has about a 4-fold to about a 4.5-fold increase. In some embodiments, the first action is taken if patient has about a 4.5-fold to about a 5-fold increase. In some embodiments, the first action is taken if patient has about a 5-fold to about a 5.5-fold increase. In some embodiments, the first action is taken if patient has about a 5.5-fold to about a 6-fold increase. In some embodiments, the first action is taken if patient has about a 6-fold to about a 6.5-fold increase. In some embodiments, the first action is taken if patient has about a 6.5-fold to about a 7-fold increase. In some embodiments, the first action is taken if patient has about a 7-fold to about a 7.5-fold increase. In some embodiments, the first action is taken if patient has about a 7.5-fold to about an 8-fold increase. In some embodiments, the first action is taken if patient has about a 8-fold to about a 8.5-fold increase. In some embodiments, the first action is taken if patient has about an 8.5-fold to about a 9-fold increase. In some embodiments, the first action is taken if patient has about a 9-fold to about a 9.5-fold increase. In some embodiments, the first action is taken if patient has about a 9.5-fold to about a 10-fold increase. In some embodiments the first action is taken if the increase is more than about 2-fold. In some embodiments the first action is taken if the increase is more than about 3-fold. In some embodiments the first action is taken if the increase is more than about 4-fold. In some embodiments the first action is taken if the increase is more than about 5-fold. In some embodiments the first action is taken if the increase is more than about 6-fold. In some embodiments the first action is taken if the increase is more than about 7-fold. In some embodiments the first action is taken if the increase is more than about 8-fold. In some embodiments the first action is taken if the increase is more than about 9-fold. In some embodiments the first action is taken if the increase is more than about 10-fold.

In some embodiments, the individual is a patient being evaluated for a possible cardiac event. In such a case, the first action can be admission of the individual to a hospital, or other appropriate clinical action for treatment of the cardiac event. The second action can be to hold the individual for a period of time for further observation. During the time the individual is held a series of samples are taken from said patient and the level of troponin in each sample detected. In some embodiments, the interval between samples is less than about 4, 3, 2, 1, 0.5 hours apart. In some embodiments, the sample interval is less than about 4 hours apart. In some embodiments, the sample interval is about 1 hour. In some embodiments, the sample interval is about 2 hours. It will be recognized that circumstances in the clinic dictate sample intervals and some degree of variation is acceptable and is encompassed within the invention, as long as results may be reliably interpreted. In some embodiments, in addition to the level of troponin detected in each sample, the rate of change in the level of troponin over two or more samples in the series of samples is detected. In some embodiments, the change in the level of troponin is a decrease. In some embodiments, the change in the level of troponin is an increase. A decision can be made regarding a course of action for said individual based on said rate of change, e.g., if the rate of change in troponin values exceeds a predetermined upper reference rate of change value, the decision is to admit the individual. It will be recognized that other clinical factors well-known to those of skill in the art can be used to modify the decision based on troponin levels, e.g., if other clinical manifestations of acute myocardial infarct are present, such as abnormal EKG, abnormal enzyme levels, physical symptoms, and the like, then the threshold for troponin that leads to an admission is suitably decreased.

The decision to take a first action, e.g., to admit a patient, can also be made if one or more spikes in the level of troponin are seen from sample to sample. The spike can be any increase in the level of troponin detected compared to one or more samples wherein the increase is compared to a threshold level. For example, if the threshold level is determined to be 10 pg/ml and if in one of the sample of the series of samples the troponin level detected is 15 pg/ml, the patient is admitted. In some embodiments, the threshold level is determined from a reference population. In some embodiments, the threshold level is set at a level for an individual, e.g., the initial level of troponin detected from the first sample taken from the patient. In these embodiments, a relative increase indicates a spike, no matter what the absolute values are. In some embodiments, a spike is determined when the troponin level increases 2, 3, 4, 5, 6, 7, 8, 9 10, or more than 10-fold above a reference value for the individual, e.g., a value set at the troponin level in the first sample taken from the individual. Alternatively, a spike in the level of troponin can be seen when comparing troponin levels between samples from the individual. In such a case, no matter what the value of the level of troponin detected, the patient is admitted if the value increases by more than a certain amount, e.g., a patient is admitted when the level of troponin increases by 1, 2, 3, 4, 5, 6, 7, 8, 9, 10, or more than 10 pg/ml as compared to one or more neighboring samples. In some embodiments, the change in the level of troponin indicates an acute cardiovascular disease. In some embodiments, the change in the level of troponin indicates a chronic cardiovascular disease. In some embodiments, the change in the level of troponin indicates cardiotoxicity.

The existing commercial assays lack the sensitivity to low to detect very minor and chronic increases. With the development of high sensitive assays, the utility of cardiac troponin should be re-examined for this application. If proven to be useful, the long-term biological variation and calculation of the RCV will be relevant.

D. Business Methods

The present invention relates to systems and methods (including business methods) for establishing markers of cardiac troponin that can be used for diagnosing, prognosing, or determining a method of treatment of a biological state or a condition in an organism, preparing diagnostics based on such markers, and commercializing/marketing diagnostics and services utilizing such diagnostics. The biological state may be acute myocardial infarct, or cardiac damage due to drug toxicity, or non-AMI states as described herein.

In one embodiment, the business methods herein comprise: establishing one or more cardiac troponin markers using a method comprising: establishing a range of concentrations for said marker or markers in biological samples obtained from a first population by measuring the concentrations of the marker or markers in the biological samples by detecting single molecules of the marker or markers at a level of detection of less than about 50, 20, 10, 5, or 1 pg/ml; and commercializing the one or more markers established in the above step, e.g., in a diagnostic product. The diagnostic product herein can include one or more antibodies that specifically binds to the cardiac troponin marker and a fluorescent moiety that is capable of emitting an average of at least about 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules.

In one embodiment, the business methods herein comprise: establishing a range of normal values for a cardiac troponin marker using a system comprising: establishing a range of concentrations for said cardiac troponin marker in biological samples obtained from a first population by measuring the concentrations of the marker the biological samples by detecting single molecules of the marker at a level of detection less than about 50, 20, 10, 5, or 1 pg/ml; and providing a diagnostic service to determine if an organism has or does not have a state or condition of interest, e.g., AMI, cardiac toxicity due to drug treatment, or a non-AMI condition. A diagnostic service herein may be provided by a CLIA approved laboratory that is licensed under the business or the business itself. The diagnostic services herein can be provided directly to a health care provider, a health care insurer, or a patient. Thus the business methods herein can make revenue from selling e.g., diagnostic services or diagnostic products.

The business methods herein also contemplate providing diagnostic services to, for example, health care providers, insurers, patients, etc. The business herein can provide diagnostic services by either contracting out with a service lab or setting up a service lab (under Clinical Laboratory Improvement Amendment (CLIA) or other regulatory approval). Such service lab can then carry out the methods disclosed herein to identify if a cardiac troponin marker is within a sample.

VII. Compositions

The invention provides compositions useful in the detection and quantitation of cardiac troponin. Compositions include binding partners to cardiac troponin that are labeled with suitable labels for detection by the methods of the invention, pairs of binding partners in which one or both of the binding partners are labeled with suitable labels for detection by the methods of the invention, solid supports to which capture binding partners are attached, in some embodiments also with detection binding partners.

Exemplary embodiments include a composition for the detection of cardiac troponin that includes a binding partner to the cardiac troponin attached to a fluorescent moiety, where the fluorescent moiety is capable of emitting an average of at least about 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the binding partner includes an antibody to the cardiac troponin. In some embodiments, the antibody is a polyclonal antibody. In some embodiments, the antibody is a monoclonal antibody. In some embodiments, the antibody is a cross-reacting antibody, e.g., an antibody that cross-reacts with cardiac troponin from at least two species, e.g., at least two species selected from the group consisting of human, monkey, dog, and mouse. In some embodiments the antibody cross-reacts with cardiac troponins from all of human, monkey, dog, and mouse. In some embodiments, the cardiac troponin is selected from the group consisting of cTnI and cTnT. In some embodiments, the cardiac troponin is cTnI. In some embodiments, cardiac troponin is cTnT. The antibody may specific to a specific region of the troponin molecule, e.g., specific to a region comprising amino acids 27-41 of cardiac troponin I. The fluorescent moiety may contain one or more molecules that comprises at least one substituted indolium ring system in which the substituent on the 3-carbon of the indolium ring contains a chemically reactive group or a conjugated group. The label composition may include a fluorescent moiety that includes one or more dye molecules selected from the group consisting of AlexaFluor 488, 532, 647, 700, or 750. The label composition may include a fluorescent moiety that includes one or more dye molecules selected from the group consisting of AlexaFluor 488, 532, 700, or 750. The label composition may include a fluorescent moiety that includes one or more dye molecules that are AlexaFluor 488. The label composition may include a fluorescent moiety that includes one or more dye molecules that are AlexaFluor 555. The label composition may include a fluorescent moiety that includes one or more dye molecules that are AlexaFluor 610. The label composition may include a fluorescent moiety that includes one or more dye molecules that are AlexaFluor 647. The label composition may include a fluorescent moiety that includes one or more dye molecules that are AlexaFluor 680. The label composition may include a fluorescent moiety that includes one or more dye molecules that are AlexaFluor 700. The label composition may include a fluorescent moiety that includes one or more dye molecules that are AlexaFluor 750.e In some embodiments, the invention provides a composition that includes a set of standards for the determination of a concentration of a cardiac troponin, wherein at least one of the standards is at a concentration of cardiac troponin less than about 20, 15, 10, 5, 4, 3, 2, or 1 pg/ml. In some embodiments, the invention provides a composition that includes a set of standards for the determination of a concentration of a cardiac troponin, wherein at least one of the standards is at a concentration of cardiac troponin less than about 20 pg/ml. In some embodiments, the invention provides a composition that includes a set of standards for the determination of a concentration of a cardiac troponin, wherein at least one of the standards is at a concentration of cardiac troponin less than about 10 pg/ml. In some embodiments, the invention provides a composition that includes a set of standards for the determination of a concentration of a cardiac troponin, wherein at least one of the standards is at a concentration of cardiac troponin less than about 5 pg/ml. In some embodiments, the invention provides a composition that includes a set of standards for the determination of a concentration of a cardiac troponin, wherein at least one of the standards is at a concentration of cardiac troponin less than about 1 pg/ml.

Other compositions of the invention are as described herein.

VIII. Kits

The invention further provides kits. Kits of the invention include one or more compositions useful for the sensitive detection of cardiac troponin, as described herein, in suitable packaging. In some embodiments kits of the invention provide labels, e.g., binding partner such as an antibody that is specific for cardiac troponin, where the binding partner is attached to a fluorescent moiety. In some embodiments kits of the invention provide binding partner pairs, e.g., antibody pairs, that are specific for cardiac troponin, where at least one of the binding partners is a label for a cardiac troponin, as described herein. In some embodiments, the binding partners, e.g., antibodies, are provided in separate containers. In some embodiments, the binding partners, e.g., antibodies, are provided in the same container. In some embodiments, one of the binding partners, e.g., antibody, is immobilized on a solid support, e.g., a microtiter plate or a paramagnetic bead. In some of these embodiments, the other binding partner, e.g., antibody, is labeled with a fluorescent moiety as described herein.

Binding partners, e.g., antibodies, solid supports, and fluorescent labels for components of the kits may be any suitable such components as described herein.

The kits may additionally include reagents useful in the methods of the invention, e.g., buffers and other reagents used in binding reactions, washes, buffers or other reagents for preconditioning the instrument on which assays will be run, and elution buffers or other reagents for running samples through the instrument.

Kits may include one or more standards, e.g., standards for use in the assays of the invention, such as standards of highly purified, e.g., recombinant, human cTnI or human cTnT, or various fragments, complexes, and the like, thereof. Kits may further include instructions.

EXAMPLES

The following examples are offered by way of illustration and not by way of limiting the remaining disclosure.

Unless otherwise specified, processing samples in the Examples were analyzed in a single molecule detector (SMD) as described herein, with the following parameters: Laser: continuous wave gallium arsenite diode laser of wavelength 639 nm (Blue Sky Research, Milpitas, Calif.), focused to a spot size of approximately 2 microns (interrogation space of 0.004 pL as defined herein); flow rate=5 microliter/min through a fused silica capillary of 100 micron square ID and 300 micron square OD; non-confocal arrangement of lenses (see, e.g., FIG. 1A); focusing lens of 0.8 numerical aperture (Olympus); silicon avalanche photodiode detector (Perkin Elmer, Waltham, Mass.).

Example 1

Sandwich Assays for Biomarkers: Cardiac Troponin I (cTnI)

The assay: The purpose of this assay was to detect the presence of cardiac Troponin I (cTnI) in human serum. The assay format was a two-step sandwich immunoassay based on a mouse monoclonal capture antibody and a goat polyclonal detection antibody. Ten microliters of sample were required. The working range of the assay is 0-900 pg/ml with a typical analytical limit of detection of 1-3 pg/ml. The assay required about four hours of bench time to complete.

Materials: the following materials were used in the procedure described below: Assay plate: Nunc Maxisorp, product 464718, 384 well, clear, passively coated with monoclonal antibody, BiosPacific A34440228P Lot # A0316 (5 µg/ml in 0.05 M sodium carbonate pH 9.6, overnight at room temperature); blocked with 5% sucrose, 1% BSA in PBS, and stored at 4° C. For the standard curve, Human cardiac Troponin I (BiosPacific Cat # J34000352) was used. The diluent for the standard concentrations was human serum that was immonodepleted of endogenous cTnI, aliquoted and stored at −20° C. Dilution of the standards was done in a 96 well, conical, polypropylene, (Nunc product #249944). The following buffers and solutions were used: (a) assay buffer: BBS with 1% BSA and 0.1% TritonX-100; (b) passive blocking solution in assay buffer containing 2 mg/ml mouse IgG, (Equitech Bio); 2 mg/ml goat IgG, (Equitech Bio); and 2 mg/ml MAK33 poly, Roche #11939661; (c) detection Antibody (Ab): Goat Polyclonal antibody affinity purified to Peptide 3, (BiosPacific G129C), which was label with a fluorescent dye AlexaFluor 647, and stored at 4° C.; detection antibody diluent: 50% assay buffer, 50% passive blocking solution; wash buffer: borate buffer saline Triton Buffer (BBST) (1.0 M borate, 15.0 M sodium chloride, 10% Triton X-100, pH 8.3); elution buffer: BBS with 4M urea, 0.02% Triton X-100 and 0.001% BSA.

Preparation of AlexaFluor 647 labeled antibodies: the detection antibody G-129-C was conjugated to AlexaFluor 647 by first dissolving 100 ug of G-129-C in 400 uL of the coupling buffer (0.1M NaHCO$_3$). The antibody solution was then concentrated to 50 ul by transferring the solution into YM-30 filter and subjecting the solution and filter to centrifugation. The YM-30 filter and antibody was then washed three times by adding 400 ul of the coupling buffer. The antibody was recovered by adding 50 µl to the filter, inverting the filter, and centrifuging for 1 minute at 5,000×g. The resulting antibody solution was 1-2 ug/ul. AlexaFluor 647 NHS ester was reconstituted by adding 20 ul DMSO to one vial of AlexaFluor 647, this solution was stored at −20° C. for up to one month. 3 ul of AlexaFluor 647 stock solution was added to the antibody solution, which was then mixed and incubated in the dark for one hour. After the one hour, 7.5 ul 1M tris was added to the antibody AlexaFluor 647 solution and mixed. The solution was ultramiltered with YM-30 to remove low molecular weight components. The volume of the retentate, which contained the antibody conjugated to AlexaFluor 647, was adjusted to 200-400 µl by adding PBS. 3 ul 10% NaN3 was added to the solution, the resulting solution was transferred to an Ultrafree 0.22 centrifugal unit and spun for 2 minutes at 12,000×g. The filtrate containing the conjugated antibody was collected and used in the assays.

Procedure: cTnI standard and sample preparation and analysis:

The standard curve was prepared as follows: working standards were prepared (0-900 pg/ml) by serial dilutions of the stock of cTnI into standard diluent or to achieve a range of cTnI concentrations of between 1.2 pg/ml 4.3 µg/ml.

10 µl passive blocking solution and 10 µl of standard or of sample were added to each well. Standards were run in quadruplicate. The plate was sealed with Axyseal sealing film, centrifuged for 1 min at 3000 RPM, and incubated for 2 hours at 25° C. with shaking. The plate was washed five times, and centrifuged until rotor reached 3000 RPM in an inverted position over a paper towel. A 1 nM working dilution of detection antibody was prepared, and 20 µl detection antibody were added to each well. The plate was sealed and centrifuged, and the assay incubated for 1 hour at 25° C. with shaking. 30 µl elution buffer were added per well, the plate was sealed and the assay incubated for ½ hour at 25° C. The plate was either stored for up to 48 hours at 4° C. prior to analysis, or the sample was analyzed immediately.

For analysis, 20 μl per well were acquired at 40 μl/minute, and 5 μl were analyzed at 5 μl/minute. The data were analyzed based on a threshold of 4 sigma. Raw signal versus concentration of the standards was plotted. A linear fit was performed for the low concentration range, and a non-linear fit was performed for the full standard curve. The limit of detection (LoD) was calculated as LOD=(3× standard deviation of zeros)/slope of linear fit. The concentrations of the samples were determined from the equation (linear or non-linear) appropriate for the sample signal.

An aliquot was pumped into the analyzer. Individually-labeled antibodies were measured during capillary flow by setting the interrogation volume such that the emission of only 1 fluorescent label was detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of DMC events/sample. The limit of detection the cTnI assay of the invention was determined by the mean+3 SD method.

Results: Data for a typical cTnI standard curve measured in quadruplicate using the assay protocol is shown in Table 2.

TABLE 2

Standard Curve for cTnI

| cTnI (pg/ml) | Signal | Standard Deviation | % CV |
|---|---|---|---|
| 0 | 233 | 25 | 10.8 |
| 1.5625 | 346 | 31 | 8.9 |
| 3.125 | 463 | 35 | 7.5 |
| 6.25 | 695 | 39 | 5.6 |
| 12.5 | 1137 | 61 | 5.3 |
| 25 | 1988 | 139 | 7.0 |
| 50 | 3654 | 174 | 4.8 |
| 100 | 5493 | 350 | 6.4 |
| 200 | 8264 | 267 | 3.2 |
| 400 | 9702 | 149 | 1.5 |
| 800 | 9976 | 50 | 0.5 |

The sensitivity of the analyzer system was tested in 15 runs and was found routinely to detect sub femtomol/l (fM) levels of calibrator, as shown by the data in Table 3. The precision was 10% at 4 and 12 pg/ml cTnI.

TABLE 3

Instrument Sensitivity

| Calibrator (fM) | Signal counts | CV |
|---|---|---|
| 0 | 11 | |
| 12 | 302 | 9 |
| 60 | 1341 | 8 |
| 300 | 4784 | 7 |

Figure 5:
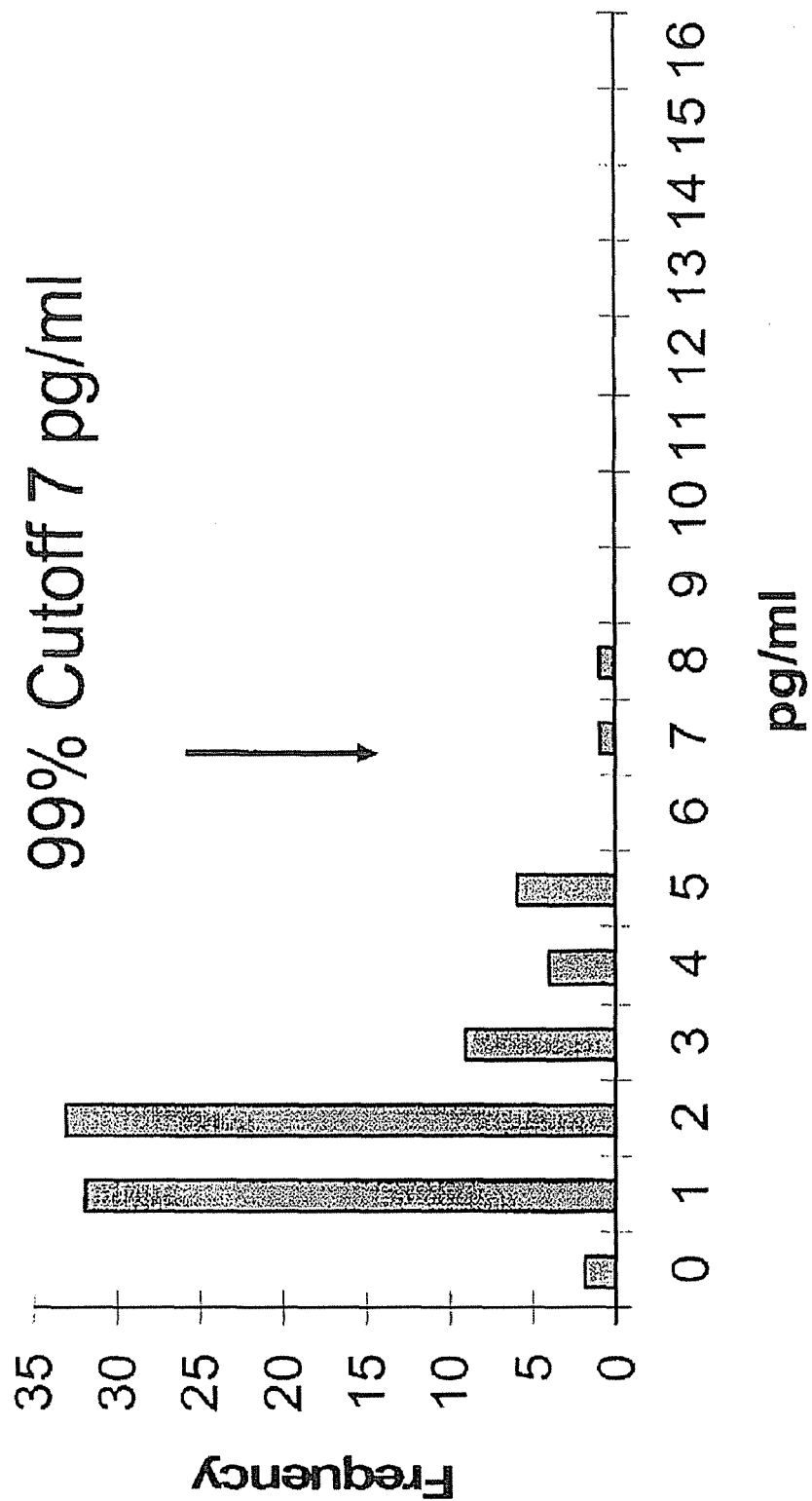
FIG. 5. Biological threshold (cutoff concentration) for cTnI is at a cTnI concentration of 7 pg/ml, as established at the 99th percentile with a corresponding CV of 10%.

Linearized standard curve for the range concentrations of cTnI are shown in FIG. 5.

The analytical limit of detection (LoD) was determined across 15 sequential assays. The LoD was the mean of the 0 std+3 SD (n=4) intra-assay determinations. The average LoD was 1.7 pg/ml (range 0.4-2.8 pg/ml).

The recovery of the sample was determined by analyzing samples of serum that had been immunodepleted of cTnI and spiked with known amounts of cTnI. Table 4 shows the data for sample recovery by the system analyzed over 3 days.

TABLE 4

Sample Recovery

| Spike (pg/ml) | Recovery (mean) | Standard Deviation | % CV |
|---|---|---|---|
| 5 | 5.7 | 0.9 | 16 |
| 15 | 13.7 | 0.2 | 2 |
| 45 | 43 | 0.6 | 2 |
| 135 | 151 | 6.2 | 4 |

The linearity of the assay was determined in pooled human serum that was spiked with cTnI and diluted with standard diluent. The results in Table 5 show the dilutions and % of the signal expected for the corresponding dilution.

TABLE 5

Assay Linearity

| Serum Dilution | % of expected |
|---|---|
| 1:2 | 79 |
| 1:4 | 87 |
| 1:8 | 96 |

These data show that the analyzer system of the invention allows for performing highly sensitive laser-induced immunoassay for sub-femtomolar concentrations of cTnI.

Example 2

Sandwich Bead-Based Assays for TnI

The assays described above use the same microtiter plate format where the plastic surface is used to immobilize target molecules. The single particle analyzer system also is compatible with assays done in solution using microparticles or beads to achieve separation of bound from unbound entities.

Materials: MyOne Streptavidin C1 microparticles (MPs) are obtained from Dynal (650.01-03, 10 mg/ml stock). Buffers use in the assay include: 10× borate buffer saline Triton Buffer (BBST) (1.0 M borate, 15.0 M sodium chloride, 10% Triton X-100, pH 8.3); assay buffer (2 mg/ml normal goat IgG, 2 mg/ml normal mouse IgG, and 0.2 mg/ml MAB-33-IgG-Polymer in 0.1 M Tris (pH 8.1), 0.025 M EDTA, 0.15 M NaCl, 0.1% BSA, 0.1% Triton X-100, and 0.1% NaN3, stored at 4° C.); sand elution buffer (BBS with 4 M urea, 0.02% Triton X-100, and 0.001% BSA, stored at 2-8° C.). Antibodies used in the sandwich bead-based assay include: Bio-Ab (A34650228P (BiosPacific) with 1-2 biotins per IgG) and Det-Ab (G-1129-C (BiosPacific) conjugated to A647, 2-4 fluors per IgG). The standard is recombinant human cardiac troponin I (BiosPacific, cat #J34120352). The calibrator diluent is 30 mg/ml BSA in TBS wEDTA.

Microparticles Coating: 100 ul of the MPs stock is placed in an eppendorf tube. The MPs are washed three times with 100 ul of BBST wash buffer by applying a magnet, removing the supernatant, removing the magnet, and resuspending in wash buffer. After the washes the MPs are resuspended in 100 ul of assay buffer and 15 ug of Bio-Ab are added. The mixture is then incubated for an hour at room temperature with constant mixing. The MPs are washed five times with 1 ml wash buffer as described above. After the washes the MPs are resuspended in 15 ml of assay buffer (or 100 ul to store at 4° C.).

Preparation of Standard and Samples: The standard is diluted with calibrator diluent to prepare proper standard curve (usually 200 pg/ml down to 0.1 pg/ml). Frozen serum and plasma samples need to be centrifuged 10 minutes at room temperature at 13 K rpm. Clarified serum/plasma is removed carefully to avoid taking any possible pellets or floaters and put into fresh tubes. 50 ul of each standard or sample is pipetted into appropriate wells.

Capture Target: 150 ul of MPs (after resuspension to 15 ml in assay buffer+400 mM NaCl) are added to each well. The mixture is incubated on JitterBug, 5 at room temperature for 1 hr.

Washes and Detection: The plate is placed on a magnet and the supernatant is removed after ensuring that all MPs are captured by the magnet 250 ul of wash buffer are added after removing the plate from the magnet. The plate is then placed on the magnet and the supernatant is removed after ensuring that all MPs are captured by the magnet. 20 ul Det-Ab are added per well (Det-Ab to 500 ng/ml is diluted in assay buffer+400 mM NaCl)). The mixture is incubated on Jitter-Bug, 5 at room temperature for 30 min.

Washes and Elution: The plate is placed on a magnet and washed three times with wash buffer. The supernatant is removed after ensuring that all MPs are captured by the magnet and 250 ul of wash buffer are added. After the washes the samples are transferred into a new 96-well plate. The new plate is then placed on the magnet and the supernatant is removed after ensuring that all MPs are captured by the magnet. 250 ul of wash buffer are then added after removing the plate from the magnet. The plate is then placed on the magnet and the supernatant is removed after ensuring that all MPs are captured by the magnet. 20 ul of elution buffer are then added and the mixture is incubated on JitterBug, 5 at room temperature for 30 min.

Filter out MPs and transfer to 384-well plate: The standard and samples are transferred into a 384-well filter plate placed on top of a 384-well assay plate. The plate is then centrifuged at room temperature at 3000 rpm with a plate rotor. The filter plate is removed and the appropriate calibrators are added. The plate is covered and is ready to be run on SMD.

SMD: An aliquot is pumped into the analyzer. Individually-labeled antibodies are measured during capillary flow by setting the interrogation volume such that the emission of only 1 fluorescent molecule is detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of DMC events/sample. The limit of detection the cTnI assay of the invention is determined by the mean+3 SD method.

Example 3

Concentration Range for cTnI in a Population of Normal Non-Diseased Subjects

A reference range or normal range for cTnI concentrations in human serum was established using serum samples from 88 apparently healthy subjects (non-diseased). A sandwich immunoassay as described in Example 1 was performed and the number of signals or events as described above were counted using the single particle analyzer system of the invention. The concentration of serum troponin I was determined by correlating the signals detected by the analyzer with the standard curve as described above. All assays were perfumed in quadruplicate.

In accordance with recommendations by the current European and American Cardiology Societies (ESC/ACC) troponin assays should quantify accurately the 99th percentile of the normal range with an assay imprecision (CV) of less than 10% in order to distinguish reliably between patients with ACS and patients without ischemic heart disease, and risk stratification for adverse cardiac events. The assay showed that the biological threshold (cutoff concentration) for TnI is at a TnI concentration of 7 pg/ml, which is established at the 99th percentile with a corresponding CV of 10% (FIG. 5). At the 10% CV level the precision profile points at a TnI concentration of 4 and 12 pg/ml.

Figure 6:
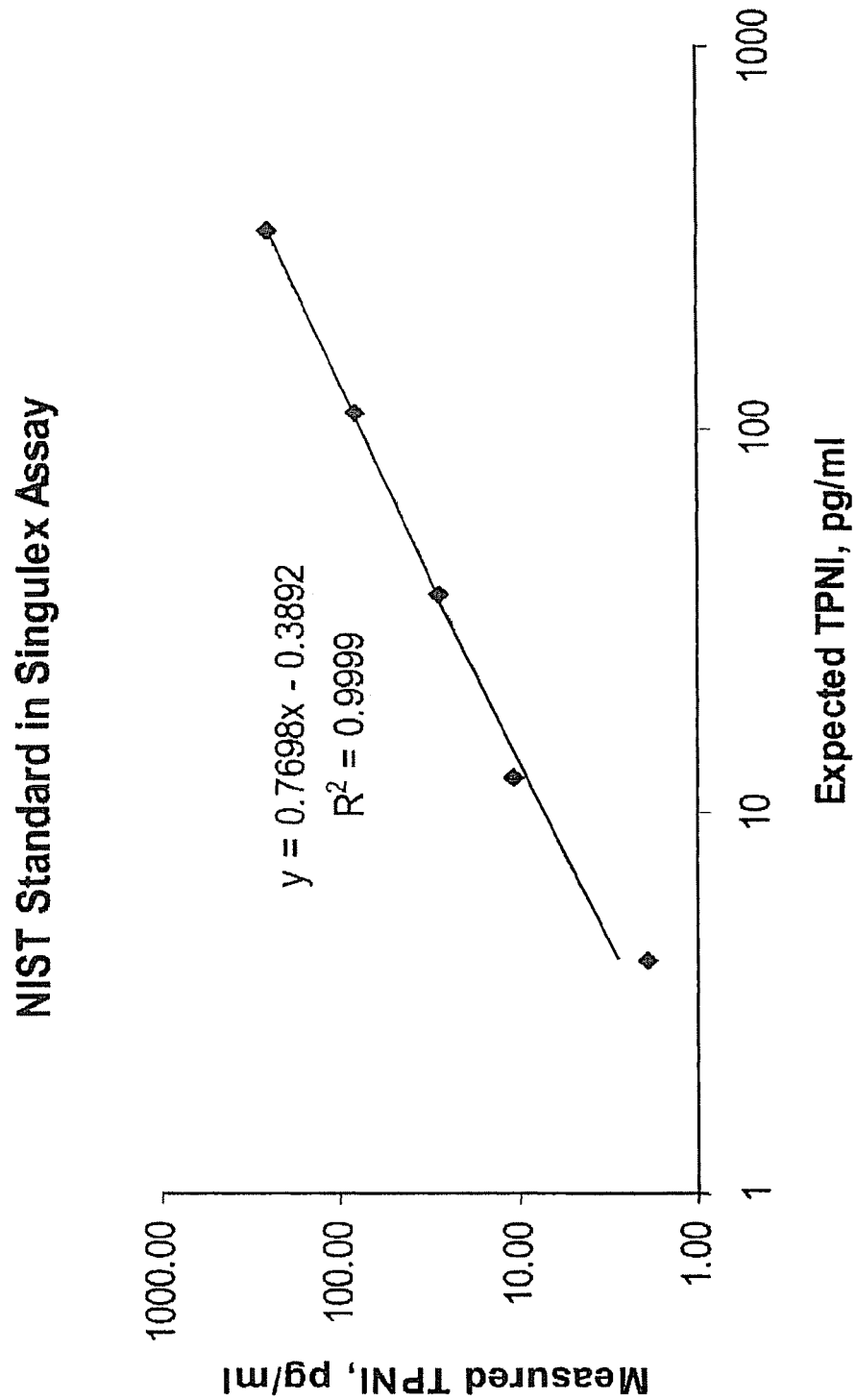
FIG. 6. Correlation of assay results of cTnI determined using the analyzer system of the invention with standard measurements provided by the National Institute of Standards and Technology (R2=0.9999).

In addition, the assay correlates well with the Troponin-I standard measurements provided by the National Institute of Standards and Technology (FIG. 6).

The assay of the invention is sufficiently sensitive and precise to fulfill the requirements of the ESC/ACC, and it is the most sensitive assay for cardiac troponin I when compared to assays such as those described by Koerbin et al. (Ann Clin Biochem, 42:19-23 (2005). The assay of the invention has a 10-20 fold greater sensitivity than that currently available assays, which has determined the biological threshold range to be 111-333 pg/ml cTnI.

Example 4

Detection of Early Release of TnI into the Circulation of Patients with Acute Myocardial Infarction (AMI)

Study 1: 47 samples were obtained serially from 18 patients that presented with chest pain in the emergency department (ED). These patients all had non-ST elevated ECG were, and were diagnosed with AMI. The concentration of cTnI in the initial samples from all 18 patients was determined according to a commercial assay at the time of admission to the emergency room to be <350 pg/ml (10% cutpoint), and 12 were <100 pg/ml (99th %) percentile. These samples were tested at later times using the same commercial assay, and were determined to test positive for cTnI. The same serum samples were also assayed for TnI according to the assay of the invention as described in Examples 1 and 3, and the results compared to the results obtained using the commercial assay.

Figure 7:
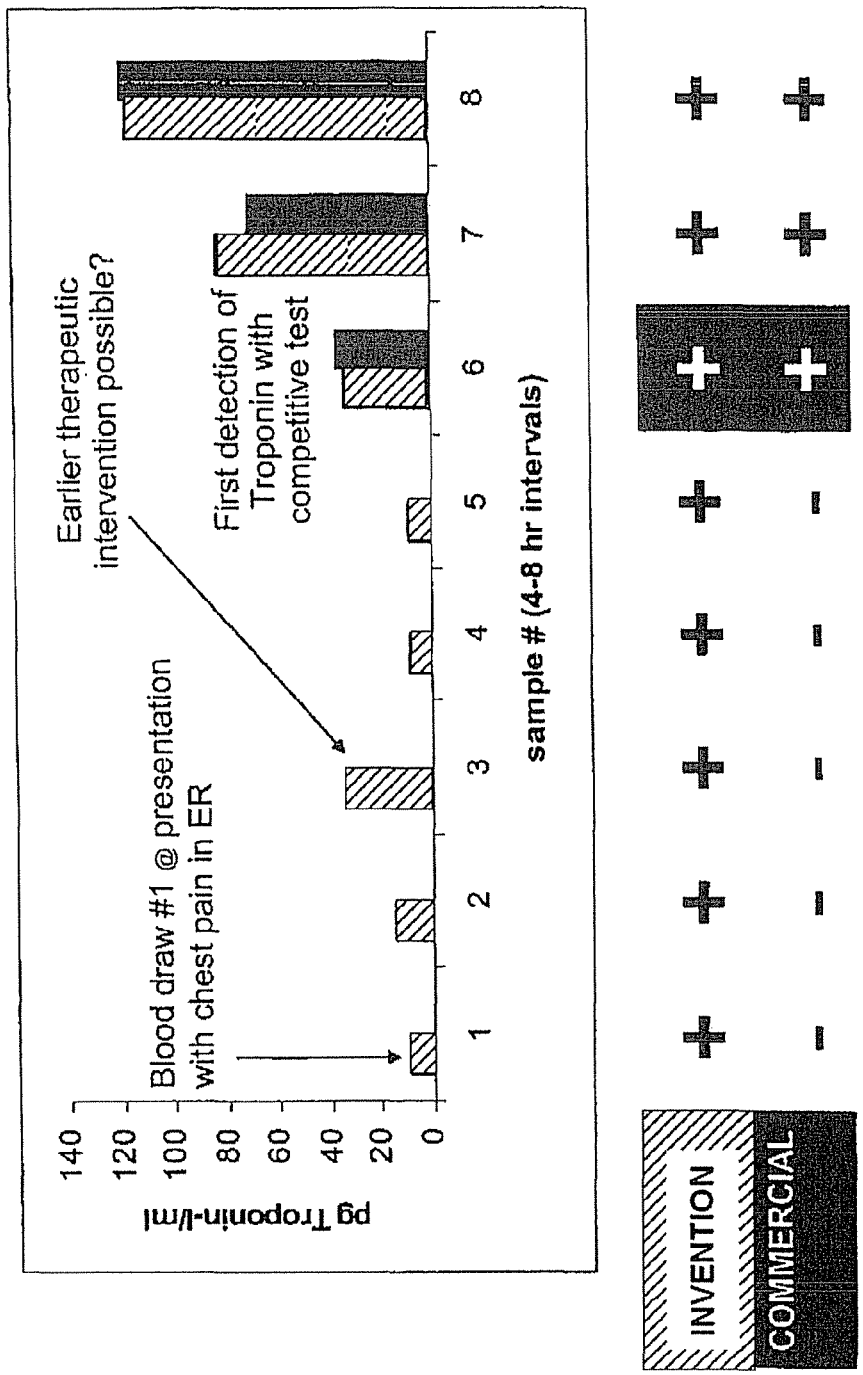
FIG. 7. Detection of cTnI in serial serum samples from patients who presented at the emergency room with chest pain. The measurements made with the analyzer system of the invention were compared to measurements made with a commercially available assay.

Blood was drawn for the first time at the time the patient presented with chest pain (sample 1), and subsequently at intervals between 4-8 hours (samples 2 at 12 hours; sample 3 at 16 hours; sample 4 at 24 hours; sample 5 at 30 hours; sample 6 at 36 hours; sample 7 at 42 hours; and sample 8 at 48 hours). The serum was analyzed by the methods of the invention and by a current commercial method, and the results obtained are shown in FIG. 7. The analyzer of the invention detected TnI at the time the patient presented with chest pain (sample 1), while the commercial assay first detected cTnI at a much later time (sample 6 at 36 hours). The concentration of TnI in sample 3 exceeded the biological threshold level that was established using the analyzer of the invention (7 pg/ml, see FIG. 5), and indicated that sample 3 is positive for TnI to suggest the incidence of a cardiac event. The biological threshold for the commercial assay lies between 111 and 333 pg/ml of TnI. Accordingly, sample 3 would not have been considered to indicate a possible cardiac event.

In addition, the methods and compositions of the present invention allow for much earlier diagnosis and possible intervention based on cardiac troponin levels, as evidenced by results for the first sample taken from the patients. In the 3 cases that had initial commercial assay cTnI values of between 100 and 350 ng/ml, all were positive for cTnI by the analytical methods of the invention (i.e., cTnI over 7 pg/ml). In the 12 cases that had initial commercial cTnI values of less than 100 pg/ml, 5 were determined to be positive for a cardiovascular event according to the assay of the invention (i.e., cTnI over 7 pg/ml). The prospective use of the assay of the invention would have detected 53% more AMI cases than the current commercial assay when the admission sample was tested.

Figure 8:
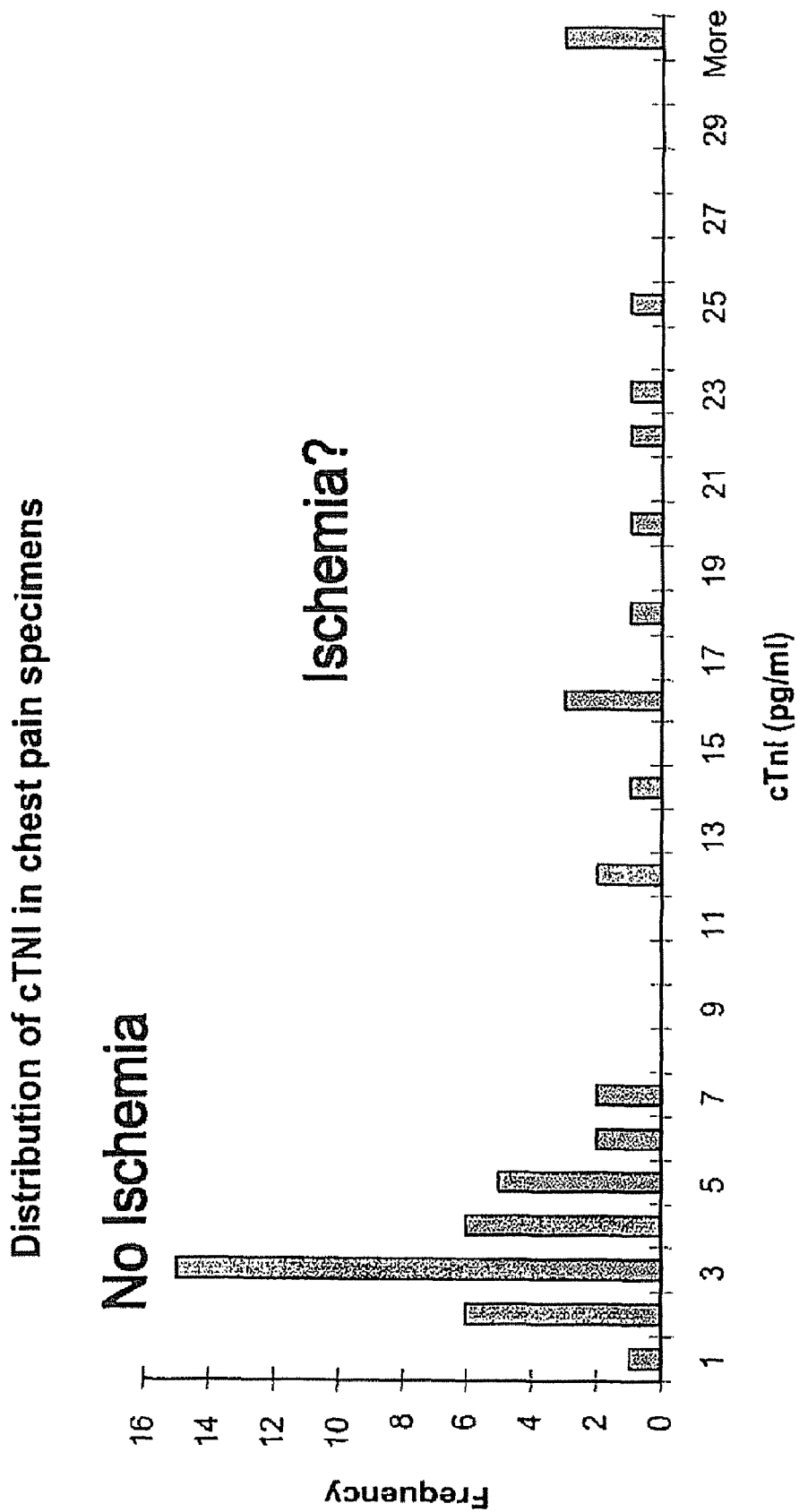
FIG. 8. Distribution of normal biological concentrations of cTnI (No Ischemia) and concentrations of cTnI in serum samples from patients presenting with chest pain.

Study 2: 50 additional serum samples, which tested negative according to the commercial assay, were tested using the analyzer and assay of the invention. The results are shown in FIG. 8. Of the 50 samples, 36 were within the 99th % and determined to be within the normal range established by the assay of the invention. However, the remaining 14 samples that were determined to be within the commercial "normal" or non-diseased range, tested above the biological threshold established by the invention.

Therefore, the high sensitivity cTnI assay of the invention allows for the detection of myocardial damage in patients when cTnI serum levels are below threshold values by commercially available technology. The use of the highly sensitive and precise cTnI assay of the invention enables detection of AMI earlier than with existing cTnI assays, and thereby provides the opportunity for appropriate diagnosis and early medical intervention to improve the outcome.

Example 5

Sandwich Bead-Based Assays for TnI

The single particle analyzer system is compatible with assays done in solution using microparticles or beads to achieve separation of bound from unbound entities, e.g., in the analysis of cardiac troponin I.

Materials: MyOne Streptavidin C1 microparticles (MPs) are obtained from Dynal (650.01-03, 10 mg/ml stock). Buffers use in the assay include: 10× borate buffer saline Triton Buffer (BBST) (1.0 M borate, 15.0 M sodium chloride, 10% Triton X-100, pH 8.3); assay buffer (2 mg/ml normal goat IgG, 2 mg/ml normal mouse IgG, and 0.2 mg/ml MAB-33-IgG-Polymer in 0.1 M Tris (pH 8.1), 0.025 M EDTA, 0.15 M NaCl, 0.1% BSA, 0.1% Triton X-100, and 0.1% NaN3, stored at 4° C.); sand elution buffer (BBS with 4 M urea, 0.02% Triton X-100, and 0.001% BSA, stored at 2-8° C.). Antibodies used in the sandwich bead-based assay include: Bio-Ab (A34650228P (BiosPacific) with 1-2 biotins per IgG) and Det-Ab (G-1129-C (BiosPacific) conjugated to A647, 2-4 fluors per IgG). The standard is recombinant human cardiac troponin I (BiosPacific, cat #J34120352). The calibrator diluent is 30 mg/ml BSA in TBS wEDTA.

Microparticles Coating: 100 ul of the MPs stock is placed in an eppendorf tube. The MPs are washed three times with 100 ul of BBST wash buffer by applying a magnet, removing the supernatant, removing the magnet, and resuspending in wash buffer. After the washes the MPs are resuspended in 100 ul of assay buffer and 15 ug of Bio-Ab are added. The mixture is then incubated for an hour at room temperature with constant mixing. The MPs are washed five times with 1 ml wash buffer as described above. After the washes the MPs are resuspended in 15 ml of assay buffer (or 100 ul to store at 4° C.).

Preparation of Standard and Samples: The standard is diluted with calibrator diluent to prepare proper standard curve (usually 200 pg/ml down to 0.1 pg/ml). Frozen serum and plasma samples need to be centrifuged 10 minutes at room temperature at 13 K rpm. Clarified serum/plasma is removed carefully to avoid taking any possible pellets or floaters and put into fresh tubes. 50 ul of each standard or sample is pipetted into appropriate wells.

Capture Target: 150 ul of MPs (after resuspension to 15 ml in assay buffer+400 mM NaCl) are added to each well. The mixture is incubated on JitterBug, 5 at room temperature for 1 hr.

Washes and Detection: The plate is placed on a magnet and the supernatant is removed after ensuring that all MPs are captured by the magnet. 250 ul of wash buffer are added after removing the plate from the magnet. The plate is then placed on the magnet and the supernatant is removed after ensuring that all MPs are captured by the magnet. 20 ul Det-Ab are added per well (Det-Ab to 500 ng/ml is diluted in assay buffer+400 mM NaCl)). The mixture is incubated on Jitter-Bug, 5 at room temperature for 30 min.

Washes and Elution: The plate is placed on a magnet and washed three times with wash buffer. The supernatant is removed after ensuring that all MPs are captured by the magnet and 250 ul of wash buffer are added. After the washes the samples are transferred into a new 96-well plate. The new plate is then placed on the magnet and the supernatant is removed after ensuring that all MPs are captured by the magnet. 250 ul of wash buffer are then added after removing the plate from the magnet. The plate is then placed on the magnet and the supernatant is removed after ensuring that all MPs are captured by the magnet. 20 ul of elution buffer are then added and the mixture is incubated on JitterBug, 5 at room temperature for 30 min.

Filter out MPs and transfer to 384-well plate: The standard and samples are transferred into a 384-well filter plate placed on top of a 384-well assay plate. The plate is then centrifuged at room temperature at 3000 rpm with a plate rotor. The filter plate is removed and the appropriate calibrators are added. The plate is covered and is ready to be run on SMD.

SMD: An aliquot is pumped into the analyzer. Individually-labeled antibodies are measured during capillary flow by setting the interrogation volume such that the emission of only 1 fluorescent molecule is detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of DMC events/sample. The limit of detection the cTnI assay of the invention is determined by the mean+3 SD method.

Example 6

Cross-Reacting Antibodies

Cross-reacting antibody pairs were prepared for cross-reactivity with human, monkey, dog, and rat. Assays were performed on serum samples using a protocol essentially as described in Example 5, i.e., capture antibody was immobilized on paramagnetic beads. Results are shown in FIGS. 9 and 10. This Example demonstrates that antibodies that cross-react to several species may be produced and used to measure cardiac troponin I at very low limits of detection, i.e., less than 1 pg/ml across human, monkey, dog, and rat.

Example 7

Accurate and Reproducible IA-Based Technology

This example describes a IA-based technology that can accurately and reproducibly measure proteins with a sensitivity of 10-100 femtogram (fg)/ml with a dynamic range of >4.5 logs in sample volumes of 50-150 ul.

Materials and Methods

Materials

Antibodies and analytes (recombinant) were obtained from R&D Systems (Minneapolis, Minn.). Fluorescent dyes and biotin succimidyl ester, used to label antibodies, were obtained from Invirtogen (San Diego, Calif.). Rat, dog, and monkey cTnI were purified from natural sources and obtained from Hytest (Sweden). Human lithium citrate plasma specimens were purchased from Interstate blood bank. Streptavidin coated paramagnetic microparticles (MPs) were obtained from Invitrogen. Antibodies were labeled with fluorescent dye (detection antibody, usually polyclonal) and biotin (capture antibody, usually monoclonal) using manufacturers recommendations. MPs were coated with biotinylated antibody under saturation conditions, washed and stored in assay buffer (1% BSA based buffer containing non-ionic detergent and heterophile/HAMA antibody blocking reagents).

Immunoassays

Unless stated otherwise, the typical immunoassay was performed as follows. Samples or standards (e.g. 50 ul-100 ul) were diluted with assay buffer containing capture antibody coated MPs (e.g. 150 ul) and incubated in a 96 well plate for one to two hours at 25° C. with shaking. MPs were separated using a magnetic bed (Ambion, Tex.). Supernatant was removed and then 20 ul of detection antibody was added and incubated for 60 minutes at 25° C. with shaking. The MPs were again magnetically separated and washed six times using buffered saline plus surfactant. After removal of residual wash buffer, 20 ul of elution buffer was added. This reagent disrupted antibody-analyte interactions and resulted in the release of detection antibody from the MPs. The solution in each 96-well was then transferred to a 384-well filter plate and centrifuged at 3,000 RPM for three minutes to separate detection antibody in elution buffer from MPs. The eluted and filtered material in the 384-well plate was then placed into the analyzer system.

Analyzer System

The analyzer system is based upon single molecule counting technology. Liquid is sipped well and pumped through a capillary with a 100 micro-meter diameter. The liquid passes through a interrogation space comprising a laser for fluorescent dye excitation and fluorescent emission is detected via confocal microscopy. The 4.5 plus log dynamic reporting range was obtained by using a combination of output signals. At low analyte concentrations, individual fluorescently-tagged detection antibody molecules were counted as they passed through the interrogation space in the instrument's flow cell. This signal is a sum of all such measured events over a set time interval and is termed detected events (DE). At higher concentrations of analyte, multiple molecules were detected simultaneously in the flow, and signal was measured as photon events (PE) over the time interval. At this point, total light measured during the time event was used. At the highest concentrations of analyte, total photons (TP), the sum of all photon events, was used. DE, PE and TP signal were used to generate a weighted four-parameter curve fit for each signal type. Finally, a computer algorithm was created that combined these three curve fits into a weighted single curve fit that provided a >4.5 log linear reporting range.

Results

Reporting Range, Linearity, Accuracy and Reproducibility

Figure 11:
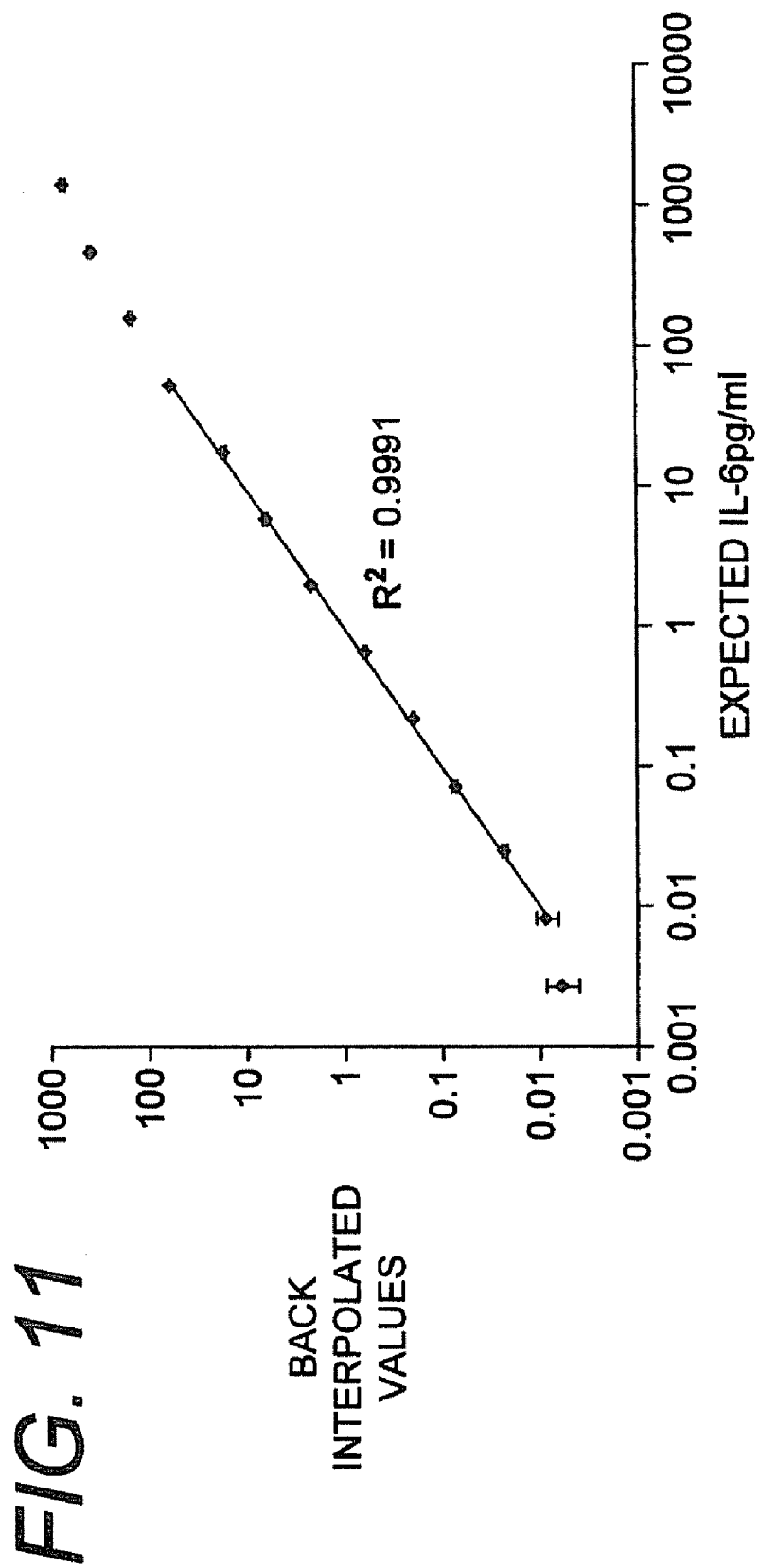
FIG. 11. Linear regression analysis of back interpolated values from a typical human IL-6 standard Curve FIG. 12. Graph showing interassay precision; back interpolation of cTnI standard curves generated over 8 consecutive assay runs.
Figure 12A:
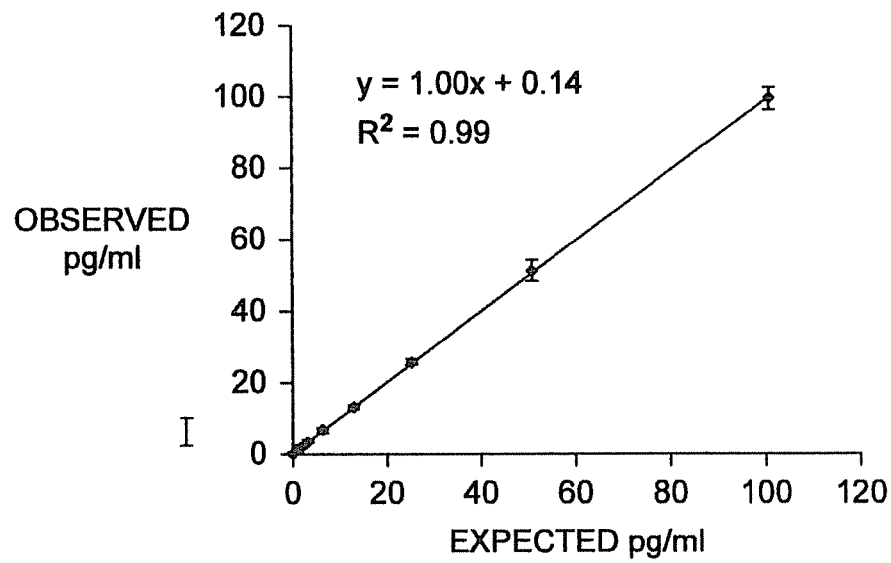
FIG. 12A shows the full range of values.
Figure 12B:
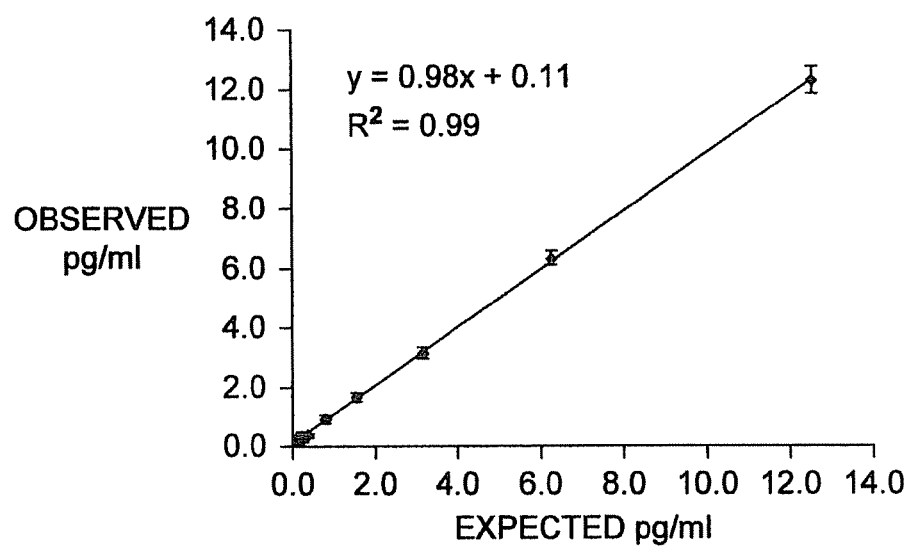
FIG. 12B shows the low end range of quantification.

To determine the reporting range for the IL-6 assay, recombinant human IL-6 was serially diluted (1 ng/ml to 10 fg/ml) in a goat serum-based diluent. Samples of 100 ul were run in quadruplicate. The reporting range of a typical bioassay is presented in FIG. 11. Resulting signal was back interpolated using the curve fit algorithm. A linear response ($R^2=0.99$; $y=0.97+6.4$) was observed from 10 fg/ml to 400 pg/ml, representing an approximate 4.5 log reporting range (FIG. 11). Accuracy was determined by measuring spike recovery of analyte (IL-6 and human cardiac troponin-I, cTnI) into panels of human plasma. The IL-6 and cTnI assays and spike levels of 5 and 50 pg/ml, average % recoveries were between 90% and 110% for both analytes at both concentrations (data not shown). Results from performing the cTnI immunoassay over eight consecutive runs and back interpolating the standard curves are presented in FIG. 12. In these experiments, the highest concentration standard used was 100 pg/ml. A linear ($R^2=0.99$) response was observed at both the high and low ends of the standard curve shown. The % CV for the 8 assay runs for back interpolated determinations was <10% between for all values >0.78 pg/ml. The % CV was 16% and 23% for the 0.39 and 0.2 pg/ml values, respectively.

Sensitivity

Sensitivity or LoD for the analyzer, composition, and methods of the immunoassay system varied from analyte to analyte. Table 6 depicts the LoD for 10 different human immunoassays. Larger sample volumes consistently resulted in lower LoDs and enhanced sensitivity. For example, sample volumes >50 ul resulted in LoDs ranging from 0.01 pg/ml (human IL-6) to 0.12 pg/ml (human VEGF). As sample volumes decreased, LoD's increased in a proportional manner. All of the assays were performed in a two-step manner with 1-2 hours of capture and 1 hour of detection.

TABLE 6

The effect of sample volume on immunoassay sensitivity (LoD)

| Analyte | Volume (ul) | LoD pg/ml | Volume (ul) | LoD pg/ml |
| --- | --- | --- | --- | --- |
| MCP-1 | 200 | 0.03 | 20 | 0.25 |
| RANTES | 100 | 0.05 | 20 | 0.3 |
| VEGF | 100 | 0.12 | 20 | 1.0 |
| IL-8 | 50 | 0.12 | 20 | 0.3 |
| IL-1a | 200 | 0.01 | 20 | 0.1 |
| IL-7 | 200 | 0.02 | 10 | 0.3 |
| IL-6 | 100 | 0.01 | 10 | 0.15 |
| TNF-a | 200 | 0.02 | 10 | 0.4 |
| IL-1B | 150 | 0.02 | 10 | 0.3 |
| cTPN-I | 100 | 0.11 | 10 | 1.2 |

The effect of incubation time on assay sensitivity is shown in Table 7. In this case a single step cTnI assay was performed using 50 ul of sample and simultaneous capture and detection reactions. As incubation times, increased assay sensitivity improved. This was due to an improvement in slope response as a function of time. Of note, even with a 15 minute incubation a LoD of 0.61 pg/ml was achieved (using the NIST reference material).

TABLE 7

The effect of incubation time on a one step cTnI immunoassay sensitivity (LoD)

| Time (minutes) | Background | Slope | LoD pg/ml |
|---|---|---|---|
| 120 | 184 | 152 | 0.241 |
| 60 | 172 | 102 | 0.336 |
| 30 | 173 | 90 | 0.383 |
| 15 | 193 | 64 | 0.61 |

To assess species cross reactivity, antibodies were chosen for the cTnI bioassay that should cross react across these species based upon cTnI homology at reactive epitopes. Serial dilutions of individual cTnIs from human (NIST material), rat, dog and monkey were made in a BSA-based diluent. Sample volumes of 50 ul were then tested with the analyzer system. The findings are presented in Table 8. Slopes of the dilution curves ranged from 68-138, and LoDs ranged 0.14-0.72 pg/ml. Bias against the human NIST standard was 1.6, 2.0, and 4.9 for rat, dog and monkey, respectively. The reason for this bias is not clear but may reflect inconsistencies in analyte value assignment by the manufacturer. Regardless all 4 species cTnI provided immunoassays with LoDs <1 pg/ml.

TABLE 8

Species cross reactivity of the analyzer system cTnI immunoassay.

| Species of cTnI | Background | Slope | LoD (pg/ml) |
|---|---|---|---|
| Human (NIST) | 143 | 138 | 0.19 |
| Monkey | 147 | 28 | 0.72 |
| Dog | 138 | 68 | 0.58 |
| Rat | 138 | 84 | 0.14 |

Figure 13:
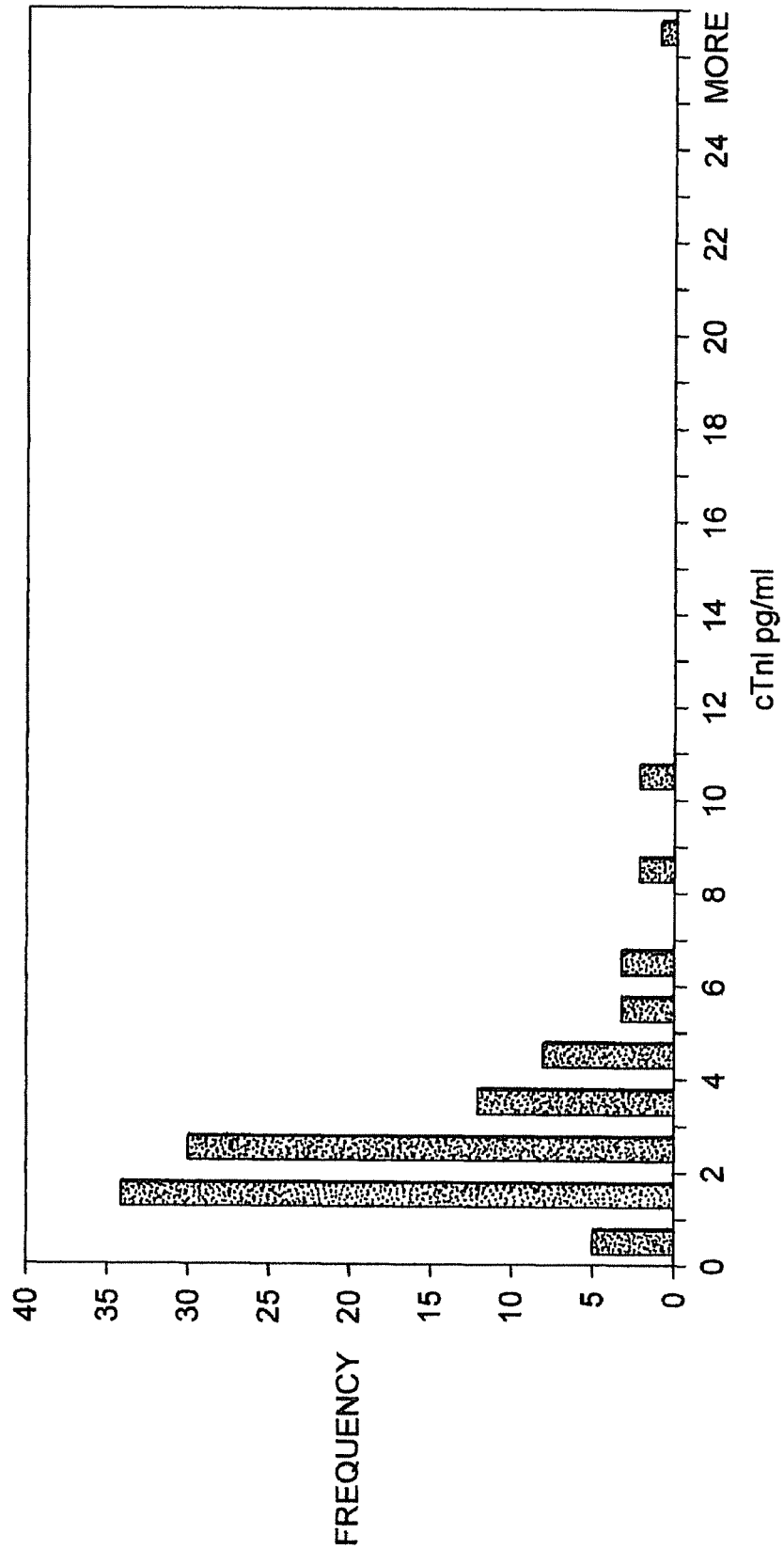
FIG. 13. Frequency distribution of cTnI in lithium heparin plasma specimens obtained from 100 different blood donors.

The sensitivity of the human cTnI assay was employed to define the range of cTnI in human plasma obtained from 100 human blood donors (50 ul sample size). The results are presented in FIG. 13. The values ranged from <2 pg/ml to 39 pg/ml with an average value of 2.19 pg/ml (4.1SD). Three plasma had values <0.2 pg/ml which was the LoD. The value for the 99$^{th}$ percentile was 9 pg/ml. If the one apparent outlier of 39 pg/ml was removed from the data set the mean for the population was 1.83 pg/ml (1.9SD) with the 99$^{th}$ percentile at 8 pg/ml.

This example shows the combination of ultra-sensitive flow detection with MP based IA technology provides protein bioassays with analytical LODs in the fg/ml range, which is approximately 10-fold more sensitive than previously demonstrated. We have applied this technology to create important bioassays for clinically useful protein biomarkers, such as cTnI and IL-6. This new development in IA technology provides accurate, sensitive and reproducible quantitative bioassays with a dynamic range of measurement in small sample volumes across multiple mammalian species.

The analyzer, compositions, and methods provide enhanced sensitivity via two mechanisms. First, unlike analog systems that count total light (e.g. a calorimetric 96-well plate reader), the analyzer system separates background fluorescent signal from antibody-tagged signal by thresholding out the background signal and measuring each fluorescently-labeled detection antibody as a digital event (Wu et al). Second, the MP solid phase has been designed to minimize non-specific binding (NSB) of fluorescently-labeled detection antibodies. Furthermore, incubations are performed in 96-well plates with polypropylene wells that have very low protein binding capacity and, thus, low NSB. With the analyzer system, when a fluorescently-tagged detection antibody is released from the MPs, the level of NSB in reactions that contain no analyte is very low. These characteristics have allowed us to use relatively high concentrations of detection antibody (100-500 ng/ml) which favor a steep assay response while maintaining a very low background.

The sensitivity of the analyzer, compositions, and methods allows for the measurement and quantification of biomarkers in normal, non-disease states. This is an important foundation that must be established before changes in biomarkers can be used to diagnose disease and monitor progression and therapeutic interventions. We quantified the levels of cTnI in a panel of lithium heparin plasma obtained from 100 human blood donors. The mean and range of cTnI values in this plasma are similar to those reported previously for serum specimens. In the case of cTnI, we demonstrated an analytical LoD of 0.2 pg/ml and a 10% CV cutpoint between 0.78 and 1.6 pg/ml. Since normal subjects have serum and plasma cTnI levels between 0.3-9 pg/ml (average 2-3 pg/ml), increases from these normal levels can be measured with a high level of precision in most human serum and plasma samples. We have also shown that the analyzer, compositions, and methods provide analytical sensitivities <1 pg/ml across multiple mammalian species that are often used in preclinical studies, such as monkey, rat and dog. This finding may have significant applications in drug development where the monitoring of cardiac toxicity in preclinical animal models is desired.

The enhanced sensitivity that analyzer, compositions, and methods provide has additional benefits; namely sample volume requirements and incubation times. For example, to achieve highest levels of sensitivity, often sample volume is increased in IA applications. By providing a more some sensitive approach, less sample volume can be used with the analyzer system thus enabling the preservation of precious specimens. One of the limitations of rapid tests used today near patient settings is a lack of sensitivity compared to automated system counterparts. This is attributable to technology, sample volume, as well as incubation times. We demonstrated a proportional increase in sensitivity with incubation times. The analyzer, compositions, and methods have sensitivities of 10-100 fg/ml using 100 ul of sample and one to two hours incubation. Using a one-step modification for the analyzer system as described above we were able to reduce the incubation times to 15 minutes with an approximate LoD of 0.6 pg/ml with 50 ul of sample. This is 50-200 times more sensitive than a variety of commercially available cTnI assays on automated platforms. Taken together these data demonstrate the potential for the development of a clinically useful rapid sub pg/ml IA using single molecule counting as incorporated in the analyzer system Approaches to enhance ELISA sensitivity have involved the use of a variety of technologies including signal amplification (e.g. double enzymatic amplification). Although high sensitivity IAs have been demonstrated using this approach, often the magnitude of assay dynamic range is compromised to a 1.5-2.0 log range. If the analyte of interest exists in a wide biological range, such as for cytokines, then a sample will often require numerous dilutions to achieve the correct concentration for measurement in the IA.

The analyzer system builds single molecule detection combined with MP IA technology to provide highly sensitive immunoassays. It also provides a broad dynamic reporting range and flexible sample volume usage. Dynamic or broad reporting range is important in the ability to detect both normal and disease states in one standardized bioassay. The flexibility of sample volume usage can be used to determine multiple quantifications from a small sample or to conserve samples. If ultimate sensitivity is not required, for example if the analyte is in the 20-100 pg/ml range, multiple analyses can be made. In the case where the normal range of a protein biomarker is in the low 10-20 pg/ml range, a highly sensitive assay could be combined with small sample requirements to enable sample conservation and potential sample usage for the measurement of additional biomarkers. This could be especially important when analyzing rodent samples or human repository specimens.

Example 8

Short and Long-Term Biological Variation for Cardiac Troponin I Using a High Sensitivity Assay: Implications for Clinical Practice As serial testing will be important in the interpretation of low concentrations, we determined the short-term (4-hours) and long-term (8-weeks) biological variability, reference change values and index of individuality for cTnI. Assays for cardiac troponin have been the mainstay for diagnosis of acute myocardial infarction (AMI) and risk stratification for future adverse cardiac events. In the clinical context of myocardial ischemia, the European Society/American College of Cardiology have redefined AMI to be predicated on an increase in cardiac troponin above the $99^{th}$ percentile of a healthy population with a imprecision of 10% or less. Up until recently, there have been very few commercial assays that can detect cardiac troponin I (cTnI) concentrations in healthy subjects with the requisite precision. Recently, a new high sensitivity troponin assay was developed using single photon fluorescence detection. In preliminary studies, this assay had a sensitivity of 0.2 ng/L, and a 10% coefficient of variance (CV) at 1.8 ng/L. The $99^{th}$ percentile cutoff concentration obtained from a healthy population was lower at 10 ng/L than any of the other commercial assays for cTnI.

The clinical need for very high sensitivity troponin has been recently reviewed. There are three major areas where next-generation cTnI assays can potentially improve current practice: earlier diagnosis than is currently possible with existing routine markers (troponin, Creatine kinase-MB, and myoglobin), improved risk stratification for future adverse cardiac events among AMI ruleouts, and monitoring of therapeutic drugs that have the potential to cause cardiotoxicity. For AMI patients, the first detectable increase in troponin after the onset of chest pain will enable an earlier diagnosis and triage of patients to the appropriate level of cardiac care. Melanson et al. showed that use of a high-sensitivity cTnI assay was positive earlier than use of a lower sensitivity assay 64% of confirmed AMI cases. For risk stratification, use of the lowest troponin cutoff (i.e., $99^{th}$ percentile) in the TIMI-TACTICS II trial identified 12% more cases of patients who were subsequently determined to be at high risk for future AMI and cardiac deaths. For cardiotoxicity, chemotherapeutic drugs such as the anthracyclines release small amounts of troponin as the result of injury to the heart. Use of a high-sensitivity troponin assay may enable detection of other drugs that are cardiotoxicity (e.g., cyclooxygenase-2 inhibitors), where existing assays lack the requisite analytical sensitivity.

Increasing the analytical sensitivity will result in a lowering of the cutoff concentration at the $99^{th}$ percentile, and will result in a higher frequency of positive troponin results in patients who present to the emergency department with chest pain. Unless ischemia can be ruled out by clinical or other means, a mildly increased troponin will produce more false positive cases of AMI. In order to reduce the diagnostic confusion caused by high sensitivity troponin assays, the National Academy of Clinical Biochemistry advocated the use of serial testing. Troponin concentrations that are stable over an appropriate sampling interval are more likely caused by chronic diseases such as renal failure, heart failure, sepsis, and myocarditis. The NACB recommended a change of 20% from baseline as suggestive of an AMI that is either evolving (rise in troponin) or resolving (fall in troponin). This limit was determined based a calculation of three times the imprecision at the cutoff concentrations and not from the marker's biological variation. There have been no recommendations to date as to how serial results of troponin should be interpreted in the context of risk stratification for future adverse events or cardiac toxicity due to therapeutic drugs.

A more rigorous determination of statistically significant reference change values of serial testing is based on measurement of an analyte's biologic variation. These studies are usually conducted in healthy subjects with no evidence of active cardiovascular disease. However, until assays were available that could reliably detect troponin in healthy subjects, such studies were not possible. Biological variability studies cannot be conducted on diseased patients due to the changing concentrations of troponin over time in patients with acute coronary syndromes (ACS) or chronic diseases such as heart and renal failure. Therefore, we determined the short- and long-term biological variability on healthy subjects using a prototype cTnI assays with 10-50 times higher analytical sensitivity than the best that is available among the commercially-available assays.

Materials and Methods

Patients and Specimens

Two separate cohorts of subjects were recruited for this study using a protocol that was reviewed and approved by the University of California Committee for Human Research and the San Francisco General Hospital (SFGH) General Clinical Research Center (GCRC). All subjects signed a written consent. For the short-term biological variability, 12 subjects (6 males and 6 females, age range 23-54 y) were recruited. A heparin lock was inserted into the antecubital vein by staff at the SFGH GCRC. Thereafter, blood was collected at 0, 1, 2, 3, and 4 hours through the heparin lock into vacutainer tubes containing no anticoagulant. A small amount of blood was discarded prior to blood collection to flush the line of heparin. After collection, a small amount of heparin was injected into the intravenous lines to maintain patency. The collected blood was allowed to clot, the tubes centrifuged within 30 minutes, and the serum aliquoted and frozen at −70° C. until analysis. For the long-term biological variability, 17 subjects (9 males and 10 females, age range 19-58 y) were recruited. Blood was collected through venipuncture every other week for 6-8 weeks (3-4 total samples per subject). Samples were centrifuged and stored at −70° C. and thawed (once) prior to analysis. To minimize the pre-analytical variability, the same phlebotomist was used for each subject. For the long-term study, blood was collected on the same day of the week and roughly the same time of the day. For both cohorts, the subjects self-reported no symptoms or history of heart disease.

Data Analysis

Frozen samples were allowed to thaw at room temperature. All analytical assays for cardiac troponin were performed at Singulex Inc., Hayward, Calif. using the analyzer, compositions, and methods, and were tested in duplicate using the same technologist on the same day (different days for each of the short- and long-term studies). All results and calculations were performed using Microsoft Excel (Redmond, Wash.). We use the Cochran's test to determine the presence of outliers among patient results. We found that the distribution of troponin data was non-parametric and therefore performed a log normal transformation of the troponin results prior to calculation of the biological variation. The equations established by Fokkema et al. were used instead of the more widely-used nested ANOVA procedures of Fraser et al., who do not describe log transformation. For calculation of the reference change value, this transformation resulted in non-symmetric limits, i.e., separate criteria for statistically significant difference between increasing and decreasing troponin values. We determined the goals for precision ($\leq 0.5 \times CV_I$) and accuracy ($\leq 0.25 \times (CV_I^2 + CV_T^2)^{1/2}$) using the convention of Fraser et al.

In summary, for the assessment of short-term variation, blood was collected on every hour for 4 hours (5 samples total each) on 12 healthy subjects. For the assessment of long-term variation, blood was collected every other week for 8 weeks (3-4 samples each) on 17 healthy subjects. Blood was tested using a high sensitivity cTnI assay (limit of detection 0.2 ng/L). The analytical coefficient of variance ($CV_A$), intra-individual ($CV_I$) and total median ($CV_T$) variation, index of individuality were computed. As the data was non-parametrically distributed, the reference change values (RCV) were calculated using a log normal approach.

Results

Figure 14B:
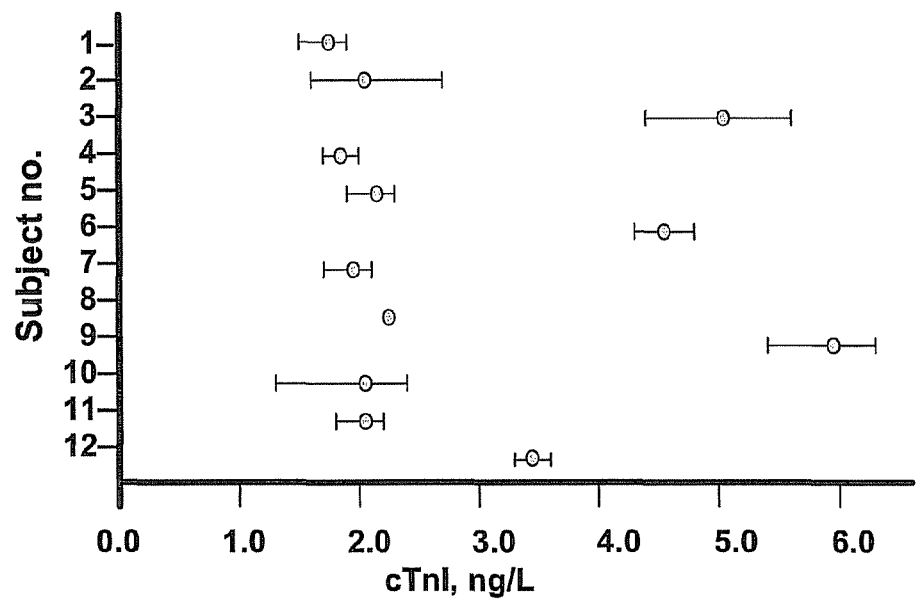
FIGS. 14A and 14B. Distribution of results of biological variation for cardiac troponin.
Figure 14A:
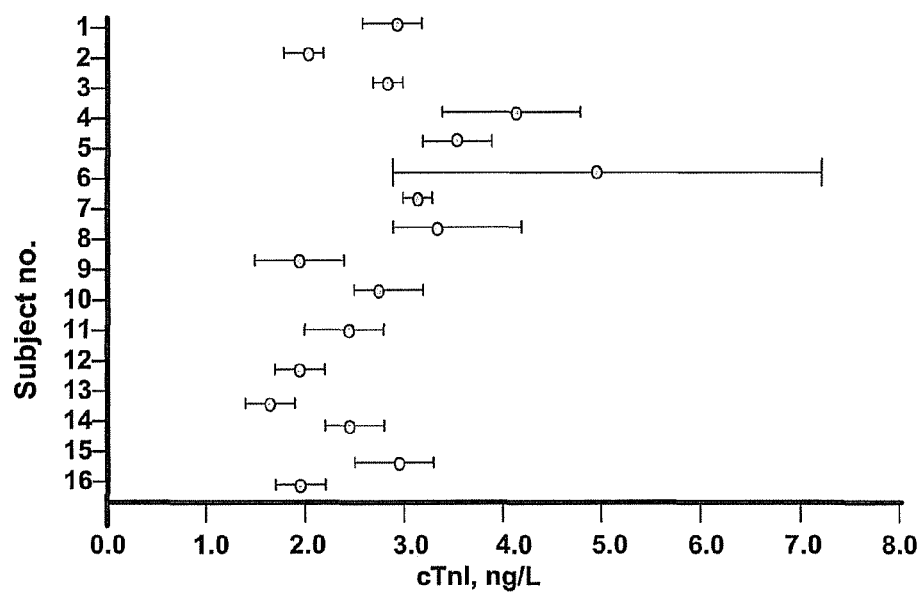

The distribution of results for the short and long-term biological variation for cardiac troponin is shown in FIGS. 14A and 14B, respectively. The mean (points) and range (bars) of values are given. The data shown in FIG. 14A is the short-term biological variation on 12 subjects over 4 hours. The data shown in FIG. 14B is the long-term variation on 15 subjects over 8 weeks. In both FIGS. 14A and 14B, statistical outliers were removed. There were no outliers from the hour-to-hour dataset. From the week-to-week dataset, we determined one subject was determined to be an outlier and was removed. None of the points had values that were below the detection limit of the assay of 0.2 ng/L, and all were below the $99^{th}$ percentile limit of 10 ng/L, previously determined on 100 apparently healthy subjects. Table 9 shows the results of the short and long-term biological variability for cardiac troponin.

TABLE 9

Short and long-term biological variability (BV) for cTnI

| PARAMETER | SHORT-TERM BV$^A$ | LONG-TERM BV$^B$ |
|---|---|---|
| Analytical variation | | |
| $CV_A$, | %7.6 | 12.2 |
| Biological variation | | |
| $CV_I$, % | 7.8 | 9.0 |
| $CV_T$, % | 10.9 | 15.2 |
| Index of individuality | 0.72 | 0.59 |
| Precision goals, % | 3.9 | 4.5 |
| Inaccuracy goals, % | 3.4 | 5.2 |
| RCV: lognormal increase | 35 | 52 |
| RCV: lognormal decrease | −26 | −34 |

$^A$Over 4 hours.
$^B$Over 8 weeks.

The values $CV_I$, and $CV_T$ were slightly lower for the short-term relative to the long-term. This is expected given that changes to the heart are not expected to change in a healthy subject from hour to hour, but may change slightly from week to week. Goals for imprecision, inaccuracy, and index of individuality are also shown with the results of the hour-to-hour values being slightly higher but not significantly different from the week-to-week results.

The distribution of the hour-to-hour and day-to-day cTnI results were non-parametric and right skewed and a log normal transformation was performed prior to the calculation of RCV. This resulted in the production of non-symmetrical RCV results, with higher limits signifying statistical change for increasing cTnI results and lower limits for decreasing results. The higher RCV limit for a rising troponin reflects the right skewed distribution of results from healthy subjects and the greater statistical uncertainty when values are increasing. The calculated RCV results are about 1.5 to 2 times higher than the single limit of 20% change in serial results that was recommended by the NACB. This is partly due to the higher imprecision observed at the lower cTnI concentrations observed for healthy subjects.

The short-term $CV_A$, $CV_I$ and $CV_T$ for cTnI were 7.6% (mean 2.3 ng/L), 7.8%, and 10.9%. Corresponding results for the long-term variation were: 12.2%, 9.0%, and 15.2%. The index of individuality were 0.72 and 0.59, respectively. The RCV were 35% (increase) and −26% (decrease) for short-term, and 52% and −34%, respectively with 95% confidence. The low index of individuality indicates that a population-based reference intervals are less useful than measuring serial change values in individual patients. This is particularly important for the interpretation of patients who have low concentration increases in cTnI using very high-sensitivity assays for patients presenting with chest pain (short-term) and for evaluation of drugs for cardiotoxicity (long-term).

The determination of the biological variation for cardiac troponin has not been previously possible due to the lack of analytical sensitivity of assays to reliably measure troponin in the blood of healthy subjects. The availability of high sensitivity troponin assays now enables the reliable detection of troponin due to the normal turnover of cardiac myocytes with the requisite imprecision ($\leq 10\%$). Two different research assays have now shown that there is anon-parametric distribution of cardiac troponin in healthy subjects. The results in this study were consistent with these previous findings.

Table 10 compares the biological variation for cardiac troponin when measured over the short term, against the other commonly used cardiac biomarkers of ACS. Total CK, CK-MB activity, CK-MB mass, and myoglobin are described as "event markers," such as plaque erosion in the case of AMI. The $CV_I$ for these troponin and CK-MK mass are low relative to the $CV_T$, producing a low index of individuality. An low index (<0.6) indicates that reference intervals will be of little utility for interpretation of individual results whereas an index that his high (>1.4) indicates that reference values are of significant value. Table 10 shows that the traditional ACS markers have a low index. In this study, the short-term troponin index was slightly higher at 0.72 than the other markers, reinforcing the notion that serial testing is an important criteria for diagnosis of low level increases.

The biological variation data does not influence the interpretation of patients who have a very high troponin concentration, e.g., a 10-fold increases relative to the $99^{th}$ percentile cutoff. These patients should be immediately admitted and treated without a need for serial troponin testing. In contrast, proper use of the biological variation will be important in the interpretation of minor increases of troponin, i.e., values at or just above the $99^{th}$ percentile limit when very high sensitivity assays are used. Serial cardiac troponin values that exceed the upper RCV in the clinical context of chest pain increase the likelihood that the patient is suffering an evolving AMI. This interpretation may be valid even if all serial troponin results are below the population-based reference limit (due to the low index of individuality). However, there may be other acute disease processes that can increase troponin concentrations over the short term, such as sepsis. Patients with serial troponin values that are mildly increased but are unchanging would increase the likelihood that a chronic cardiac condition is present that is known to cause cardiac damage (e.g., myocarditis, heart and kidney failure). Patients with declining serial troponin results might indicate a resolving AMI, particularly if there is a history of chest pain from the prior days or week. It should be noted that patients with a positive troponin due to a chronic disease can present with an acute exacerbation and increasing troponin values that mimic an AMI release pattern. Therefore clinical judgment remains paramount in the interpretation of troponin testing.

Table 10 also compares long-term biological variation of cardiac troponin against other biomarkers that are used for chronic disease detection.

TABLE 10

Summary of Biological Variation for Cardiac Markers

| MARKER | $CV_A$ | $CV_I$ | $CV_T$ | II | RCV | DURATION | REFERNCE |
|---|---|---|---|---|---|---|---|
| Acute disease markers | | | | | | | |
| Creatine kinase | 14.0 | 22 | 42.2 | 0.52 | 72.2 | Daily | Ross et al. |
| CK-MB, activity | 29.1 | 4.9 | 14.1 | 0.35 | 81.8 | Daily | Ross et al. |
| CK-MB, mass | 6.8 | 18.4 | 61.2 | 0.30 | 54.4 | Daily | Ross et al. |
| Myoglobin | 13.4 | 17.6 | 46.6 | 0.38 | 61.2 | Daily | Ross et al. |
| Troponin I | 7.6 | 7.6 | 10.9 | 0.72 | +35, −26 | Hourly | This Study |
| Chronic disease markers | | | | | | | |
| Myoglobin | 6.0 | 11.1 | 13.8 | 0.80 | 35.0 | Weekly | Panteghini et al. |
| C-reactive protein | 5.2 | 42.2 | 92.5 | 0.46 | 118 | Weekly | Macy et al. |
| C-reactive protein | 1.0 | 36.8 | 62.2 | 0.59 | 102 | 4 days | Cho et al. |
| Serum amyloid A | 4.0 | 25.0 | 61.0 | 0.40 | 70.1 | Weekly | Melzi d'Eril et al. |
| Myeloperoxidase | 4.0 | 36.0 | 30.0 | 1.20 | 100 | Weekly | Dednam et al. |
| BNP | 8.4 | 40.0 | 41.0 | 0.98 | 113 | Weekly | Wu et al. |
| BNP | | | | | +198, −66 | Weekly | Fokkema |
| NT-proBNP | 3.0 | 35.0 | 35.0 | 1.00 | 98 | Weekly | Bruins et al. |
| NT-proBNP | 1.6 | 33.3 | 36.5 | 0.90 | 92 | Weekly | Wu et al. |
| NT-BNP | | | | | +157, −61 | Weekly | Fokkema |
| Troponin I | 12.2 | 9.0 | 15.2 | 0.59 | 52, −34 | Weekly | This Study |

[1]Conducted in healthy subjects.
[2]Conducted in stable heart failure patients.
[3]Lognormal transformation of Bruins et al. (22) data.

These markers include myoglobin, high sensitivity C-reactive protein (hsCRP), serum amyloid A, and myeloperoxidase for atherosclerosis, and B-type natriuretic peptide (BNP) and NT-proBNP for heart failure 23). Both the $CV_I$ and $CV_T$ are in general higher for long-term "disease" markers than for the short-term event markers. This is not unexpected given that the interval between blood collections is weeks instead of hours. The low index of individuality for the inflammatory markers (0.4-0.59, from Table 2) suggests that reference intervals will not be useful, and that serial testing will be required. In contrast, for the natriuretic peptides, the higher index of individuality (0.9-1.1, Table 2) suggests that reference intervals are appropriate. For both the inflammatory markers and natriuretic peptides, the high biological variation results in relatively high RCV values (70 to 198%). Therefore minor changes in serial results will not be meaningful as recently suggested for hsCRP. Others have challenged the utility of biological variation for determining significant serial change values for hsCRP and BNP. The results for the index of individuality for cardiac troponin are between hsCRP and BNP.

The results for cardiac troponin for monitoring of cardiac disease are significantly different than for the other chronic cardiac disease markers. The biological variation, index of individuality and RCVs are much lower. Although hsCRP, myeloperoxidase and BNP are useful for risk stratification, the results on troponin suggest that high sensitivity assays can be applied to detection of minor myocardial damage due to drugs that may be cardiotoxic. Patients on these drugs are currently not routinely tested for cardiac troponin. This is because the existing commercial assays lack the sensitivity to low to detect very minor and chronic increases. With the development of high sensitive assays, the utility of cardiac troponin should be re-examined for this application. If proven to be useful, the long-term biological variation and calculation of the RCV will be relevant. Recently, high-sensitivity troponin T assays have been developed and similar biological variability studies need to be performed to determine how serial changes can be interpreted in the context of acute and chronic cardiovascular disease.

Example 9

Specificity of a High Sensitivity Cardiac Troponin-I Assay Utilizing Single Molecule Counting Technology Recent guidelines for cTnI recommend a $99^{th}$ percentile cutoff value with assay imprecision <10%. However, most commercial assays do not meet these criteria and cTnI values below the $99^{th}$% value provide diagnostic and prognostic information.

Values of cardiac troponin I are the mainstay for the diagnosis or exclusion of acute myocardial infarction (AMI) and for risk stratification in patients who present with acute coronary syndromes. The European Society of Cardiology, American Heart Association, World Heart Federation and American College of Cardiology have recommended that the $99^{th}$ percentile be used as the most appropriate cutoff concentration for troponin. It is recommended that there be no more than 10% assay imprecision at the $99^{th}$ percentile value. Given that most commercial assays do not have the sensitivity and precision to meet these goals and the fact that it has become clear over time that detectable values below the 99th percentile value carry important prognostic information, there is interest among manufacturers to increase the sensitivity of commercial troponin assays.

Recently, a new cardiac troponin I (cTnI) assay was described that uses single-photon fluorescence detection and antibody coated microparticles (MPs) as a solid phase capture reagent. It appears considerably more sensitive than commercial assays. The analyzer, compositions, and methods of the cTnI assay reports values of cardiac troponin I in the blood of healthy subjects, with a preliminary 10% CV at 1.8 ng/L and a 99th percentile cutoff value of 10 ng/L. These lower cutoff values likely will produce more and earlier positive test results in patients who present to emergency departments with chest pain than the older troponin assays.

It is important to demonstrate the analytical specificity of this highly sensitive cTnI assay with regard to false-negatives and false-positives. Some degree of assay interference has already been recognized from heparinized and chelated serum samples, as well as troponin autoantibody interference, which produce false-negative results at low troponin concentrations. False-positives may occur if troponin readings from healthy subjects are due to non-specific binding of serum or plasma components to the antibodies used in the assay, rendering results of the assay invalid. This investigation was designed to indirectly test this issue, predicated on the assumption that if a non-specific cTnI signal was being obtained from the samples, it would also be observed by other antibody coated MPs.

Methods

Concentrations of cTnI were determined from 20 normal subjects across four specimen types (serum, EDTA, lithium heparin and citrate plasma) and 8 additional serum samples from apparently healthy blood donors (AVG+/−SD). To test for specificity, microparticles (MPs) were coated with a panel of unrelated antibodies (A-beta42, MIP-1a, G-CSF and PSA) or left un-coated (blank MPs) and assayed for cTnI. Standard curves were generated using the NIST cTnI standard analyte compared to a skeletal troponin analyte.

Serum, EDTA, lithium heparin and sodium citrated plasma was collected from 20 subjects who were free of cardiac disease or symptoms (13 female, 7 male, average 43 y, range 23-64 y). The protocol was reviewed and approved by the University of California Committee on Human Research and all subjects signed a written consent. The blood was centrifuged within 30 minutes of collection, aliquoted and stored frozen at −70° C. until analysis. Eight additional serum samples were obtained from healthy blood bank donors to test for non-specific antibody interactions (4 male, 4 female, average 25.5 y, range 22-30 y). Frozen serum and plasma were provided to Singulex (blinded to donor ID) and assayed with the analyzer, compositions, and methods. Briefly, specimens were thawed at room temperature, centrifuged for 10 minutes at 13,000×g and the clarified specimen was placed into a clean tube. Each 50 ul specimen (neat serum or plasma) was mixed with 150 ul assay buffer containing paramagnetic microparticles (Dynabeads MyOne Streptavidin C1, Invitrogen) in the well of a 96 plate. For analysis across sera types, MPs were coated with a cTnI capture monoclonal antibody (R&D Systems). For specificity studies, MPs were either left un-coated (blank MPs) or coated with one of the following monoclonal antibodies: amyloid-beta-42 (A-beta42, Covance), macrophage inflammatory protein-1 alpha (MIP-1a, R&D Systems), granulocyte-colony stimulating factor (G-CSF, R&D Systems), and prostate specific antigen (PSA, BiosPacific). These antibodies (both isotype matched and un-matched) were chosen to represent a variety of antibodies raised against epitopes which are un-related to cardiac troponin I, to test for evidence of non-specific antibody interactions in the assay conditions. All antibodies were biotinylated and coated onto streptavidin MPs at 15 ug IgG per mg of MPs according to manufacturer's recommendations. The assay consisted of a one hour capture step, one wash of MPs, a 30 minute detection step with polyclonal goat anti cTnI (Biospacific) labeled with fluorescent dye and diluted in assay buffer, 5 washes, and 30 minutes of elution of detection antibody bound to the MPs. All specimens, calibrators and controls were tested in triplicate and results are presented as an average of the determinations+/− standard deviation. Inter-assay precision was determined by assay of two control sera over 14 assay runs performed over 4 days. Analyte specificity was tested through linear regression analysis of cTnI standard (NIST) and non-specific skeletal troponin (Hytest) analytes, assayed over a range of 0.1-100 ng/L.

Results cTnI was quantifiable in 93% of serum and plasma specimens, and no significant differences in cTnI concentrations across specimen types were observed (95% CI). Out of all samples and non-specific antibodies tested, one sample displayed quantifiable non-specific interaction with the A-beta-42 antibody (55% CR). No non-specific events were observed when skeletal troponin was used as the analyte.

Figure 15:
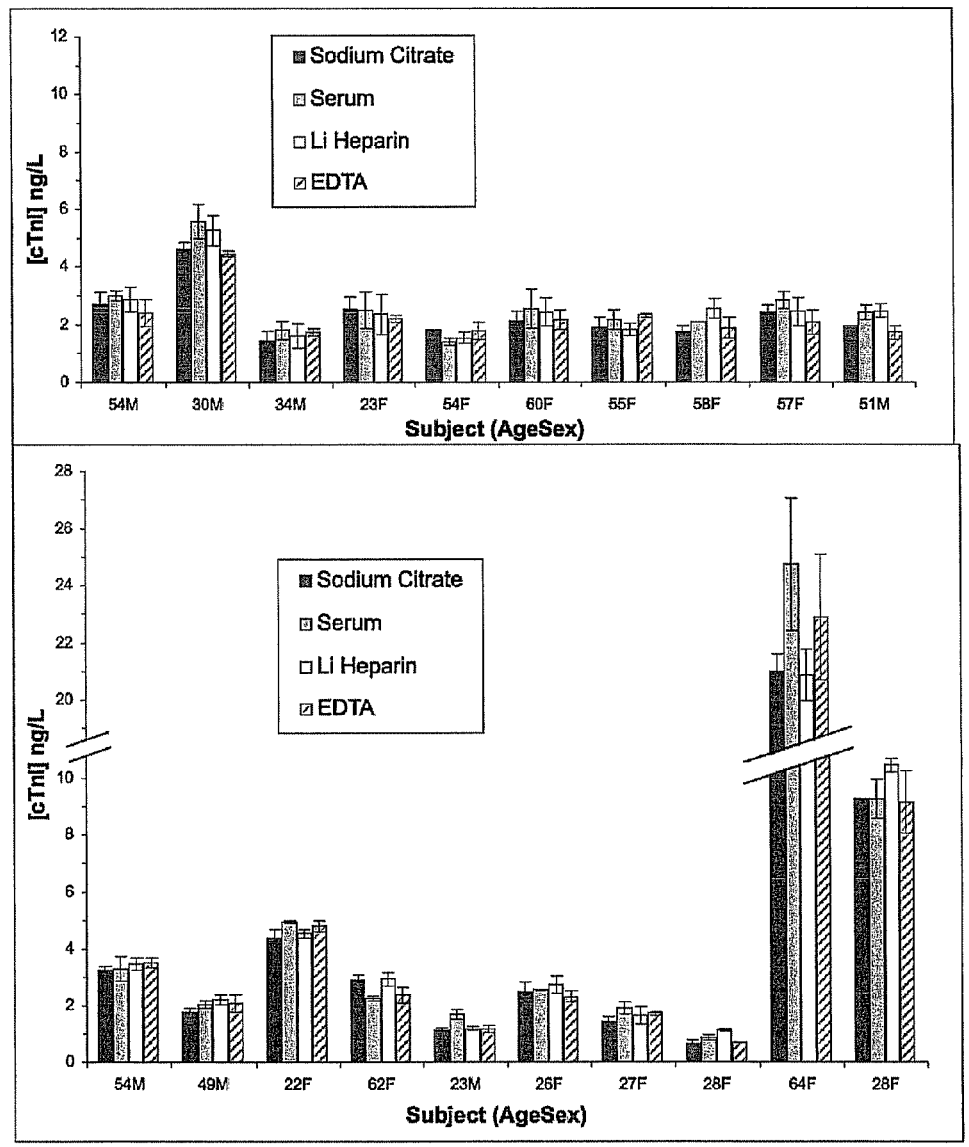
FIG. 15. Graph showing concentrations of cTnI (ng/L) in matched serum and plasma specimens obtained from 20 human donors of mixed age and sex. Samples were run in triplicate and results for each sample are presented as the mean+/−standard deviation.

From the 20 donor sera and plasma samples collected, there were no apparent trends in cTnI measurements based upon donor's age or sex (FIG. 15). Figure shows concentrations of cTnI (ng/L) in matched serum and plasma specimens obtained from 20 human donors of mixed age and sex. Samples were run in triplicate and results for each sample are presented as the mean+/− standard deviation. For each donor the average cTnI value was assessed across the 4 specimen types (average 3.76+/−4.76 ng/L, range 0.84-22.37 ng/L). All determinations fell within two standard deviations from the mean, indicating no significant differences in cTnI concentration between specimen types (95% CI). One donor presented with elevated levels of cTnI across all specimen types, and this maximum value was identified as a statistical outlier using Grub's test (p<0.05) and removed from further analysis. Removal of this sample produced an adjusted average cTnI value of 2.78+/−1.93 ng/L similar to values reported previously. In two control sera, inter-assay precisions of 7% CV and 10% CV were measured with average cTnI measurements of 8.3 and 2.2 ng/L, respectively.

Across all 28 donors, cTnI was detectable in all (LoD 0.2 ng/L) and quantifiable for 93% (LLoQ 1 ng/L) of matched serum and plasma specimens tested (Table 11).

TABLE 11

Cross reactivity in normal, human serum samples of the Singulex MP-based cTnI Assay using non-specific capture antibodies.

| MP Capture Antibody | Total Samples | ND (< LoD, 0.2 ng/L) | | DNQ (1.0 ng/L > X ≧ 0.2 ng/L) | | Quantifiable (≧ LLoQ, 1.0 ng/L) | |
|---|---|---|---|---|---|---|---|
| | (n) | (n) | % | (n) | % | (n) | % |
| cTnI | 28 | 0 | 0 | 2 | 7 | 26 | 93 |
| Blank | 28 | 26 | 93 | 2 | 7 | 0 | 0 |
| AB-42 | 20 | 18 | 90 | 1 | 5 | 1* | 5 |
| MIP-1a | 8 | 6 | 75 | 2 | 25 | 0 | 0 |

TABLE 11-continued

Cross reactivity in normal, human serum samples of the Singulex MP-based cTnI Assay using non-specific capture antibodies.

| MP Capture Antibody | Total Samples (n) | ND (<LoD, 0.2 ng/L) (n) | | DNQ (1.0 ng/L > X ≧ 0.2 ng/L) (n) | | Quantifiable (≧ LLoQ, 1.0 ng/L) (n) | |
|---|---|---|---|---|---|---|---|
| | | (n) | % | (n) | % | (n) | % |
| PSA | 8 | 7 | 88 | 1 | 13 | 0 | 0 |
| G-CSF | 8 | 8 | 100 | 0 | 0 | 0 | 0 |

*One serum sample displayed 55% CR with AB-42 (1.26 ng/L) compared to cTnI (2.36 ng/L).
Abbreviations:
Cross reactivity (CR),
non-detectable (ND),
detectable but non-quantifiable (DNQ)

Serum and plasma specimens from one of the twenty volunteers (5%) was quantifiable for a non-specific antibody, which displayed 55% cross reactivity with A-beta-42 (1.26 ng/L) compared to cTnI (2.36 ng/L). No other samples were quantifiable for cTnI when using a non-specific capture antibody or when using blank MPs. Some low level non-specific reaction (less than the LLoQ and greater than the LoD) was observed for blank microparticles (7%) and for non-specific capture antibodies A-beta-42 (5% donors), MIP-1a (25% donors), and PSA (13% donors). No non-specific reactions were observed when G-CSF was used as the capture antibody. In tests of analyte specificity, back-interpolated standard curve analysis of the NIST standard cTnI analyte (y=1.053x−0.229, $R^2$=0.999) showed poor correlation when compared to analysis of the orthologous skeletal troponin analyte (y=0.000x+0.156, $R^2$=0.001) in the analyzer, compositions, and methods.

These data support the specificity of the novel single molecule assay for the quantification of cTnI. We have previously shown that serum specimens provide a linear response when diluted with synthetic calibrator diluent, however, we could not exclude the possibility that with such sensitive limits of detection some other material was captured along with cTnI and then non-specifically measured. This study provides a more robust test by substituting a series of non-specific, non-isotype matched, but high affinity antibodies in the capture position to further evaluate that possibility. Our data support the contention that the assay specifically measures cTnI in most apparently healthy subjects. Even in subjects that showed low-levels of non-specific binding, this binding was below the limit of quantification reported for the assay in all but one case (See Table 11). In the one case where non-specific binding was quantifiable, it accounted for 55% of the cTnI signal. The magnitude of this effect would not have moved this subject out of the normal range projected for the assay.

Data like these are critical as the field moves forward. As more sensitive detection techniques such as the novel assay used in this approach are developed, confirmation of the specificity of their detection is essential. Thus, similar cross reactivity studies which evaluate potential issues with troponin orthologs (i.e., skeletal muscle TnI and TnT) and other non-specific binding events are critical adjuncts to the validation of these assays. Because of the sensitivity of this novel assay, conventional methods may not be adequate to provide this specificity information, requiring an equally novel approach to the validation issue. These data, taken together with those reported previously predicated on linear dilution and immunodepletion, provide strong evidence that this particular cTnI assay approach has maintained the specificity of detection.

The data presented provides further documentation that the analyzer, compositions, and methods have high specificity and reliably measure cTnI in apparently healthy human subjects. This high degree of specificity and high sensitivity should allow for further investigation of the clinical significance of mild increases in cTnI in patients with and without acute coronary disease.

REFERENCES

1. Hogrefe W R. Biomarkers and assessment of vaccine responses. Biomarkers 2005; 10 Suppl 1:S50-7.
2. Banks R E. Measurement of cytokines in clinical samples using immunoassays: problems and pitfalls. Crit. Rev Clin Lab Sci 2000; 37:131-82.
3. Meriggioli M N. Use of immunoassays in neurological diagnosis and research. Neurol Res 2005; 27:734-40.
4. Lim C T, Zhang Y. Bead-based microfluidic immunoassays: the next generation. Biosens Bioelectron 2007; 22:1197-204.
5. Martin K, Viera K, Petr C, Marie N, Eva T. Simultaneous analysis of cytokines and co-stimulatory molecules concentrations by ELISA technique and of probabilities of measurable concentrations of interleukins IL-2, IL-4, IL-5, IL-6, CXCL8 (IL-8), IL-10, IL-13 occurring in plasma of healthy blood donors. Mediators Inflamm 2006; 2006:65237.
6. Guthrie J W, Hamula C L, Zhang H, Le X C. Assays for cytokines using aptamers. Methods 2006; 38:324-30.
7. Dupuy A M, Lehmann S, Cristol J P. Protein biochip systems for the clinical laboratory. Clin Chem Lab Med 2005; 43:1291-302.
8. Dhawan S. Signal amplification systems in immunoassays: implications for clinical diagnostics. Expert Rev Mol Diagn 2006; 6:749-60.
9. Wu A F N, Todd J, Puskas R, Goix P. Development and preliminary clinical validation of a high sensitive assay for cardiac troponin using capillary flow (single molecule) fluorescence detection. Clin Chem 2006; 52:2157-8.
10. McGavigan A D, Maxwell P R, Dunn F G. Serological evidence of early remodeling in high-risk non-ST elevation acute coronary syndromes. Int J Cardiol 2007.
11. O'Brien P J. Blood cardiac troponin in toxic myocardial injury: archetype of a translational safety biomarker. Expert Rev Mol Diagn 2006; 6:685-702.
12. Schupbach J. Viral RNA and p24 antigen as markers of HIV disease and antiretroviral treatment success. Int Arch Allergy Immunol 2003; 132:196-209.
13. Toyo-oka T, Kumagai H. Cardiac troponin levels as a preferable biomarker of myocardial cell degradation. Adv Exp Med Biol 2007; 592:241-9.
14. Joint European Society of Cardiology/American College of Cardiology Committee. Myocardial infarction redefined—a consensus document of the joint European Society of Cardiology/American College of Cardiology Committee for the redefinition of myocardial infarction. J Am Coll Cardiol 2000; 36:959-69.
15. Todd J, Freese B, Lu A, Held D, Morey J, Livingston R, et al. Ultrasensitive flow-based immunoassays using single-molecule counting. Clin Chem 2007; 53:1990-5.
16. H B, Fukushima F, Puskas R, Todd J, Goix P. Development and preliminary clinical validation of a high sensitivity assay for cardiac troponin using a capillary flow (single molecule) fluorescence detector. Clin Chem 2006; 52:2157-9.
17. H B, Lu A, Freese B, Todd J. Development and preliminary clinical validation of an ultra-sensitive assay for cardiac troponin using microparticle based immunoassay and single molecule counting. Clin Chem 2007; 53(suppl): A15. [Abstract].
18. H B, Jaffe A S. The clinical need for high sensitivity cardiac troponin assays for ACS and the role for serial testing. Am Heart J 2008; 155:208-14.
19. Melanson S E F, Morrow D A, Jarolim P. Earlier detection of myocardial injury in a preliminary evaluation using a new troponin I assay with improved sensitivity. Am J Clin Pathol 2007; 128:282-6.
20. Morrow D A, Cannon C P, Rifai N, et al. Ability of minor elevations of troponins I and T to predict benefit from an early invasive strategy in patients with unstable angina and non-ST elevation myocardial infarction: results from a randomized trial. JAMA 2001; 286:2405-2412.
21. Sparano J A, Wolff A C, Brown D. Troponins for predicting cardiotoxicity from cancer therapy. Lancet 2000; 356: 1947-8.
22. Levesque L E, Brophy J M, Zhang B. Time variations in the risk of myocardial infarction among elderly users of COX-2 inhibitors. CMAJ 2006; 174:1563-9.
23. Wu A H B, Apple F S, Jaffe A S, Jesse R L, Morrow D A, Newby K, et al. National Academy of Clinical Biochemistry Laboratory Medicine Practice Guidelines: use of cardiac troponin and the natriuretic peptides for etiologies other than acute coronary syndromes and heart failure. Clin Chem 2007, 53:2086-96.
24. Cochran W S. The distribution of the largest of a set of estimated variances as a fraction of their total. Ann Eugen 1941; 11:47-52.
25. Fokkema M R, Herrmann Z, Muskiet F A J, Moecks J. Reference change values for brain natriuretic peptides revisted. Clin Chem 2006; 52:1602-3.
26. Fraser C G, Harris E K. Generation and application of data on biological variation in clinical chemistry. Crit. Rev Clin Lab Sci 1989; 27:409-37.
27. Bao P, Wei T F, Cork K, Hollander J, Shipp G. A novel technology platform for the ultrasensitive detection of cardiac troponin (cTnI): clinical utility in the emergency department. 2nd Int Symposium. Integrated Biomarkers in Cardiovascular Disease. Berlin, June, 2007 [Abstract].
28. Ross S M, Fraser C G. Biological variation of cardiac markers: analytical and clinical considerations. Ann Clin Biochem 1998; 35:80-4.
29. Harris E K. Statistical aspects of reference values in clinical pathology. Prog CLin Pathol 1981; 8:45-66.
30. Panteghini M, Pagani F. Biological variation of myoglobin in serum. Clin Chem 1997; 43:2435.
31. Macey E M, Hayes T E, Tracy R P. Variability in the measurement of C-reactive protein in healthy subjects: implications for reference intervals and epidemiological applications. Clin Chem 1997; 43:52-8.
32. Cho L W, Jayagopal V, Kilpatrick E S, Atkin S L. The biological variation of C-reactive protein in polycystic ovarian syndrome. Clin Chem 2005; 151:1905-6.
33. Melzi d'Eril G, Anesi A, Maggiore M, Leoni V. Biological variation of serum amyloid A in healthy subjects. Clin Chem 2001; 47:1409-9.
34. Dednam M, Vorster B C, Ubbink J B. The biological variation of myeloperoxidase. Clin Chem 2008, in press.
35. Bruins S, Fokkema M R, Pomer J W P, et al. High intraindividual variation of B-type natriuretic peptide (BNP) and B-type proBNP in patients with stable chronic heart failure. Clin Chem 2004; 50:2052-2058.
36. Wu A H B, Smith A C, Mather J F, et al. Biological variation for NT-pro- and B-type natriuretic peptides and implications for therapeutic monitoring of patients with congestive heart failure. Am J Cardiol 2003, 92:628-31.
37. Wu A H B. Serial testing of B-type natriuretic peptide and NTpro-BNP for monitoring therapy of heart failure: the role of biological variation in interpretation of results. Am Heart J. 2006, 152:828-34.
38. Franzini C. Need for correct estimates of biological variation: the example of C-reactive protein. Clin Chem Lab Med 1998; 36:131-2.
39. Clerico A, Zucchelli G C, Pilo A, et al. Clinical relevance of biological variation of B-type natriuretic peptide. Clin Chem 2005; 51:925-6.
40. Thygesen K, Alpert J S, White H D; Joint ESC/ACCF/AHA/WHF Task Force for the Redefinition of Myocardial Infarction. Universal definition of myocardial infarction. J Am Coll Cardiol 2007; 50:2173-95.
41. Panteghini M, Pagani F, Yeo K T J, Apple F S, Christenson R H, Dati F, Mair J, Ravkilde J, Wu A H B. Evaluation of the imprecision at low-range concentration of the assays for cardiac troponin determination. Clin Chem 2004, 50:327-32.
42. Schulz O, Kirpal K, Stein J, Bensch R, Berghoefer G, Schimke I and Jaffe A S. Importance of low concentrations of cardiac troponins. Clin Chem 2006; 52:1614-5.
43. Schulz O, Paul-Walter C, Lehmann M, Abraham K, Berghöfer G, Schimke I and Jaffe A S. Usefulness of detectable levels of troponin, below the 99th percentile of the normal range, as a clue to the presence of underlying coronary artery disease. Am J Cardiol 2007; 100:764-9.
44. Eggers K M, Lagerqvist B, Venge P, Wallentin L, Lindahl B. Persistent cardiac troponin I elevation in stabilized patients after an episode of acute coronary syndrome predicts long-term mortality. Circulation 2007; 116:1907-14.
45. Zethelius B, Johnston N, and Venge P. Troponin I as a predictor of coronary heart disease and mortality in 70-year-old men: A community-based cohort study. Circulation 2006; 113:1071-8.
46. Todd J, Freese B, Lu A, Held D, Morey J, Livingston R, et al. Ultrasensitive flow-based immunoassays using single-molecule counting. Clin Chem 2007; 53:1990-5.
47. Katrukha A, Bereznikova A, Filatov V, Esakova T. Biochemical factors influencing measurement of cardiac troponin I in serum [Review]. Clin Chem Lab Med 1999; 37:1091-5.
48. Eriksson S, Halenius H, Pulkki K, Hellman J, Pettersson K. Negative Interference in cardiac troponin I immunoassays by circulating troponin autoantibodies. Clin Chem 2005; 51:839-47.
49. Wu A H B, Fukushima N, Puskas R, Todd J, Goix P. Development and preliminary validation of a high sensitivity assay for cardiac troponin using a capillary flow (single molecule) detector. Clin Chem 2006; 52:2157-8.
50. Joint European Society of Cardiology/American College of Cardiology Committee. Myocardial infarction redefined—a consensus document of the joint European Society of Cardiology/American College of Cardiology Committee for the redefinition of myocardial infarction. J Am Coll Cardiol 2000; 36:959-69.

What is claimed is:

1. A method for determining cardiovascular health of an individual comprising:
   (a) measuring serum or plasma concentration of Cardiac Troponin I (cTnI) from a blood sample from the individual in as assay having a limit of detection of less than 30 pg/mL;
   (b) comparing the measured concentration to a predetermined threshold concentration representing the $99^{th}$ percentile concentration of cTnI in a group of normal individuals, wherein the threshold concentration is no more than about 10 pg/mL;
(c) determining cardiac damage in the individual when the concentration of cTnI is greater than the threshold concentration.

2. The method of claim 1, wherein cardiac damage is determined when the threshold concentration of cTnI is about 7 pg/ml.

3. The method of claim 1, wherein cardiac damage is determined when the threshold concentration of cTnI is about 8 pg/ml.

4. The method of claim 1, wherein cardiac damage is determined when the threshold concentration of cTnI is about 9 pg/ml.

5. The method of claim 1, wherein a blood sample is taken during a stress test.

6. The method of claim 1, wherein a blood sample is taken after the stress test.

7. A method of evaluating a human patient for a previous cardiac event comprising:
(a) obtaining a blood sample from the individual;
(b) detecting a concentration of cTnI in the sample in an assay with a limit of detection of less than 3 pg/mL; and
(c) determining the patient is suspected of experiencing a cardiac event when the detected cTnI level is greater than about 7 pg/ml.

8. The method of claim 7 wherein the patient is suspected of experiencing a cardiac event when the detected level of cTnI is greater than about 8 pg/ml.

9. The method of claim 7 wherein the patient is suspected of experiencing a cardiac event when the detected level of cTnI is greater than about 9 pg/ml.

10. The method of claim 7 wherein the patient is suspected of experiencing a cardiac event when the detected level of cTnI is greater than about 10 pg/ml.

11. A method for testing for myocardial damage in a human patient comprising measuring the patient's blood serum concentration of cTnI, comparing the measured concentration to the normal serum concentration of cTnI of about 1-7 pg/ml, and providing a determination of mycardial damage as a result of the comparison.

12. An improved assay for measuring the myocardial health in a human patient by measuring cTnI, wherein the improvement comprises using a serum concentration of about 1-7 pg/ml as the normal concentration for cTnI, and determining myocardial health by comparing the concentration of cTnI in the patient's serum to the normal concentration.

13. The assay of claim 12 wherein the assay is conducted within about five hours of admitting the patient to an emergency room with a clinical indication of myocardial infraction.

14. The assay of claim 12 wherein early identification of patients in need of therapeutic intervention is made by identifying patients having a serum cTnI concentration of greater than 7 pg/mL.

15. The assay of claim 12 wherein the assay is performed periodically over a period of up to about 30 hours on samples from the same patient taken at different times during the 30 hour period.

16. The method of claim 15 wherein at least one sample is taken during or after a cardiac stress test.

17. A method of determining cardiac damage progression in a human individual comprising: (i) obtaining a series of blood samples from the individual, wherein each sample of the series is obtained at an interval of about 8 hours or less; (ii) detecting a level of cTnI in each sample in an assay having a limit of detection of less than 30 pg/mL; (iii) comparing the detected level of cTnI in the series of samples to a predetermined threshold concentration of no more than about 10 pg/mL; and (iv) determining that cardiac damage is resolving when the detected level of cTnI is above the threshold level but decreases through the series of blood samples, and determining that cardiac damage is worsening when the detected level of cTnI is above the threshold level and increasing through the series of blood samples.

18. The method of claim 17 wherein the individual is a patient being evaluated for at least one of a possible cardiac event and cardiotoxicity.

19. The method of claim 17 wherein the threshold level is greater than about 7 pg/ml.

20. The method of claim 17 wherein the threshold level is greater than about 8 pg/ml.

21. The method of claim 17 wherein the threshold level is greater than about 9 pg/ml.

* * * * *